(12) United States Patent
Phan

(10) Patent No.: US 8,105,358 B2
(45) Date of Patent: Jan. 31, 2012

(54) MEDICAL IMPLANTS AND METHODS

(75) Inventor: Christopher U. Phan, San Leandro, CA (US)

(73) Assignee: Kyphon SARL, Neuchatel (CH)

( * ) Notice: Subject to any disclaimer, the term of this patent is extended or adjusted under 35 U.S.C. 154(b) by 356 days.

(21) Appl. No.: 12/182,429

(22) Filed: Jul. 30, 2008

(65) Prior Publication Data

US 2009/0198337 A1 Aug. 6, 2009

Related U.S. Application Data

(60) Provisional application No. 61/025,991, filed on Feb. 4, 2008.

(51) Int. Cl.
*A61B 17/70* (2006.01)
(52) U.S. Cl. .................. 606/249; 606/246; 606/279
(58) Field of Classification Search .......... 606/246–279; 623/17.11–17.16
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |

(Continued)

FOREIGN PATENT DOCUMENTS

DE 2821678 A1 11/1979

(Continued)

OTHER PUBLICATIONS

"Dispositivo Intervertebrale Ammortizzante DIAM," date unknown, p. 1.

(Continued)

*Primary Examiner* — Eduardo C Robert
*Assistant Examiner* — Nicholas Plionis

(57) ABSTRACT

An apparatus includes a spacer, a proximal retention member, a distal retention member, and an actuator. The spacer is configured to engage adjacent spinous processes. The proximal retention member is coupled to the spacer such that a portion of the proximal retention member is in contact with a proximal surface of the spacer. An axis within a plane defined by a first surface of the distal retention member is non-parallel to and non-normal to a longitudinal axis of the spacer. The distal retention member is movably coupled to the spacer such that a second surface of the distal retention member contacts a distal surface of the spacer. The actuator is movably coupled to the spacer and is configured to move relative to the spacer along the longitudinal axis. An actuation surface of the actuator is slidably coupled to and substantially parallel to the first surface of the distal retention member.

9 Claims, 29 Drawing Sheets

U.S. PATENT DOCUMENTS

| | | |
|---|---|---|
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,522,899 A | 6/1996 | Michelson |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,768,794 A | 6/1998 | Kelly |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young et al. |
| 6,214,037 B1 | 4/2001 | Mitchell et al. |
| 6,214,050 B1 | 4/2001 | Huene |
| 6,245,107 B1 | 6/2001 | Ferree |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,427,351 B1 | 8/2002 | Matthews et al. |
| 6,432,130 B1 | 8/2002 | Hanson |
| 6,436,140 B1 | 8/2002 | Liu et al. |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,676,665 B2 | 1/2004 | Foley et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |

| | | |
|---|---|---|
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,383,639 B2 | 6/2008 | Malandain |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,862,615 B2 | 1/2011 | Carli et al. |
| 7,901,430 B2 | 3/2011 | Matsuura et al. |
| 7,927,354 B2 | 4/2011 | Edidin et al. |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0176925 A1 | 9/2003 | Paponneau |
| 2003/0220650 A1 | 11/2003 | Major et al. |
| 2004/0010312 A1 | 1/2004 | Enayati |
| 2004/0010316 A1 | 1/2004 | William et al. |
| 2004/0064094 A1 | 4/2004 | Freyman |
| 2004/0087947 A1 | 5/2004 | Lim et al. |
| 2004/0097931 A1 | 5/2004 | Mitchell |
| 2004/0102774 A1 | 5/2004 | Trieu |
| 2004/0106995 A1 | 6/2004 | LeCouedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0172029 A1 | 9/2004 | Lerch |
| 2004/0186577 A1 | 9/2004 | Ferree |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0113842 A1 | 5/2005 | Bertagnoli et al. |
| 2005/0125061 A1 | 6/2005 | Zucherman et al. |
| 2005/0143827 A1 | 6/2005 | Globerman et al. |
| 2005/0165398 A1 | 7/2005 | Reiley |
| 2005/0182416 A1 | 8/2005 | Lim et al. |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064038 A1 | 3/2006 | Omata et al. |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1 | 3/2007 | Edidin et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0161991 A1 | 7/2007 | Altarac et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0225810 A1 | 9/2007 | Colleran et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |

| | | | |
|---|---|---|---|
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0021468 A1 | 1/2008 | Zucherman et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0177306 A1 | 7/2008 | Lamborne et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0099610 A1 | 4/2009 | Johnson et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0270918 A1 | 10/2009 | Attia et al. |
| 2009/0292316 A1 | 11/2009 | Hess |
| 2009/0326538 A1 | 12/2009 | Sennett et al. |
| 2010/0121379 A1 | 5/2010 | Edmond |
| 2010/0191241 A1 | 7/2010 | McCormack et al. |
| 2010/0204732 A1 | 8/2010 | Aschmann et al. |
| 2010/0211101 A1 | 8/2010 | Blackwell et al. |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | 9921500 A | 5/1999 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | 2004019829 A | 3/2004 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007/052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Tecnica Operatoria Per Il Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilite Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Societè di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative a L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maitrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

International Search Report in PCT/US2009/031182, filed Jan. 16, 2009, 5 pages.

Kramer et al., "Intervetertebral Disk Diseases; Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6: Supplement.

Anasetti et al., "Spine Stability After Implantation of an Interspinous Device: An in Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," The Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

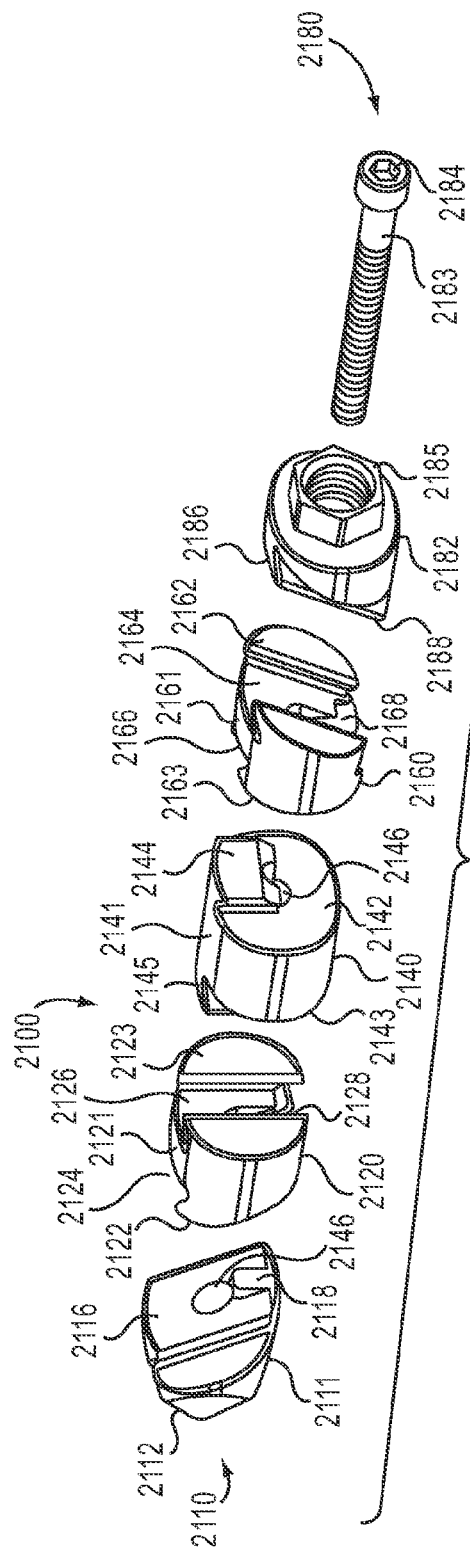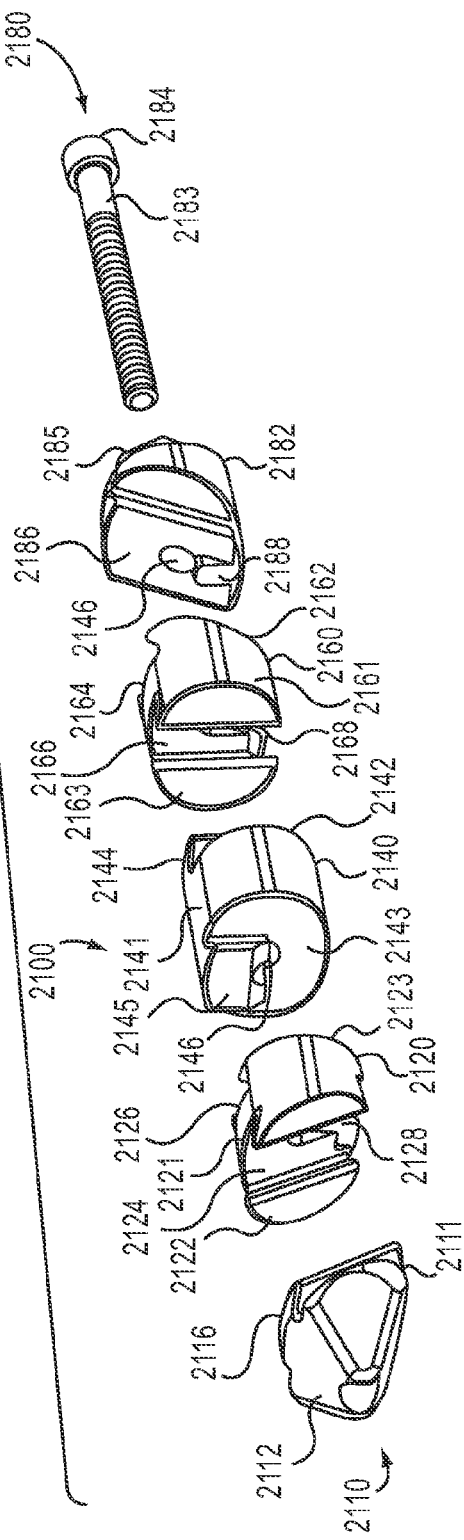

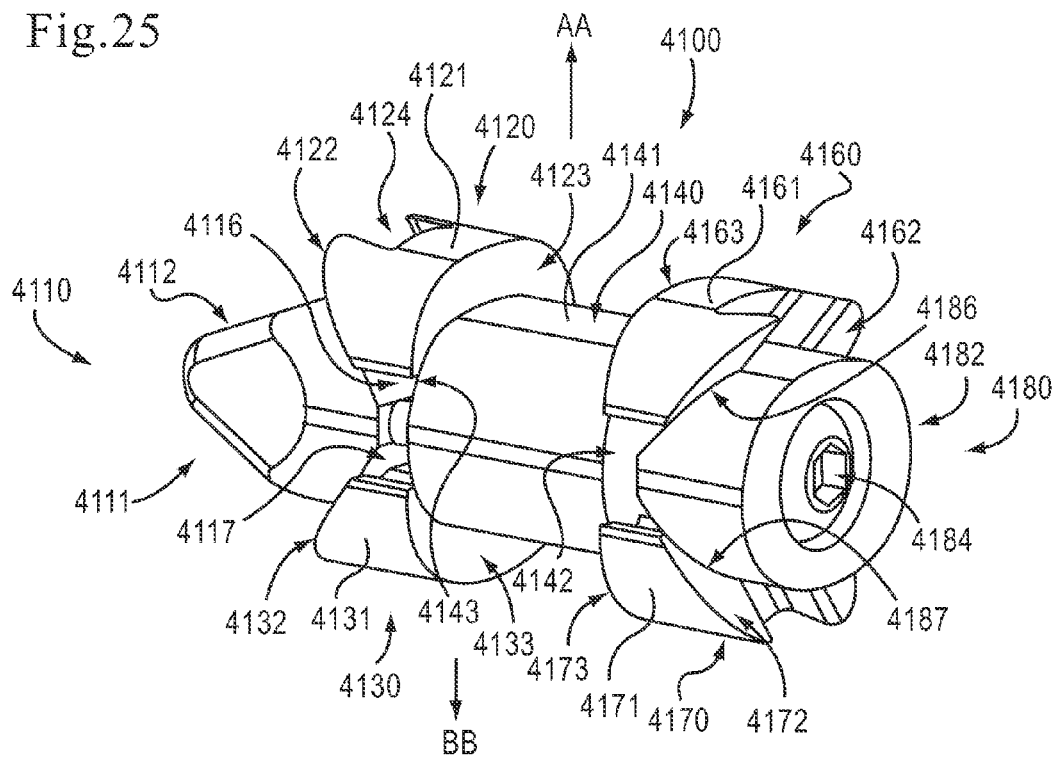
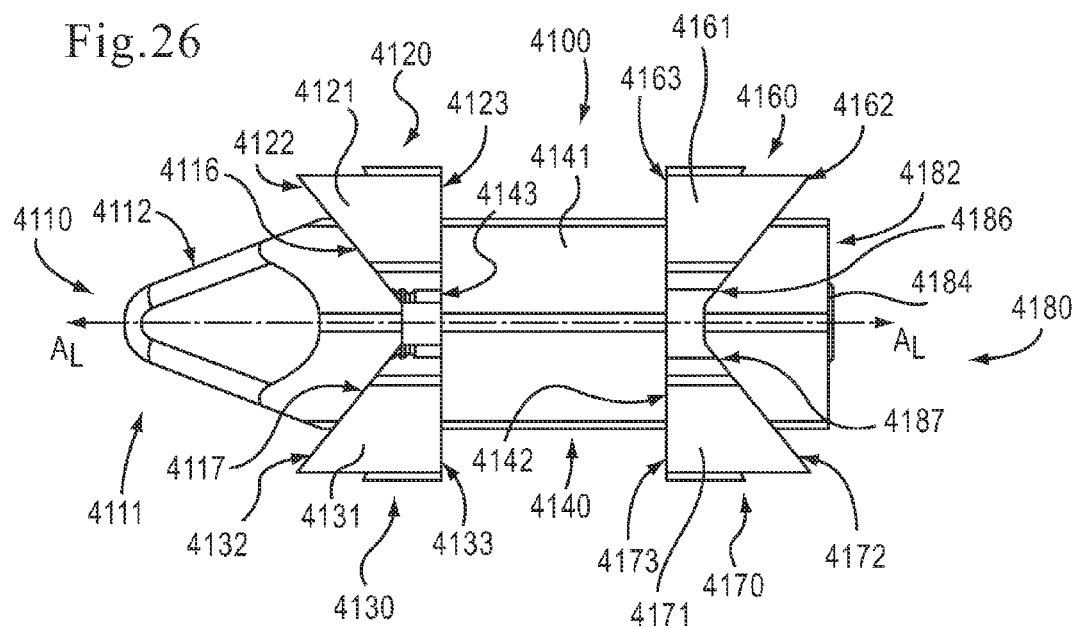

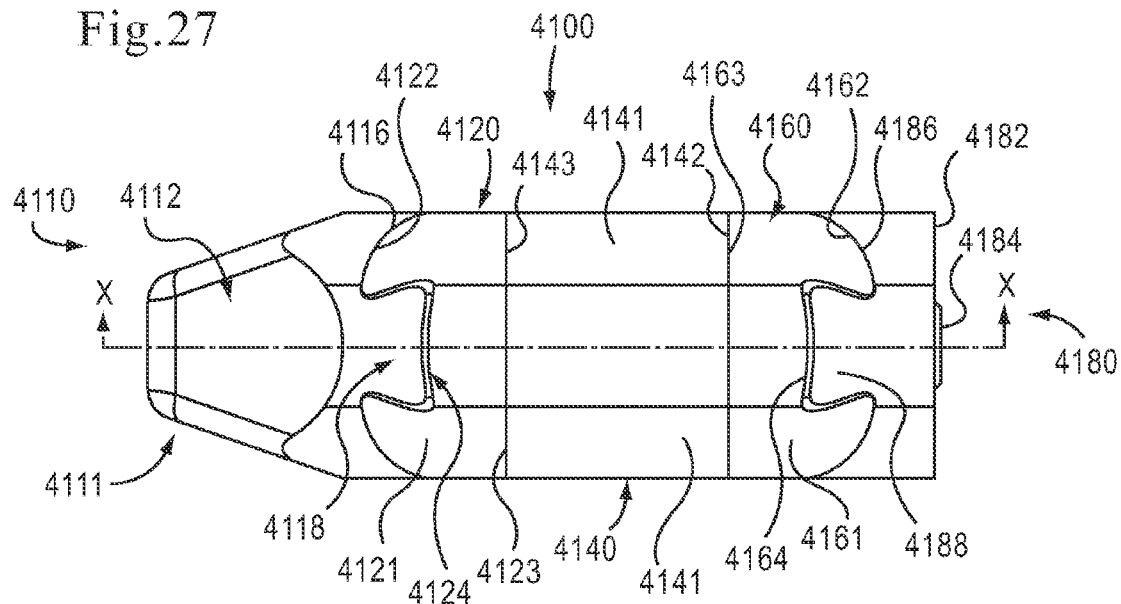
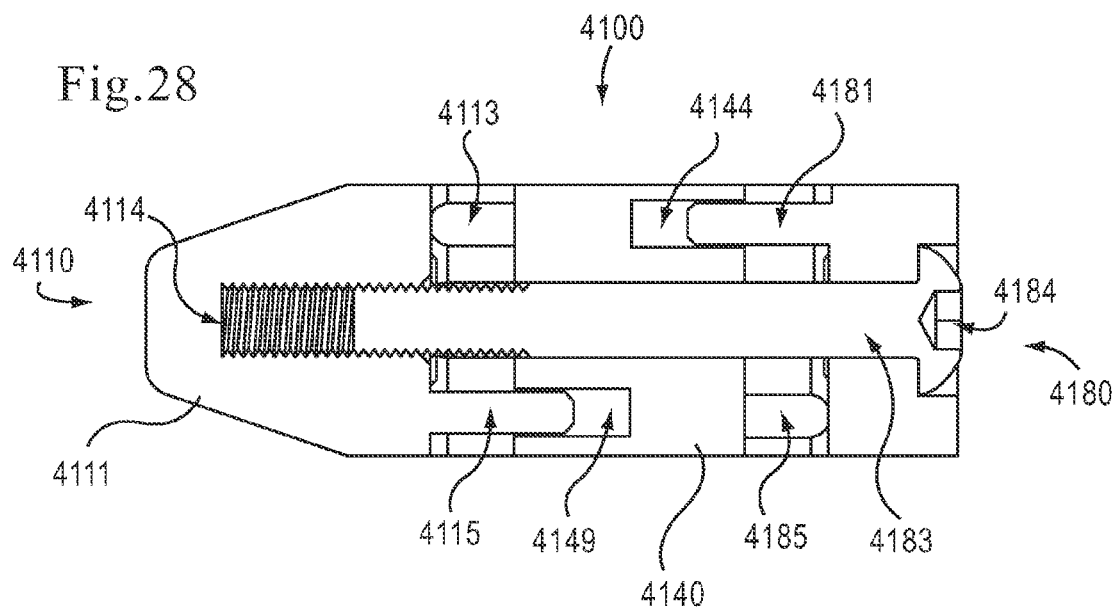

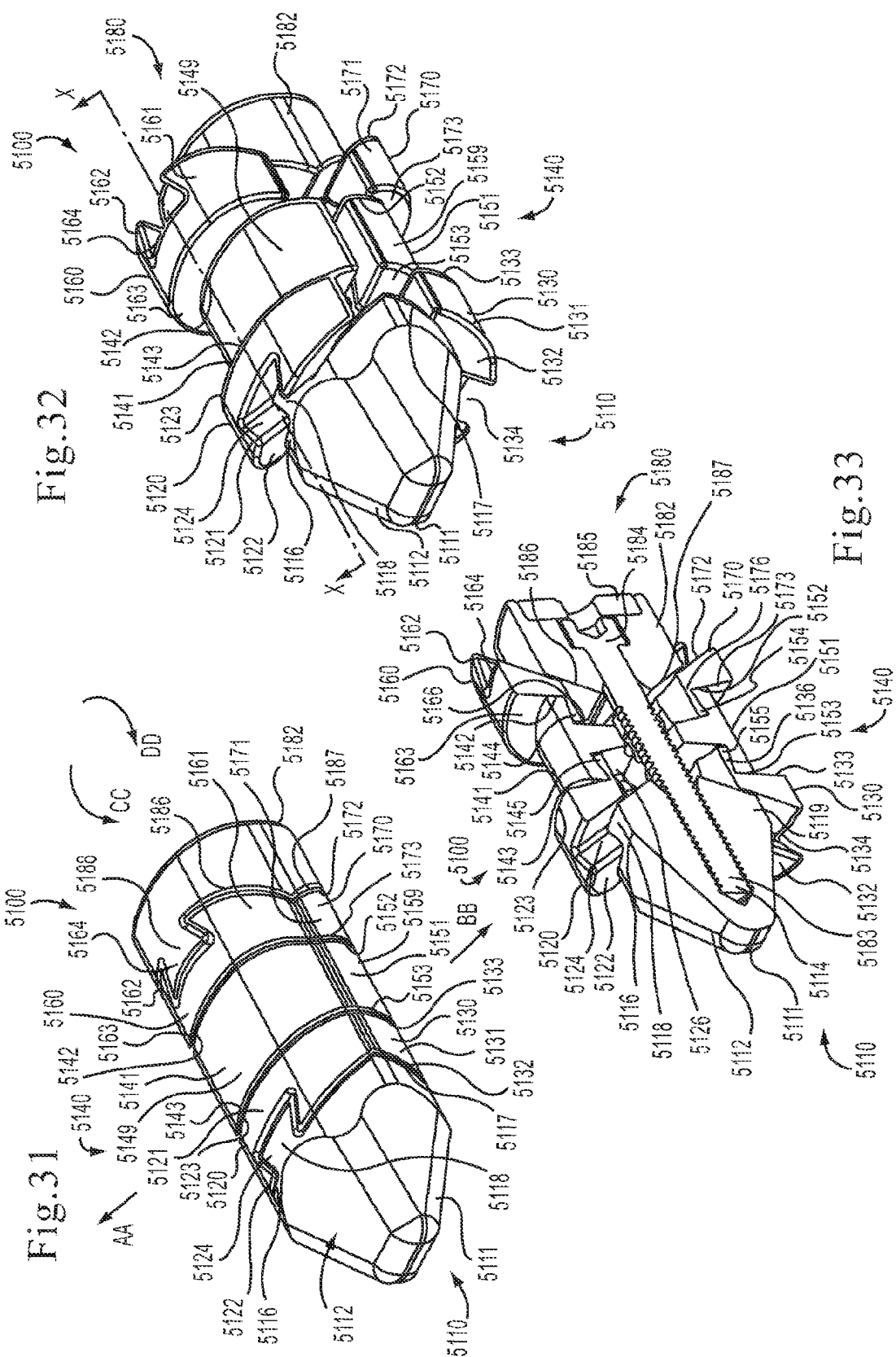

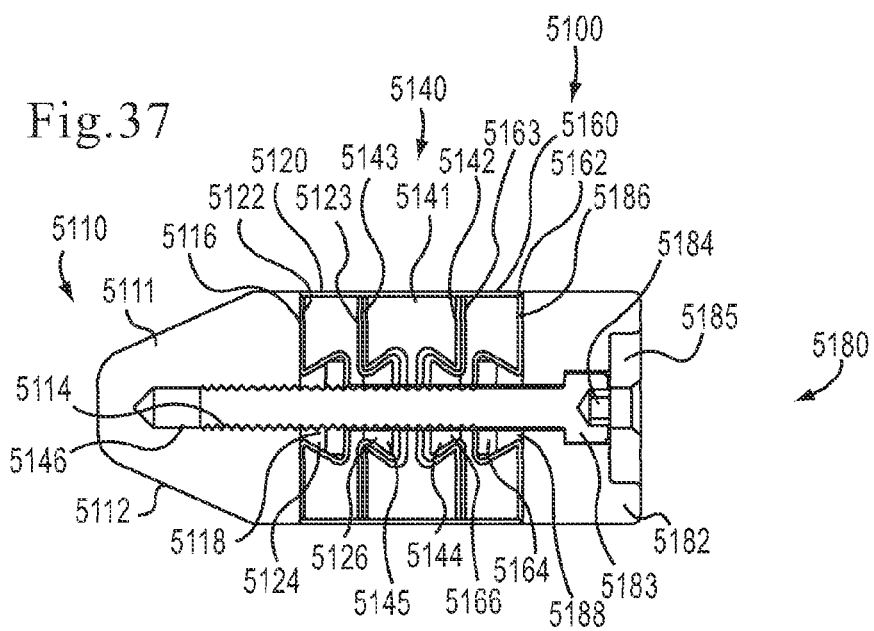
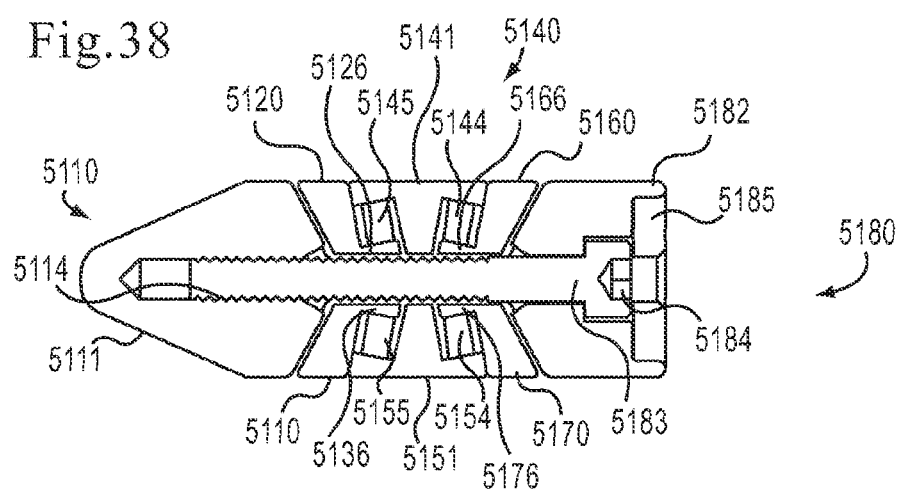
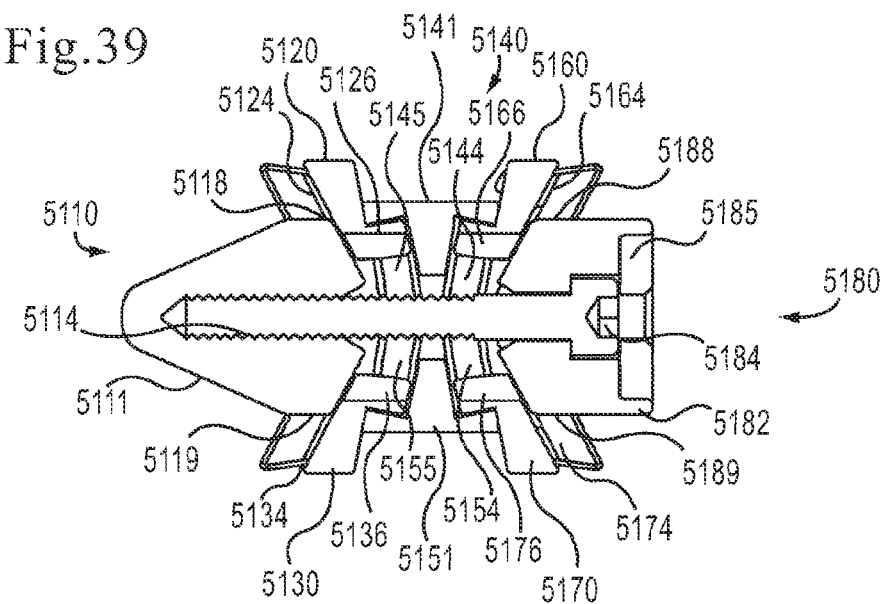

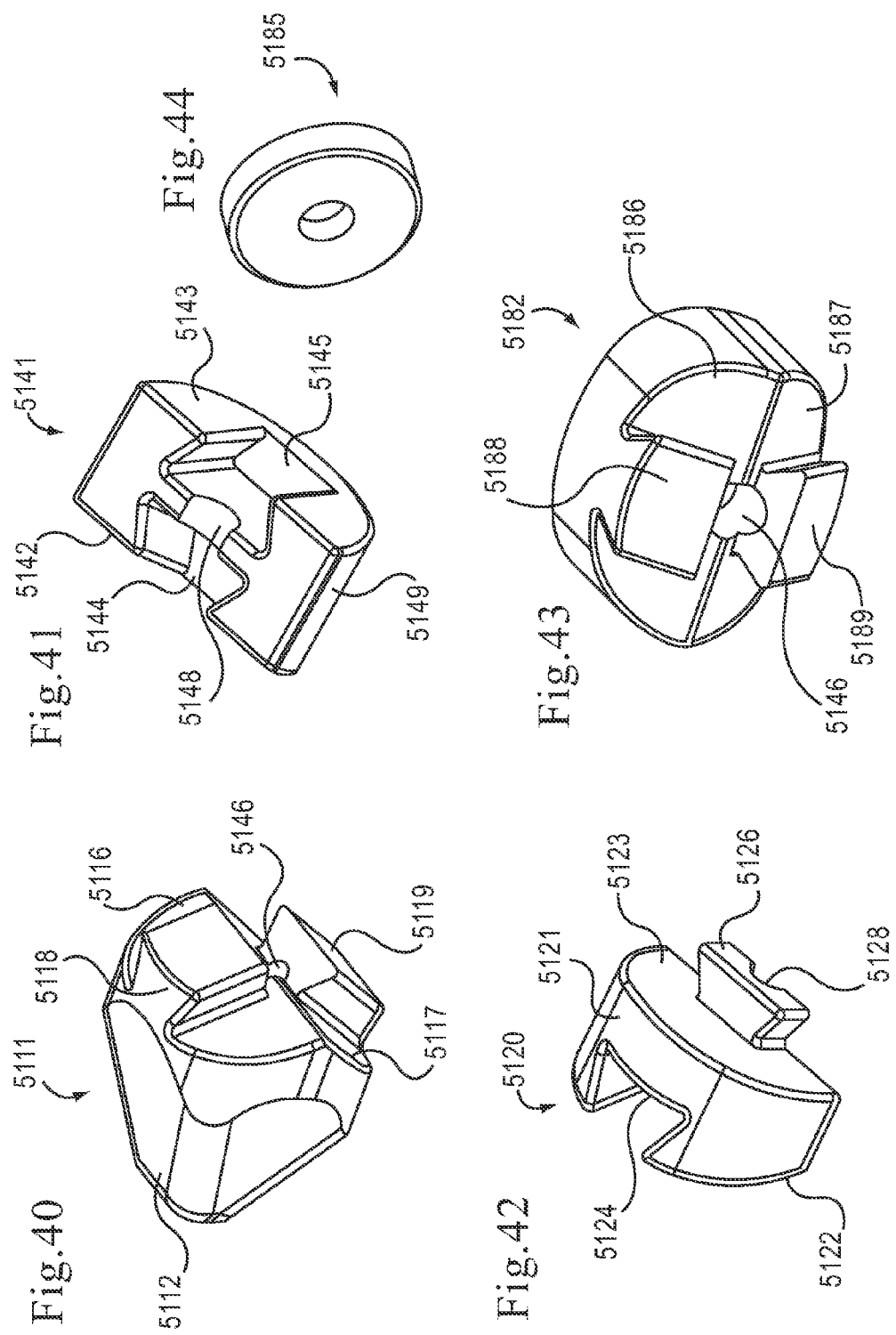

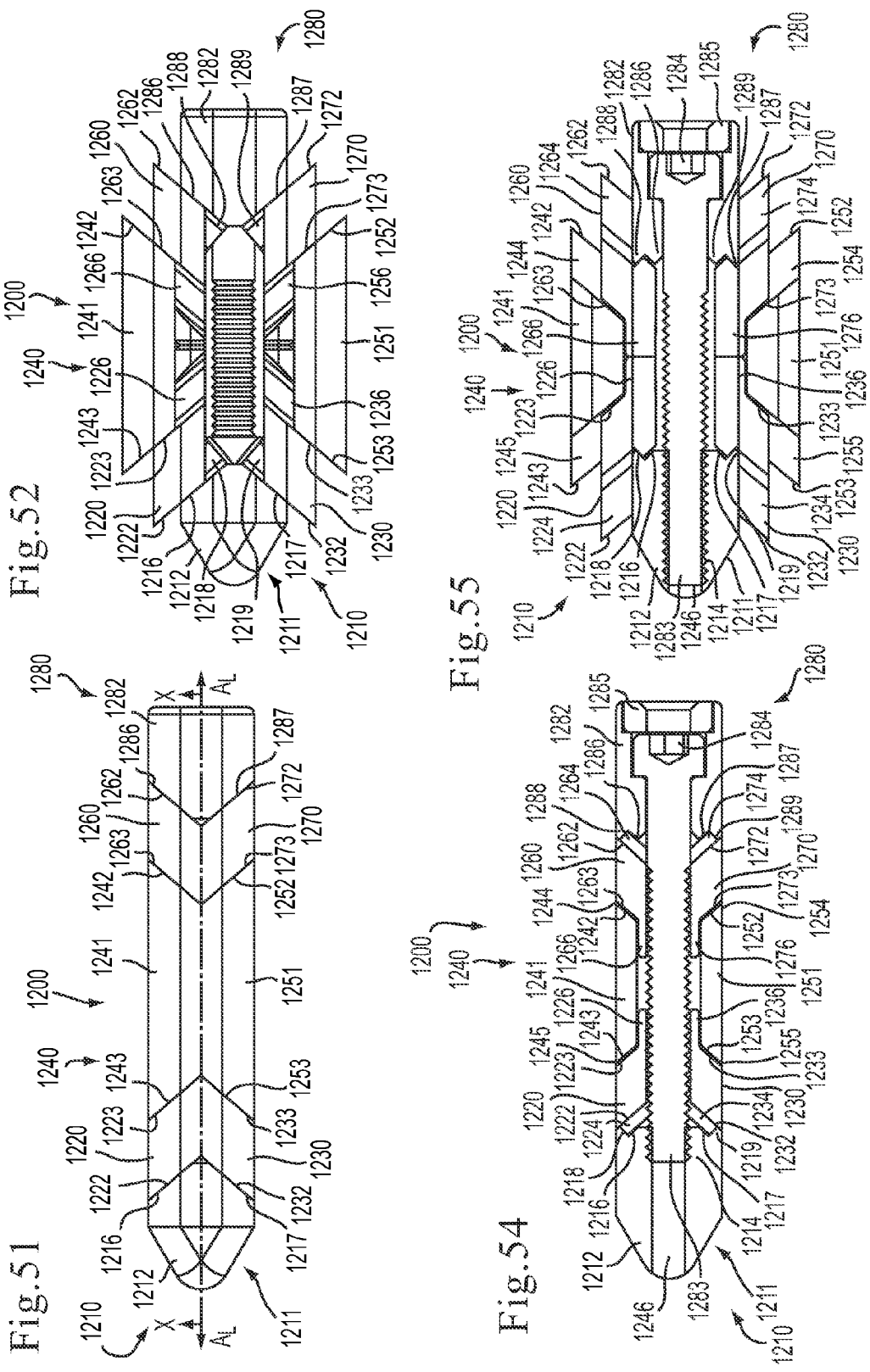

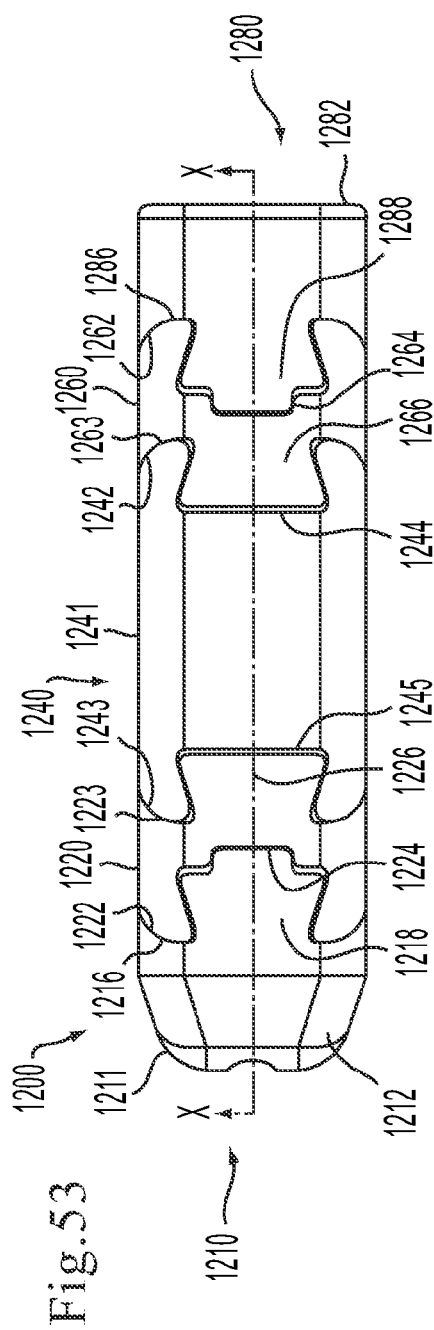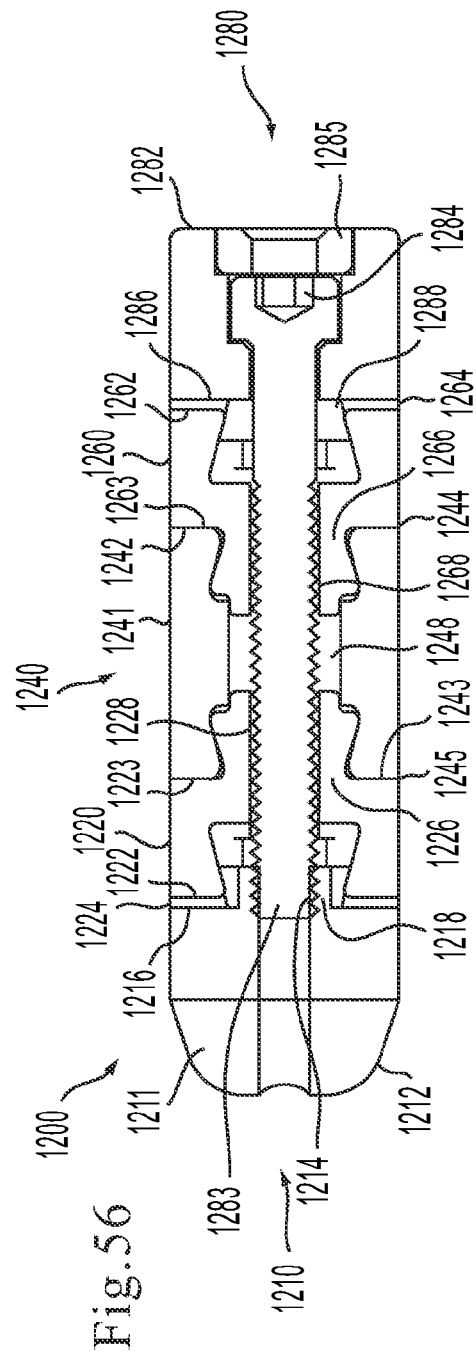

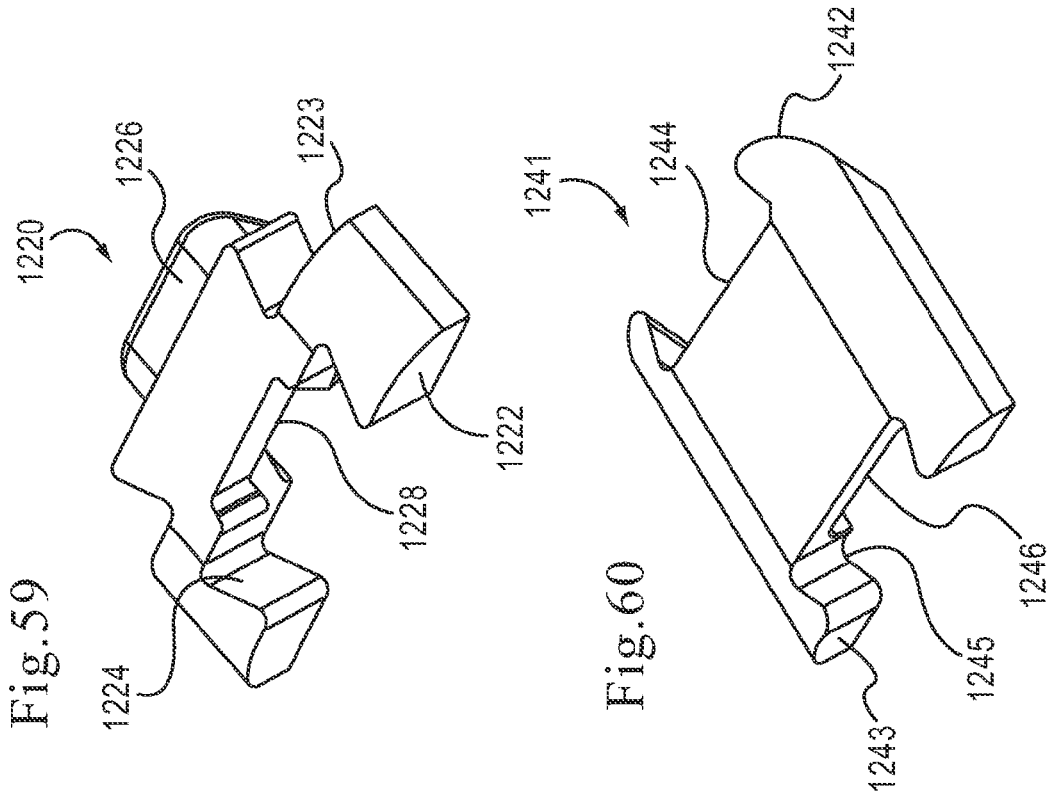
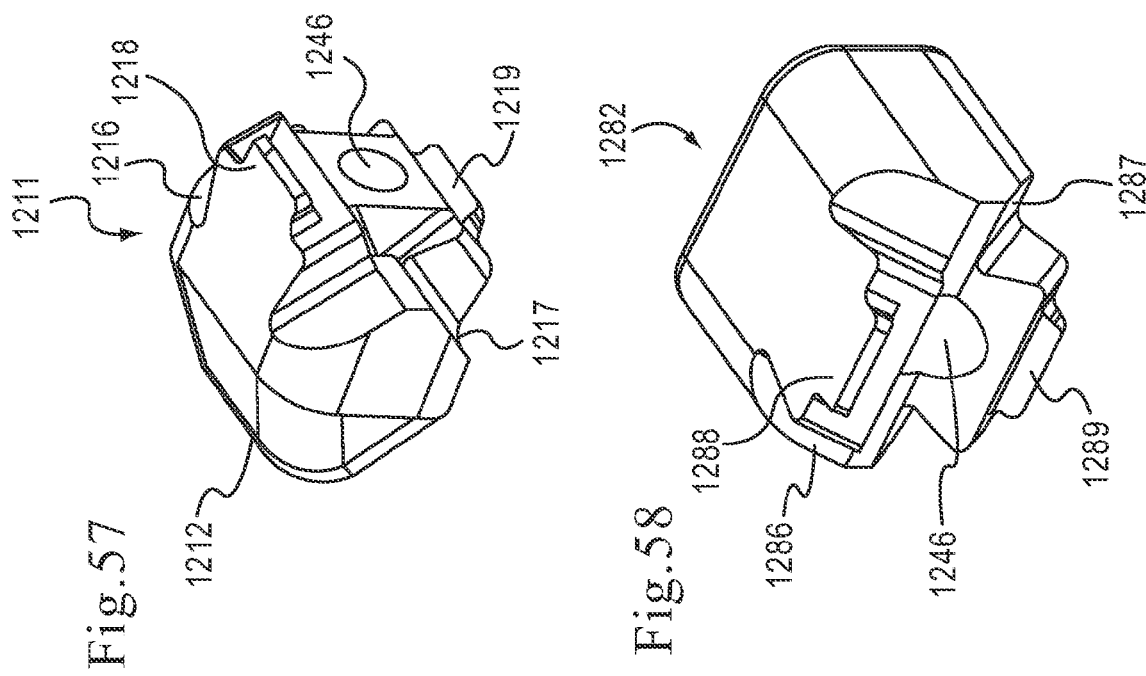

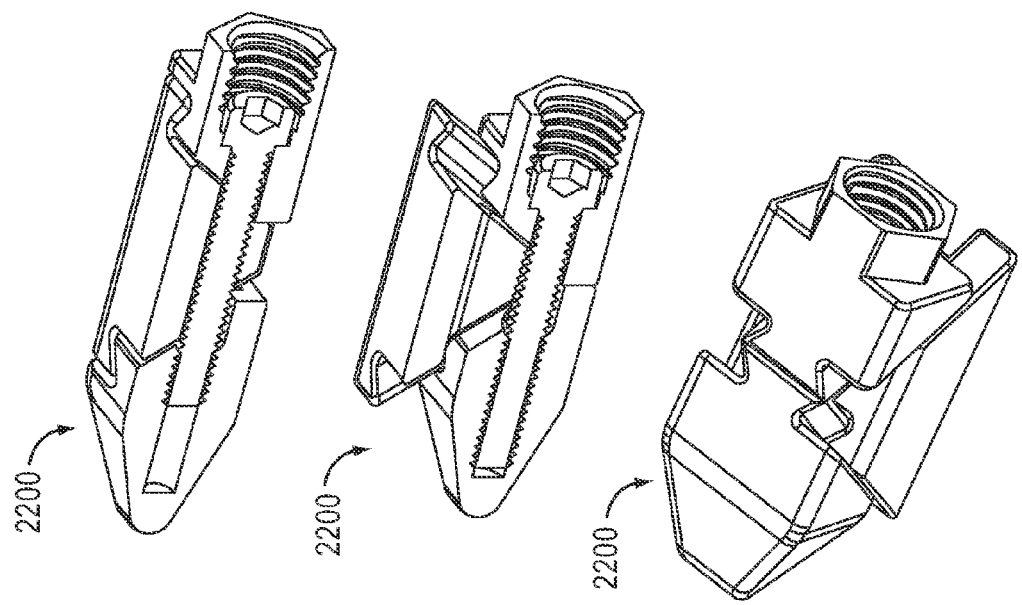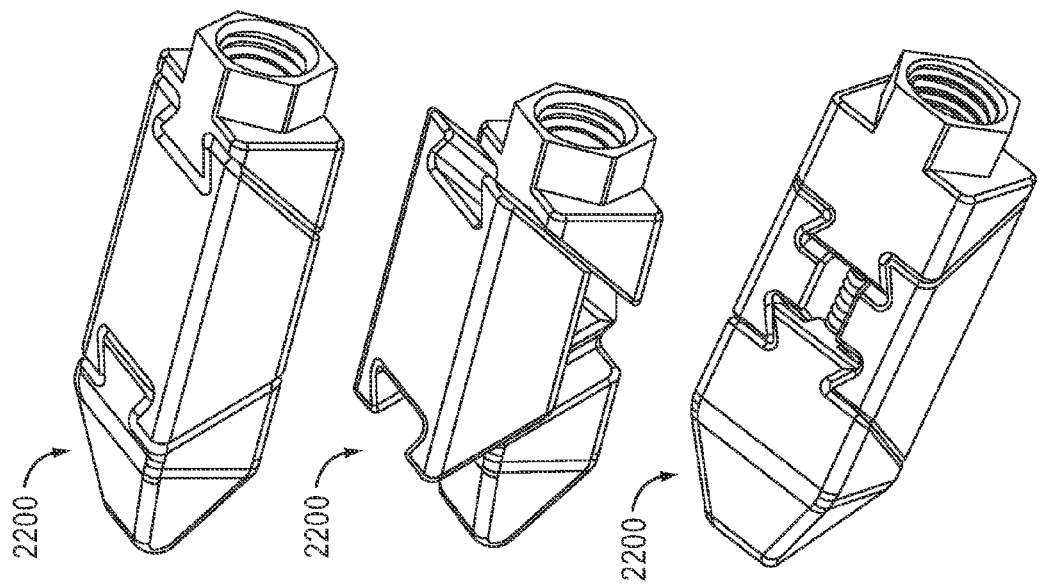
Fig.61

MEDICAL IMPLANTS AND METHODS

CROSS-REFERENCE TO RELATED APPLICATIONS

This application claims priority to U.S. Provisional Application Ser. No. 61/025,991, entitled "Medical Implants and Methods," filed Feb. 4, 2008, which is incorporated herein by reference in its entirety.

This application is related to U.S. patent application Ser. No. 12/182,437, entitled "Medical Implants and Methods," Ser. No. 12/182,425, entitled "Tools and Methods for Insertion and Removal of Medical Implants," and Ser. No. 12/182,431, entitled "Spine Distraction Tools and Methods of Use," each of which is filed herewith, and each of which is incorporated herein by reference in its entirety.

BACKGROUND

The invention relates generally to the treatment of spinal conditions, and more particularly, to the treatment of spinal compression using percutaneous spinal implants for implantation between adjacent spinous processes and/or percutaneous spinal implants for implantation in a space associated with an intervertebral disc.

Minimally-invasive procedures have been developed to provide access to the space between adjacent spinous processes such that major surgery is not required. Such known procedures, however, may not be suitable in conditions where the spinous processes are severely compressed. Moreover, such procedures typically involve large or multiple incisions. Further, some of the known implants configured to be inserted into a space associated with an intervertebral disc are non-expandable and involve an invasive open procedure.

Thus, a need exists for improvements in spinal implants for implantation between adjacent spinous processes. Additionally, a need exists for improvements in spinal implants for implantation in a space associated with an intervertebral disc. A further need exists for improvements in the tools used in placing spinal implants.

SUMMARY

Spinal implants and methods are described herein. In some embodiments, an apparatus includes a spacer, a proximal retention member, a distal retention member, and an actuator. The spacer defines a longitudinal axis and includes a proximal surface and a distal surface opposite the proximal surface. The spacer is configured to engage a first spinous process and a second spinous process. The proximal retention member is coupled to the spacer such that a portion of the proximal retention member is in contact with the proximal surface of the spacer. The distal retention member includes a first surface and a second surface. The distal retention member is movably coupled to the spacer such that the second surface is in contact with the distal surface of the spacer. An axis within a plane defined by the first surface of the distal retention member is non-parallel to and non-normal to the longitudinal axis defined by the spacer. The actuator is movably coupled to the spacer and is configured to move relative to the spacer along the longitudinal axis defined by the spacer. The actuator includes an actuation surface that is slidably coupled to and substantially parallel to the first surface of the distal retention member.

BRIEF DESCRIPTION OF THE DRAWINGS

FIGS. 20 and 21 are exploded views of the implant illustrated in FIGS. 14-19.

FIGS. 24 and 25 are perspective views of an implant, according to an embodiment in a first configuration and a second configuration, respectively.

FIG. 26 is a side view of the implant shown in FIG. 25 in the second configuration.

FIG. 27 is a top view of the implant shown in FIG. 24 in the first configuration.

FIG. 28 is a cross-sectional view of the implant shown in FIG. 24, taken along line X-X in FIG. 24.

FIGS. 31 and 32 are perspective views of an implant, according to an embodiment in a first configuration and a second configuration, respectively.

FIG. 33 is a cross-sectional view of the implant shown in FIG. 32 in the second configuration, taken along line X-X in FIG. 32.

FIG. 37 is a cross-sectional view of the implant shown in FIG. 35, taken along line Y-Y in FIG. 35.

FIG. 38 is a cross-sectional view of the implant shown in FIG. 34 in the first configuration, taken along line X-X in FIG. 34.

FIG. 39 is a cross-sectional view of the implant shown in FIG. 38 in the second configuration.

FIG. 40 is a perspective view of an insertion member of the implant shown in FIG. 31.

FIG. 41 is a perspective view of a support member of the implant shown in FIG. 31.

FIG. 42 is a perspective view of a retention member of the implant shown in FIG. 31.

FIG. 43 is a perspective view of a tool engagement member of the implant shown in FIG. 31.

FIG. 44 is a perspective view of a cap of the implant shown in FIG. 31.

FIG. 51 is a side view of the implant shown in FIG. 47 in the first configuration.

FIG. 52 is a side view of the implant shown in FIG. 48 in the second configuration.

FIG. 53 is a top view of the implant shown in FIG. 47 in the first configuration.

FIG. 54 is a cross-sectional view of the implant shown in FIG. 53 in the first configuration, taken along line X-X in FIG. 53.

FIG. 55 is a cross-sectional view of the implant shown in FIG. 54 in the second configuration.

FIG. 56 is a cross-sectional view of the implant shown in FIG. 51 in the first configuration, taken along line X-X in FIG. 51.

FIG. 57 is a perspective view of an insertion member of the implant shown in FIG. 47.

FIG. 58 is a perspective view of a tool engagement member of the implant shown in FIG. 47.

FIG. 59 is a perspective view of an intermediate member of the implant shown in FIG. 47.

FIG. 60 is a perspective view of a central support member of the implant shown in FIG. 47.

FIGS. 61-63 show various views of an implant according to an embodiment.

DETAILED DESCRIPTION

Figure 1:
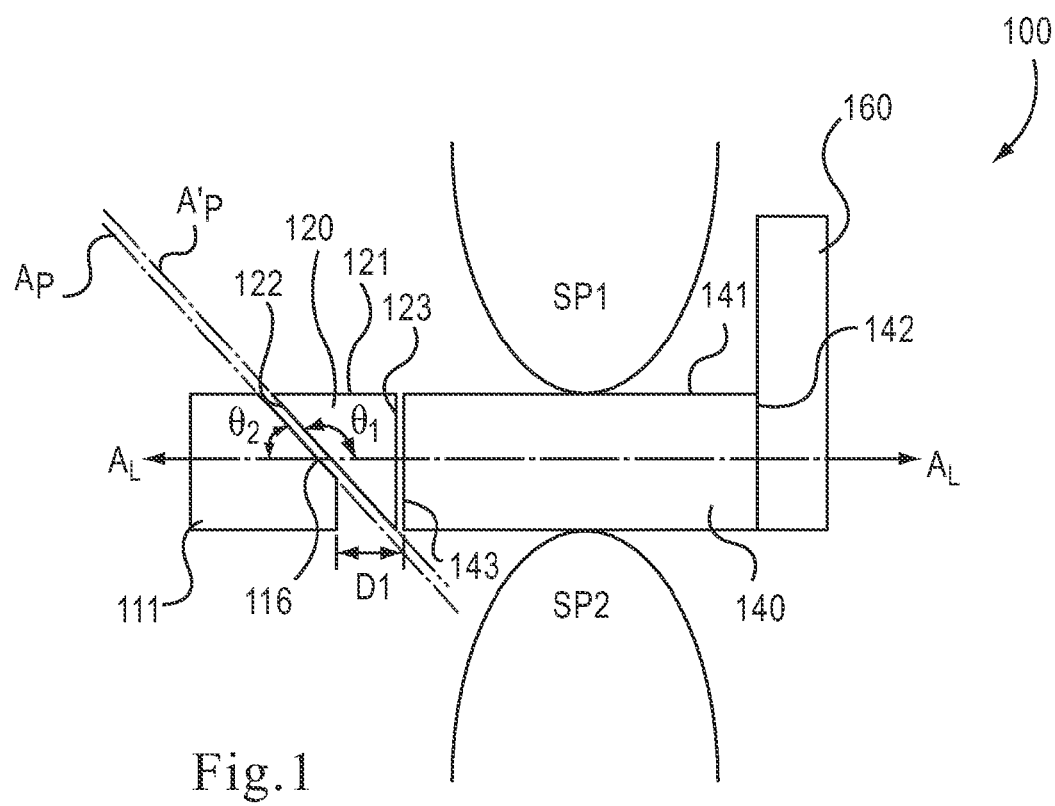
FIGS. 1 and 2 are schematic illustrations of an implant, according to an embodiment in a first configuration and a second configuration, respectively.

In some embodiments, an apparatus includes a spacer, a proximal retention member, a distal retention member, and an actuator. The spacer defines a longitudinal axis and includes a proximal surface and a distal surface opposite the proximal surface. The spacer is configured to engage a first spinous process and a second spinous process. The proximal retention member is coupled to the spacer such that a portion of the proximal retention member is in contact with the proximal surface of the spacer. The distal retention member includes a first surface and a second surface. The distal retention member is movably coupled to the spacer such that the second surface is in contact with the distal surface of the spacer. An axis within a plane defined by the first surface of the distal retention member is non-parallel to and non-normal to the longitudinal axis defined by the spacer. The actuator is movably coupled to the spacer and is configured to move relative to the spacer along the longitudinal axis defined by the spacer. The actuator includes an actuation surface that is slidably coupled to and substantially parallel to the first surface of the distal retention member.

In some embodiments, an apparatus includes an interspinous process implant. The interspinous process implant includes a central body, a proximal retention member, and a distal retention member, and defines a longitudinal axis. The central body includes a proximal surface, a distal surface and an outer surface. The proximal retention member has an engagement surface and an outer surface. The proximal retention member is movably coupled to the central body such that the engagement surface of the proximal retention member is slidably coupled to the proximal surface of the central body. The distal retention member has an engagement surface and an outer surface. The distal retention member is movably coupled to the central body such that the engagement surface of the distal retention member is slidably coupled to the distal surface of the central body. The interspinous process implant can be moved between a first configuration and a second configuration. The outer surface of the central body, the outer surface of the proximal retention member and the outer surface of the distal retention member are substantially aligned when the interspinous process implant is in the first configuration. The outer surface of the central body, a portion of the engagement surface of the proximal retention member and a portion of the engagement surface of the distal retention member collectively form a saddle when the interspinous process implant is in the second configuration. The saddle is configured to receive a spinous process.

In some embodiments, an apparatus includes a spacer, a proximal retention member, a distal retention member, and an actuator. The spacer has a proximal surface and a distal surface opposite the proximal surface, and defines a longitudinal axis. The spacer is configured to engage a spinous process. The proximal retention member is coupled to the spacer such that a portion of the proximal retention member is in contact with the proximal surface of the spacer. The distal retention member includes a surface that defines a dovetail groove. The distal retention member is movably coupled to the spacer such that a portion of the distal retention member is in contact with the distal surface of the spacer. The actuator is movably coupled to the spacer and has an actuation surface having a dovetail protrusion. The dovetail protrusion of the actuation surface of the actuator is configured to be matingly received within the dovetail groove defined by the surface of the distal retention member.

In some embodiments, an apparatus includes a spacer, a first retention member, a second retention member and an actuator. The spacer includes a surface and defines a longitudinal axis. The spacer is configured to engage a spinous process. The first retention member has a first surface and a second surface. The first retention member is movably coupled to the spacer such that the second surface of the first retention member is slidably coupled to the surface of the spacer. An axis within a plane defined by the first surface of the first retention member is non-parallel to and non-normal to the longitudinal axis defined by the spacer. The second retention member includes a first surface and a second surface. The second retention member is movably coupled to the spacer such that the second surface of the second retention member is slidably coupled to the surface of the spacer. The actuator is movably coupled to the spacer and includes a tapered portion having a first actuation surface and a second actuation surface. The first actuation surface is slidably coupled to and substantially parallel to the first surface of the first retention member. The second actuation surface is slidably coupled to and substantially parallel to the first surface of the second retention member.

In some embodiments, an apparatus includes a spacer, a retention assembly and an actuator. The spacer is configured to engage adjacent spinous processes. The spacer has a first size along an axis normal to a longitudinal axis of the spacer when in a first configuration and a second size along the axis normal to the longitudinal axis when in a second configuration. The second size of the spacer is greater than the first size of the spacer. The retention assembly includes a first surface and a second surface. The retention assembly has a first size along the axis normal to the longitudinal axis of the spacer when in a first configuration and a second size along the axis normal to the longitudinal axis when in a second configuration. The second size of the retention assembly is greater than the first size of the retention assembly. The retention assembly is movably coupled to the spacer such that the second surface of the retention assembly is in contact with a surface of the spacer. An axis within a plane defined by the first surface of the retention assembly is non-parallel to and non-normal to the longitudinal axis of the spacer. The actuator is movably coupled to the spacer and includes an actuation surface slidably coupled to and substantially parallel to the first surface of the retention assembly. The actuator is configured to move the retention assembly between its first configuration and its second configuration. Further, the actuator is configured to move the spacer between its first configuration and its second configuration.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

The term "parallel" is used herein to describe a relationship between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The term "normal" is used herein to describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal to a curved surface when the line and an axis tangent to the curved surface intersect at an angle of approximately 90 degrees within a plane. Two geometric constructions are described herein as being "normal" or "substantially normal" to each other when they are nominally normal to each other, such as for example, when they are normal to each other within a tolerance. Such tolerances can include, for example, manufacturing tolerances, measurement tolerances or the like.

It should be understood that the references to geometric constructions are for purposes of discussion and illustration. The actual structures may differ from geometric ideal due to tolerances and/or other minor deviations from the geometric ideal.

Figure 2:
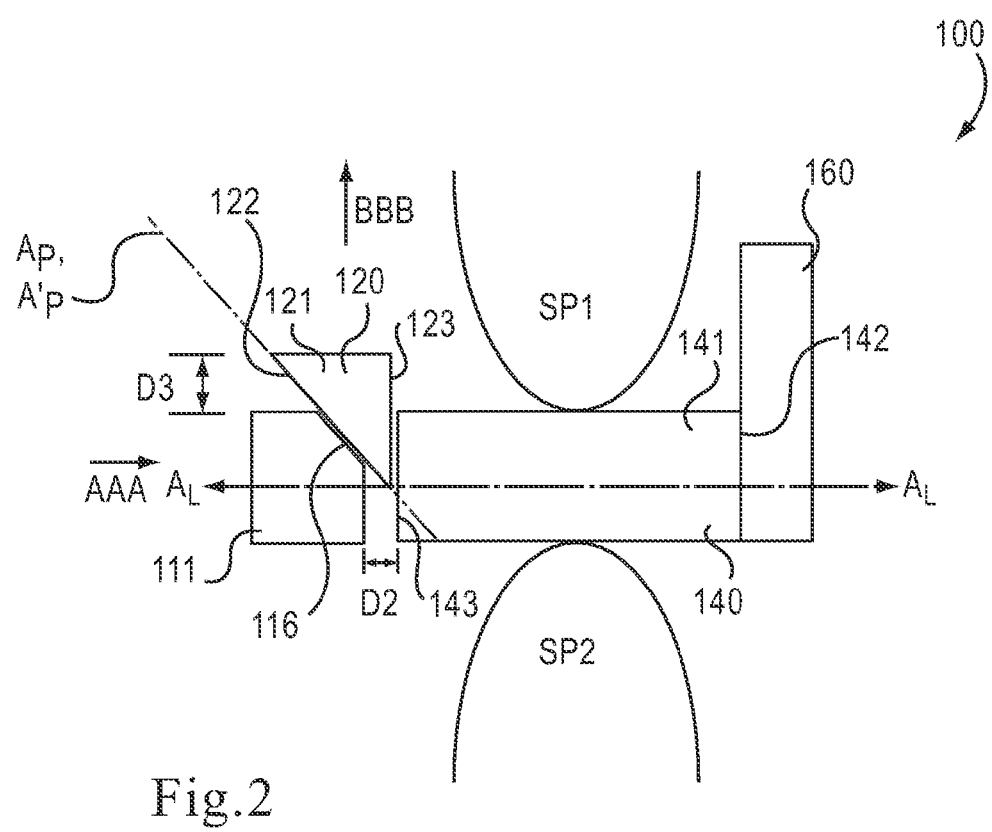

FIGS. 1 and 2 are schematic illustrations of an implant 100, according to an embodiment, in a first configuration and a second configuration, respectively. Implant 100 includes a spacer 140, a proximal retention member 160, a distal retention member 120, and an actuator 111. The spacer 140 of the implant 100 includes a proximal surface 142, a distal surface 143, and an outer surface 141, and defines a longitudinal axis $A_L$. At least a portion of the implant 100 is configured to be disposed in a space between a first spinous process SP1 and a second spinous process SP2 such that the spacer 140 of the implant 100 engages the first spinous process SP1 and the second spinous process SP2 during spinal extension, either directly or through surrounding tissue. Said another way, at least during spinal extension, the outer surface 141 of the spacer 140 is configured to directly engage and/or contact the spinous processes SP1, SP2 and/or the bodily tissue surrounding the spinous processes SP1, SP2 without any intervening structure associated with the implant 100. In some embodiments, for example, a portion of the spacer 140 is disposed within an opening defined in the interspinous ligament (not shown). In this manner, the spacer 140 can contact the spinous processes SP1, SP2 through the interspinous ligament. For purposes of clarity, however, the tissue surrounding the spinous processes SP1, SP2 is not illustrated.

The proximal retention member 160 of the implant 100 is coupled to the spacer 140 such that at least a portion of the proximal retention member 160 is adjacent the proximal surface 142 of the spacer 140. In some embodiments, a portion of the proximal retention member 160 can be in contact with the proximal surface 142 of the spacer 140. In other embodiments, the proximal retention member 160 can be spaced apart from the proximal surface 142 of the spacer 140. In some embodiments, the proximal retention member 160 can be movably coupled to the spacer 140. In other embodiments, the proximal retention member 160 can be removably coupled to the spacer 140.

The distal retention member 120 of the implant 100 is movably coupled to the spacer 140, and includes a first surface 122, a second surface 123, and an outer surface 121. An axis $A_p$ within a plane defined by the first surface 122 of the distal retention member 120 is non-parallel to and non-normal to the longitudinal axis $A_L$. Said another way, the first surface 122 of the distal retention member 120 is angularly offset from the longitudinal axis $A_L$ by an angle $\theta_1$. The angle $\theta_1$, which is defined by the first surface 122 of the distal retention member 120 and the longitudinal axis $A_L$, is supplementary to the angle $\theta_2$, which is defined by the actuation surface 116 of the actuator 111 and the longitudinal axis $A_L$, as further described herein. Moreover, the first surface 122 of the distal retention member 120 is substantially parallel to the actuation surface 116 of the actuator 111.

The distal retention member 120 is coupled to the spacer 140 such that the second surface 123 of the distal retention member 120 is in contact with the distal surface 143 of the spacer 140. As shown in FIGS. 1 and 2, the second surface 123 of the distal retention member 120 is substantially normal to the longitudinal axis $A_L$. Moreover, the second surface 123 of the distal retention member 120 is substantially parallel to the distal surface 143 of the spacer 140. Said another way, the second surface 123 of the distal retention member 120 defines an angle with respect to the longitudinal axis $A_L$ that is supplementary to an angle defined by the distal surface 143 of the spacer 140 with respect to the longitudinal axis $A_L$.

The actuator 111 of the implant 100 is movably coupled to the spacer 140, and includes an actuation surface 116. The actuation surface 116 is slidably coupled to and substantially parallel to the first surface 122 of the distal retention member 120. Said another way, the axis A'p is within a plane defined by the actuation surface 116 of the actuator 111. As shown in FIG. 1, the actuation surface 116 of the actuator 111 is angularly offset from the longitudinal axis $A_L$ by an angle $\theta_2$. The angle $\theta_2$, which is defined by the actuation surface 116 of the actuator 111 and the longitudinal axis $A_L$, is supplementary to the angle $\theta_1$, as described above.

As shown in FIGS. 1 and 2, the implant 100 is movable between a first configuration (FIG. 1) and a second configuration (FIG. 2). When the implant 100 is in the first configuration, the actuator 111 is spaced apart from the distal surface 143 of the spacer 140 along the longitudinal axis $A_L$ by a non-zero distance D1. When the implant 100 is in the first configuration, the outer surface 121 of the distal retention member 120 is substantially aligned with the outer surface 141 of the spacer 140. Said another way, the outer surface 121 of the distal retention member 140 and the outer surface 141 of the spacer 140 form a substantially continuous surface. Said yet another way, the outer surface 121 of the distal retention member 120 is substantially flush with the outer surface 141 of the spacer 140. Said still another way, the second surface 123 of the distal retention member 120 and the distal surface 143 of the spacer 140 are aligned.

To move the implant 100 to the second configuration, the actuator 111 is moved along the longitudinal axis $A_L$ in the direction shown by the arrow AAA in FIG. 2. Movement of the actuator 111 causes the actuation surface 116 of the actuator 111 to exert an axial force on the first surface 122 of the distal retention member 120. Because the actuation surface 116 of the actuator 111 is at an angle $\theta_2$ with respect to the longitudinal axis $A_L$, a component of the axial force transmitted via the actuation surface 116 to the first surface 122 of the distal retention member 120 has a direction as shown by the arrow BBB in FIG. 2. Said another way, a component of the force exerted by the actuator 111 on the distal retention member 120 has a direction that is substantially normal to the longitudinal axis $A_L$. Accordingly, the force exerted by the actuator 111 on the distal retention member 120 causes the first surface 122 of the distal retention member 120 to slide on the actuation surface 116 of the actuator 111, and causes the distal retention member 120 to move in the direction shown by the arrow BBB in FIG. 2.

As shown in FIG. 2, when the implant 100 is in the second configuration, the actuator 111 is spaced apart from the distal surface 143 of the spacer 140 along the longitudinal axis $A_L$ by a non-zero distance D2, which is less than the distance D1. Although shown in FIG. 2 as being spaced apart by the distance D2, in other embodiments, the actuator 111 can be in contact with the distal surface 143 of the spacer 140 when the implant 100 is in the second configuration. In such embodiments, after the actuator 111 moves a predetermined distance along the longitudinal axis $A_L$, the actuator 111 can contact the distal surface 143 of the spacer 140, limiting the range of motion of the actuator 111 relative to the spacer 140.

When the implant 100 is in the second configuration, the distal retention member 120 is offset from the spacer 140 in a direction substantially normal to the longitudinal axis $A_L$, as shown by the arrow BBB in FIG. 2. Said another way, the outer surface 121 of the distal retention member 120 is not aligned with the outer surface 141 of the spacer 140 and is discontinuous with the outer surface 141 of the spacer 140. Said yet another way, the outer surface 121 of the distal retention member 120 is spaced apart from the outer surface 141 of the spacer 140 by a non-zero distance D3. In this manner, the distal retention member 120, the proximal retention member 160 and the spacer 140 form a saddle, as further described herein.

The angle $\theta_1$ of the first surface 122 of the distal retention member 120 and the angle $\theta_2$ of the actuation surface 116 of the actuator 120 can be any suitable angle. The value of the angles $\theta_1$ and $\theta_2$ can influence the force to move the implant 100 from the first configuration to the second configuration and/or the axial distance through which the actuator 111 travels when the implant 100 is moved from the first configuration to the second configuration. More particularly, if the angle $\theta_1$ is close to 180 degrees (e.g., between 165 and 180 degrees) and the angle $\theta_2$ is close to 0 degrees (e.g., between 0 and 15 degrees), the force to move the implant 100 from the first configuration to the second configuration will be less than the force needed if the angle $\theta_1$ and the angle $\theta_2$ are both close to 90 degrees. Said another way, when the first surface 122 of the distal retention member 120 and the actuation surface 116 of the actuator 111 are close to being parallel to the longitudinal axis $A_L$, less force is needed to move the implant 100 to the second configuration than when the first surface 122 of the distal retention member 120 and the actuation surface 116 of the actuator 111 are close to being normal to the longitudinal axis. If the angle $\theta_1$ is close to 180 degrees and the angle $\theta_2$ is close to 0 degrees, however, the distance the actuator 111 travels along the longitudinal axis $A_L$ to move the implant 100 from the first configuration to the second configuration to achieve the desired offset of the retention member 120 (e.g., D3), will be greater than the distance the actuator 111 travels if the angle $\theta_1$ and the angle $\theta_2$ are both close to 90 degrees.

In use, the implant 100 can be inserted between a first spinous process SP1 and a second spinous process SP2 when the implant 100 is in the first configuration (see e.g., FIG. 1). For example, a medical practitioner can insert the implant 100 percutaneously into a body of a patient. In some embodiments, the implant 100 can be inserted percutaneously via a cannula. In some embodiments, a tool, such as those described in U.S. patent application Ser. No. 12/182,425 entitled "Tools and Methods for Insertion and Removal of Medical Implants," which is incorporated herein by reference in its entirety, can be used to insert the implant 100 into a body of a patient.

After the implant 100 is between the first spinous process SP1 and the second spinous process SP2, the implant 100 can be moved from the first configuration to the second configuration (see e.g., FIG. 2). In some embodiments, the implant 100 can be actuated using a tool (not shown) configured to move the actuator 111 relative to the spacer 140 when the implant is within the body. Such tools can include, for example, those tools described in U.S. patent application Ser. No. 12/182,425 entitled "Tools and Methods for Insertion and Removal of Medical Implants," which is incorporated herein by reference in its entirety. As stated above, when the implant 100 is in the second configuration, the distal retention member 120, the proximal retention member 160 and the spacer 140 form a saddle, within which the first spinous process SP1 is disposed. In this manner, when the implant 100 is in the second configuration, the distal retention member 120 and the proximal retention member 160 can collectively limit movement of the spacer 140 with respect to the first spinous process SP1 along the longitudinal axis $A_L$.

A medical practitioner can remove the implant 100 from and/or reposition the implant 100 within the body. To remove from and/or reposition the implant 100 within the body, the implant 100 can be moved from the second configuration to the first configuration. This can be done by moving the actuator 111 in a direction opposite the direction shown by the arrow AAA in FIG. 2. This causes the implant 100 to return to the first configuration. After the implant 100 is in the first configuration, the medical practitioner can remove the implant 100 from and/or reposition the implant 100 within the body.

Although the distal surface 143 of the spacer 140 is shown and described as being substantially normal to the longitudinal axis $A_L$, in some embodiments, the distal surface 143 of the spacer 140 can be angularly offset from the longitudinal axis $A_L$. Said another way, in some embodiments, the proximal surface 142 of the spacer 140 and/or the distal surface 143 of the spacer 140 can define an angle with respect to the longitudinal axis $A_L$ that is not ninety degrees. For example, in some embodiments, the distal surface 143 of the spacer 140 can define an obtuse angle with respect to the longitudinal axis $A_L$, and the second surface 123 of the distal retention member 120 can define a supplementary acute angle with respect to the longitudinal axis $A_L$. In other embodiments, the distal surface 143 of the spacer 140 can define an acute angle with respect to the longitudinal axis $A_L$, and the second surface 123 of the distal retention member 120 can define a supplementary obtuse angle with respect to the longitudinal axis $A_L$. Such a non-normal arrangement of angles causes the distal retention member 120 to move in a direction substantially parallel to the distal surface 143 of the spacer 140 when the implant 100 is moved from the first configuration to the second configuration. Thus, the angle of the distal surface 143 of the spacer 140 affects the direction of movement of the distal retention member 120 when the implant 100 moves from the first configuration to the second configuration. In this manner, the distal retention member 120 can be configured to move in a direction non-normal to the longitudinal axis $A_L$. For example, in some embodiments, the distal retention member 120 can move distally (i.e., away from the spinous process SP1) relative to the spacer 111 when the implant 100 moves from the first configuration to the second configuration. In other embodiments, the distal retention member 120 can move proximally (i.e., towards the spinous process SP1) relative to the spacer 111 when the implant 100 moves from the first configuration to the second configuration. The proximal movement of the distal retention member 120 can be used, for example, to cause the distal retention member 120 to contact the spinous process SP1 when in the second configuration.

Although the outer surface 121 of the distal retention member 120 is shown and described as being substantially aligned with the outer surface 141 of the spacer 140 when the implant 100 is in the first configuration, in some embodiments, the outer surface 121 of the distal retention member 120 can be offset from the outer surface 141 of the spacer when the implant 100 is in the first configuration. Said another way, in some embodiments, the outer surface 121 of the distal retention member 120 can be discontinuous with the outer surface 141 of the spacer 140 when the implant 100 is in the first configuration. Said yet another way, in some embodiments, the outer surface 121 of the distal retention member 120 can be spaced apart from the outer surface 141 of the spacer 140 by a distance different than distance D3 (the distance the outer surface 121 of the distal retention member 120 is spaced apart from the outer surface 141 of the spacer 140 when the implant 100 is in the second configuration) when the implant 100 is in the first configuration.

Figure 3:
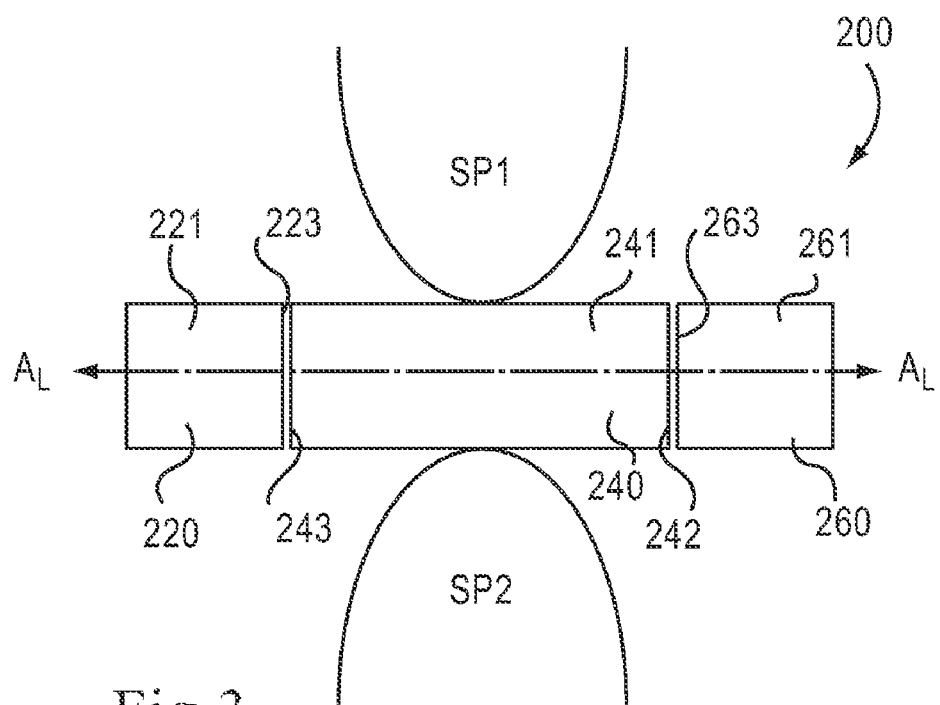
FIGS. 3 and 4 are schematic illustrations of an implant, according to an embodiment in a first configuration and a second configuration, respectively.
Figure 4:
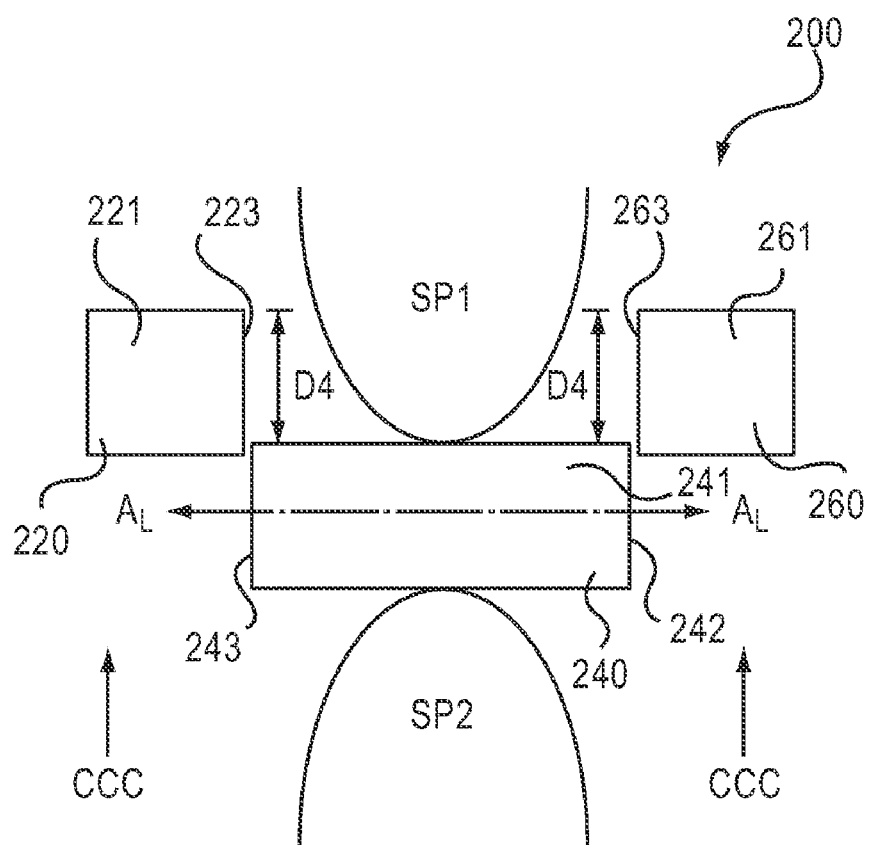

FIGS. 3 and 4 are schematic illustrations of an implant 200, according to an embodiment. The implant 200 includes a central body 240, a proximal retention member 260, and a distal retention member 220, and defines a longitudinal axis $A_L$. The central body 240 includes a proximal surface 242, a distal surface 243 and an outer surface 241. At least a portion of the central body 240 of implant 200 is configured to be disposed in a space between a first spinous process SP1 and a second spinous process SP2 such that the outer surface 241 of the central body 240 can engage a first spinous process SP1 and a second spinous process SP2, either directly or through surrounding tissue. Said another way, at least during spinal extension, the outer surface 241 of the central body 240 is configured to directly engage and/or contact the spinous processes SP1, SP2 and/or the bodily tissue surrounding the spinous processes SP1, SP2 without any intervening structure associated with the implant 200. In some embodiments, for example, a portion of the central body 240 is disposed within an opening defined in the interspinous ligament (not shown). In this manner, the central body 240 can contact the spinous processes SP1, SP2 through the interspinous ligament. For purposes of clarity, however, the tissue surrounding the spinous processes SP1, SP2 is not illustrated.

The proximal retention member 260 of the implant 200 includes an outer surface 261 and an engagement surface 263. The engagement surface 263 is substantially normal to the longitudinal axis $A_L$ and is slidably coupled to the proximal surface 242 of the central body 240. Accordingly, the proximal retention member 260 can translate relative to the central body 240 between a first position and a second position corresponding to a first configuration of the implant 200 and a second configuration of the implant 200, respectively, as described in further detail herein. The engagement surface 263 of the proximal retention member 260 is substantially parallel to the proximal surface 242 of the central body 240. Said another way, the angle that the engagement surface 263 defines with respect to the longitudinal axis $A_L$ is supplementary to the angle defined by the proximal surface 242 of the central body 240 with respect to the longitudinal axis $A_L$.

The distal retention member 220 of the implant 200 includes an outer surface 221 and an engagement surface 223. The engagement surface 223 is substantially normal to the longitudinal axis $A_L$ and is slidably coupled to the distal surface 243 of the central body 240. Accordingly, the distal retention member 220 can translate relative to the central body 240 between a first position and a second position corresponding to the first configuration of the implant 200 and the second configuration of the implant 200, respectively, as described in further detail herein. The engagement surface 223 of the distal retention member 220 is substantially parallel to the distal surface 243 of the central body 240. Said another way, the angle that the engagement surface 223 defines with respect to the longitudinal axis $A_L$ is supplementary to the angle defined by the distal surface 243 of the central body 240 with respect to the longitudinal axis $A_L$.

As shown in FIGS. 3 and 4, the implant 200 is movable between a first configuration (FIG. 3) and a second configuration (FIG. 4). When the implant 200 is in the first configuration, the outer surface 221 of the distal retention member 220, the outer surface 261 of the proximal retention member 260 and the outer surface 241 of the central body 240 are substantially aligned. Said another way, the outer surface 221 of the distal retention member 220, the outer surface 261 of the proximal retention member 260 and the outer surface 241 of the central body 240 form a substantially continuous surface. Said yet another way, the outer surface 221 of the distal retention member 220 and the outer surface 261 of the proximal retention member 260 are flush with the outer surface 241 of the central body 240.

To move the implant 200 to the second configuration, the proximal retention member 260 and the distal retention member 220 are moved from their first positions to their second positions by moving them in the direction shown by the arrow CCC in FIG. 4. More particularly, the proximal retention member 260 and the distal retention member 220 translate relative to the central body 240. Said another way, the proximal retention member 260 and the distal retention member 220 move in a direction substantially normal to the longitudinal axis $A_L$. Said yet another way, the proximal retention member 260 and the distal retention member 220 slide along the proximal surface 242 of the central body 240 and the distal surface 243 of the central body 240, respectively. In some embodiments, the proximal retention member 260 and the distal retention member 220 can be moved, for example, by a tool configured to engage the proximal retention member 260 and/or the distal retention member 220. In some embodiments, the implant 200 can include actuators, similar to actuator 111 of the implant 100, to move the proximal retention member 260 and the distal retention member 220 between their respective first positions and their second positions.

When the implant 200 is in the second configuration, the distal retention member 220 and the proximal retention member 260 are offset from the central body 240 in a direction normal to the longitudinal axis $A_L$. Said another way, at least a portion of the outer surface 221 of the distal retention member 220 and at least a portion of the outer surface 261 of the proximal retention member 260 are spaced apart from the outer surface 241 of the central body 240 by a distance D4. In this manner, the distal retention member 220, the proximal retention member 260 and the central member 240 form a saddle, as further described herein.

In use, the implant 200 can be inserted between a first spinous process SP1 and a second spinous process SP2 when the implant 200 is in the first configuration (see e.g., FIG. 3). For example, a medical practitioner can insert the implant 200 percutaneously (e.g., through a cannula, over a guide wire, or the like) into a body of a patient. In some embodiments, a tool, such as those described in U.S. patent application Ser. No. 12/182,425 entitled "Tools and Methods for insertion and Removal of Medical Implants," which is incorporated herein by reference in its entirety, can be used to insert the implant 200 into a body of a patient.

After the implant 200 is between the first spinous process SP1 and the second spinous process SP2, the implant 200 can be moved from the first configuration to the second configuration (see e.g., FIG. 4). In some embodiments, the implant 200 can be actuated using a tool (not shown) configured to move the distal retention member 220 and the proximal retention member 260 relative to the central body 240 when the implant 200 is within the body. Such tools can be configured to maintain the central body 240 in a fixed position while exerting a force on the distal retention member 220 and/or the proximal retention member 260. Such tools can include, for example, those tools described in U.S. patent application Ser. No. 12/182,425 entitled "Tools and Methods for Insertion and Removal of Medical Implants," which is incorporated herein by reference in its entirety. As stated above, when the implant 200 is in the second configuration, the distal retention member 220, the proximal retention member 260 and the central body 240 form a saddle, within which the first spinous process SP1 is disposed. In this manner, when the implant 200 is in the second configuration the distal retention member 220 and the proximal retention member 260 can collectively limit movement of the central body 240 with respect to the first spinous process SP1.

A medical practitioner can remove from and/or reposition the implant 200 within the body multiple times. To remove from and/or reposition the implant 200 within the body, the implant 200 can be moved from the second configuration to the first configuration. This can be done by moving the distal retention member 220 and the proximal retention member 260 to their first positions and thus the implant 200 to its first configuration. After the implant 200 is in the first configuration, the medical practitioner can remove from and/or reposition the implant 200 within the body.

In some embodiments, the distal retention member 220 can include a tapered portion to facilitate insertion of the implant 200 into the body. More particularly, the tapered portion can distract, dilate and/or pierce a bodily tissue. In some embodiments, for example, the tapered portion can pierce a bodily tissue, such as the interspinous ligament, when the implant 200 is inserted into the body. In some embodiments, the tapered portion can dilate a bodily tissue, such as the interspinous ligament, when the implant 200 is inserted into the body. In some embodiments, the tapered portion can distract a space between adjacent spinous processes when the implant 200 is inserted into the body.

Figure 5:
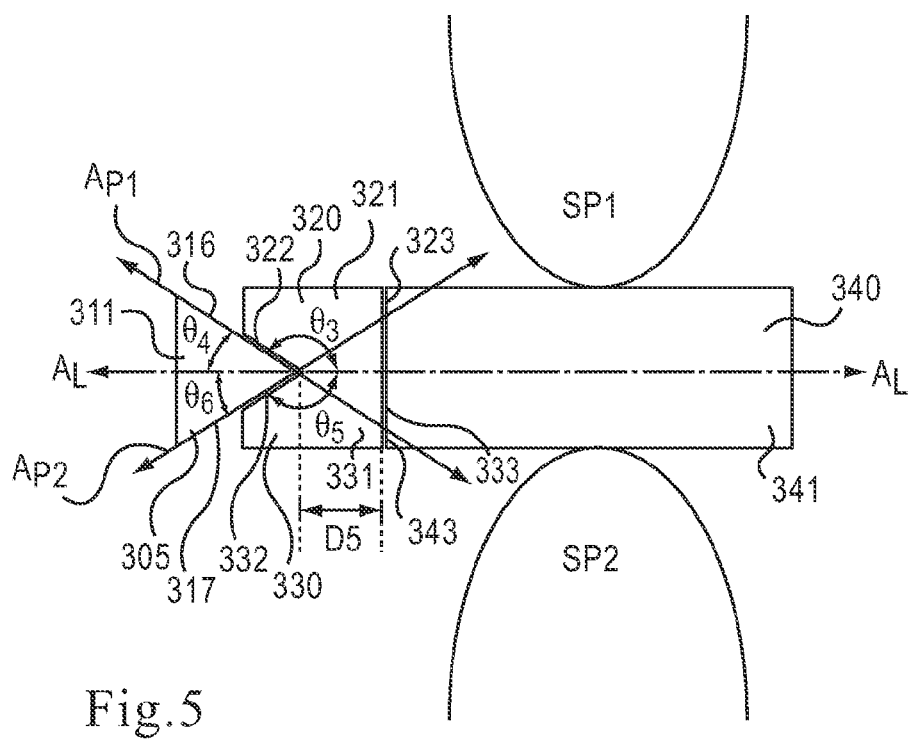
FIGS. 5 and 6 are schematic illustrations of an implant, according to an embodiment in a first configuration and a second configuration, respectively.
Figure 6:
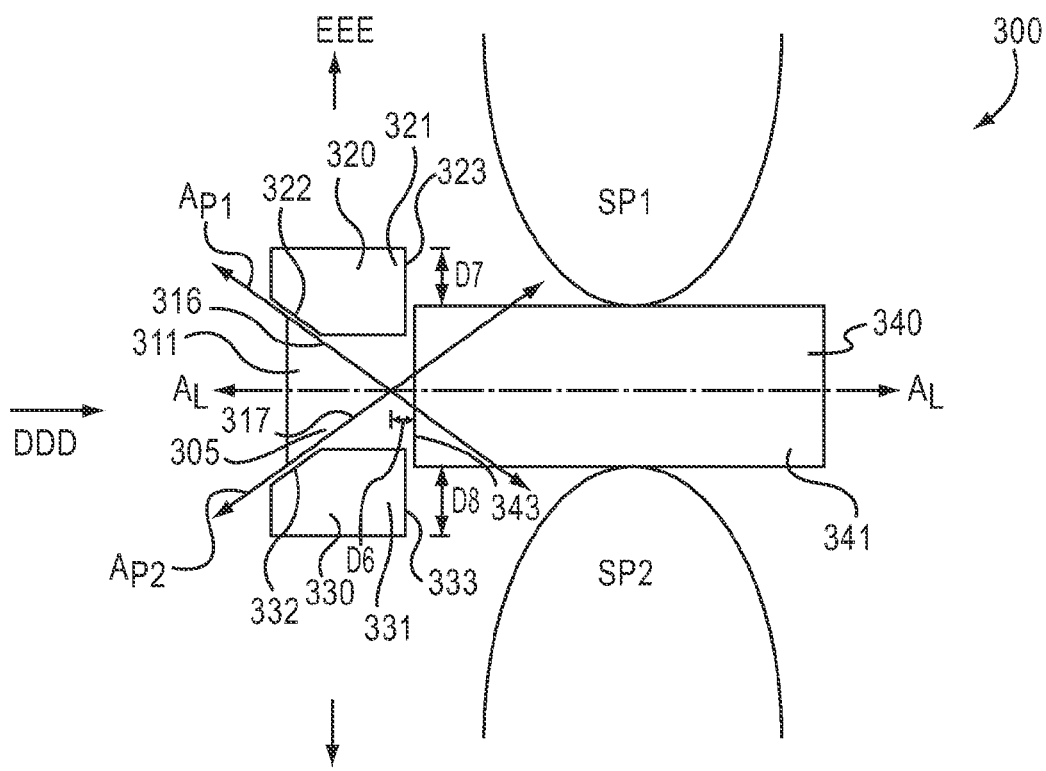

FIGS. 5 and 6 are schematic illustrations of an implant 300, according to an embodiment, in a first configuration and a second configuration, respectively. The implant 300 includes a spacer 340, a first retention member 320, a second retention member 330 and an actuator 311. The spacer 340 includes a side surface 343, an outer surface 341, and defines a longitudinal axis $A_L$. At least a portion of the spacer 340 of implant 300 is configured to be disposed in a space between a first spinous process SP1 and a second spinous process SP2 such that the outer surface 341 of the spacer 340 can engage a first spinous process SP1 and a second spinous process SP2, either directly or through surrounding tissue. Said another way, at least during spinal extension, the outer surface 341 of the spacer 340 is configured to directly engage and/or contact the spinous processes SP1, SP2 and/or the bodily tissue surrounding the spinous processes SP1, SP2 without any intervening structure associated with the implant 300. In some embodiments, for example, a portion of the spacer 340 is disposed within an opening defined in the interspinous ligament (not shown). In this manner, the spacer 340 can contact the spinous processes SP1, SP2 through the interspinous ligament. For purposes of clarity, however, the tissue surrounding the spinous processes SP1, SP2 is not illustrated.

The first retention member 320 of the implant 300 includes a first surface 322, a second surface 323, and an outer surface 321. The second surface 323 of the first retention member 320 is slidably coupled to the side surface 343 of the spacer 340. In this manner, the first retention member 320 can move with respect to the spacer 340. The second surface 323 of the first retention member 320 is substantially normal to the longitudinal axis $A_L$ and is substantially parallel to the side surface 343 of the spacer 340. Said another way, the second surface 323 of the first retention member 320 has an angle with respect to the longitudinal axis $A_L$ that is supplementary to the angle defined by the side surface 343 of the spacer 340 and the longitudinal axis $A_L$.

The first surface 322 of the first retention member 320 is substantially parallel to the first actuation surface 316 of the actuator 311. An axis $A_{P1}$ defined by a plane within the first surface 322 of the first retention member 320 is non-parallel to and non-normal to the longitudinal axis $A_L$. Said another way, the first surface 322 of the first retention member 320 is angularly offset from the longitudinal axis $A_L$ by an angle $\theta_3$. The angle $\theta_3$, which is defined by the first surface 322 of the first retention member 320 and the longitudinal axis $A_L$, is supplementary to the angle $\theta_4$ defined by the first actuation surface 316 of the actuator 311 and the longitudinal axis $A_L$.

The second retention member 330 of the implant 300 includes a first surface 332, a second surface 333, and an outer surface 331. The second surface 333 of the second retention member 330 is slidably coupled to the side surface 343 of the spacer 340. In this manner, the second retention member 330 can move with respect to the spacer 340. The second surface 333 of the second retention member 330 is substantially normal to the longitudinal axis $A_L$ and is substantially parallel to the side surface 343 of the spacer 340. Said another way, the second surface 333 of the second retention member 330 has an angle with respect to the longitudinal axis $A_L$ that is supplementary to the angle defined by the side surface 343 of the spacer 340 and the longitudinal axis $A_L$.

The first surface 332 of the second retention member 330 is substantially parallel to the second actuation surface 317 of the actuator 311. An axis $A_{P2}$ within a plane defined by the first surface 332 of the second retention member 330 is non-parallel to and non-normal to the longitudinal axis $A_L$. Said another way, the first surface 332 of the second retention member 330 is angularly offset from the longitudinal axis $A_L$ by an angle $\theta_5$. The angle $\theta_5$, which is defined by the first surface 332 of the second retention member 330 and the longitudinal axis $A_L$, is supplementary to the angle $\theta_6$ defined by the second actuation surface 317 of the actuator 311 and the longitudinal axis $A_L$.

The actuator 311 of the implant 300 includes a tapered portion 305 having a first actuation surface 316 and a second actuation surface 317. As stated above, the first actuation surface 316 is substantially parallel to the first surface 322 of the first retention member 320. Similarly, the second actuation surface 317 is substantially parallel to the first surface 332 of the second retention member 330. As described above, the angle $\theta_4$, which is defined by the first actuation surface 316 of the actuator 311 and the longitudinal axis $A_L$, is supplementary to the angle $\theta_3$, which is defined by the first surface 322 of the first retention member 320 and the longitudinal axis $A_L$. Similarly, the angle $\theta_6$, which is defined by the second actuation surface 317 of the actuator 311 and the longitudinal axis $A_L$, is supplementary to the angle $\theta_5$, which is defined by the first surface 332 of the second retention member 330 and the longitudinal axis $A_L$.

As shown in FIGS. 5 and 6, the implant 300 is movable between a first configuration (FIG. 5) and a second configuration (FIG. 6). When the implant 300 is in the first configuration, the actuator 311 is spaced apart from the side surface 343 of the spacer 340 along the longitudinal axis $A_L$ by a distance D5. When the implant 300 is in the first configuration, the outer surface 321 of the first retention member 320 and the outer surface 331 of the second retention member 330 are substantially aligned with the outer surface 341 of the spacer 340. Said another way, the outer surface 321 of the first retention member 320 and the outer surface 341 of the spacer 340 form a substantially continuous surface. Similarly, the outer surface 331 of the second retention member 330 and the outer surface 341 of the spacer 340 form a substantially continuous surface. Said yet another way, the outer surface 321 of the first retention member 320 is substantially flush with the outer surface 341 of the spacer 340. Similarly, the outer surface 331 of the second retention member 330 is substantially flush with the outer surface 341 of the spacer 340. Said still another way, the second surface 323 of the first retention member 320 and the second surface 333 of the second retention member 330 are aligned with the side surface 343 of the spacer 340.

To move the implant 300 to the second configuration, the actuator 311 is moved along the longitudinal axis $A_L$ in the direction shown by the arrow DDD in FIG. 6. Movement of the actuator 311 causes the first actuation surface 316 of the actuator 311 to exert an axial force on the first surface 322 of the first retention member 320. As described above, because the first actuation surface 316 of the actuator 311 is at an angle $\theta_4$ with respect to the longitudinal axis $A_L$, a component of the axial force transmitted via the first actuation surface 316 to the first surface 322 of the first retention member 320 has a direction as shown by the arrow EEE in FIG. 6. Accordingly, the force exerted by the actuator 311 on the first retention member 320 causes the first surface 322 of the first retention member 320 to slide on the first actuation surface 316 of the actuator 311, and causes the first retention member 320 to move in the direction shown by the arrow EEE in FIG. 6.

Similarly, movement of the actuator 311 in the direction shown by the arrow DDD in FIG. 6 causes the second actuation surface 317 of the actuator to exert an axial force on the first surface 332 of the second retention member 330. Because the second actuation surface 317 of the actuator 311 is at an acute angle $\theta_6$ with respect to the longitudinal axis $A_L$, a component of the axial force transmitted via the second actuation surface 317 to the first surface 332 of the second retention member 330 has a direction as shown by the arrow FFF in FIG. 6. Accordingly, the force exerted by the actuator 311 on the second retention member 330 causes the first surface 332 of the second retention member 330 to slide on the second actuation surface 317 of the actuator 311, and causes the second retention member 330 to move in the direction shown by the arrow FFF in FIG. 6. Similar to implant 100 described above, the values of the angles $\theta_3$, $\theta_4$, $\theta_5$, $\theta_6$, influence the force to move the implant 300 from the first configuration to the second configuration and the distance the actuator 311 travels to move the implant 300 from the first configuration to the second configuration.

As shown in FIG. 6, when the implant 300 is in the second configuration, the actuator 311 is spaced apart from the side surface 343 of the spacer 340 along the longitudinal axis $A_L$ by a distance D6, which is less than D5. Although shown in FIG. 6 as being spaced apart by the distance D6, in other embodiments, the actuator 311 can be in contact with the side surface 343 of the spacer 340 when the implant 300 is in the second configuration. In such embodiments, after the actuator 311 moves a predetermined distance along the longitudinal axis $A_L$, the actuator 311 can contact the spacer 340, limiting the range of motion of the actuator 311 relative to the spacer 340.

When the implant 300 is in the second configuration, the first retention member 320 is offset from the spacer 340 in a direction substantially normal to the longitudinal axis $A_L$, as shown by arrow EEE in FIG. 6. Said another way, the outer surface 321 of the first retention member 320 is spaced apart from the outer surface 341 of the spacer 340 by a distance D7. Similarly, the second retention member 330 is offset from the spacer 340 in a direction normal to the longitudinal axis $A_L$, as shown by arrow FFF in FIG. 6. Said another way, the outer surface 331 of the second retention member 330 is spaced apart from the outer surface 341 of the spacer 340 by a distance D8. Said yet another way, the outer surface 321 of the first retention member 320 and the outer surface 331 of the second retention member 330 are not aligned with the outer surface 341 of the spacer 340 and are discontinuous with the outer surface 341 of the spacer 340.

In use, the implant 300 can be inserted between a first spinous process SP1 and a second spinous process SP2 when the implant 300 is in the first configuration (see e.g., FIG. 5). For example, a medical practitioner can insert the implant 300 percutaneously (e.g., through a cannula, over a guide wire, or the like) into a body of a patient. In some embodiments, a tool, such as those described in U.S. patent application Ser. No. 12/182,425 entitled "Tools and Methods for insertion and Removal of Medical Implants," which is incorporated herein by reference in its entirety, can be used to insert the implant 300 into a body of a patient.

After the implant 300 is between the first spinous process SP1 and the second spinous process SP2, the implant 300 can be moved from the first configuration to the second configuration (see e.g., FIG. 6). In some embodiments, the implant 300 can be actuated using a tool (not shown) configured to move the actuator 311 relative to the spacer 340 when the implant 300 is within the body. Such tools can be configured to maintain the spacer 340 in a fixed position while exerting a force on the actuator 311. Such tools can include, for example, those tools described in U.S. patent application Ser. No. 12/182,425 entitled "Tools and Methods for Insertion and Removal of Medical Implants," which is incorporated herein by reference in its entirety. When the implant 300 is in the second configuration, the first retention member 320 and the second retention member 330 limit the movement of the implant 300 in the direction shown by arrow DDD in FIG. 6, with respect to the first spinous process SP1 and the second spinous process SP2.

A medical practitioner can remove from and/or reposition the implant 300 within the body multiple times. To remove from and/or reposition the implant 300 within the body, the implant 300 is moved from the second configuration to the first configuration. This can be done by moving the first retention member 320 and the second retention member 360 to their first positions and thus the implant 300 to its first configuration. After the implant 300 is in the first configuration, the medical practitioner can remove from and/or reposition the implant 300 within the body.

In some embodiments, the actuator can have a second tapered portion to facilitate insertion of the implant 300 into the body. More particularly, the second tapered portion can distract, dilate and/or pierce bodily tissue. In some embodiments, for example, the second tapered portion can pierce a bodily tissue, such as an interspinous ligament, when the implant 300 is inserted into the body. In some embodiments, the second tapered portion can dilate a bodily tissue, such as the interspinous ligament, when the implant 300 is inserted into the body. In some embodiments, the second tapered portion can distract a space between adjacent spinous processes when the implant 300 is inserted into the body.

In some embodiments, angle $\theta_3$ does not equal angle $\theta_5$. In such an embodiment, when the implant 300 is in the second configuration, the outer surface 321 of the first retention member 320 and the outer surface 331 of the second retention member 330 are spaced apart from the outer surface 341 by unequal distances. Accordingly, if angle $\theta_3$ is greater than angle $\theta_5$, the outer surface 331 of the second retention member 330 will be spaced further apart from the outer surface 341 of the spacer 340 than the outer surface 321 of the first retention member 320. Said another way, distance D8 is greater than distance D7.

FIGS. 7-13 show an implant 1100, according to an embodiment. Implant 1100 includes a distal end portion 1110, a central portion 1140 and a proximal end portion 1180. At least a portion of the central portion 1140 is disposed between the distal end portion 1110 and the proximal end portion 1180. The implant 1100 defines a lumen 1146 and includes a drive screw 1183 disposed within the lumen 1146. Drive screw 1183 has a tool head 1184 configured to mate with and/or receive an actuator of an insertion tool for rotating the drive screw 1183, as described in U.S. patent application Ser. No. 12/182,425 entitled "Tools and Methods for insertion and Removal of Medical Implants," which is incorporated herein by reference in its entirety.

Distal end portion 1110 of implant 1100 includes an actuator 1111 and a distal retention member 1120. Actuator 1111 includes a tapered surface 1112, a threaded portion 1114 (see FIG. 12), an engagement surface 1116, and a protrusion 1118. The threaded portion 1114 is disposed fixedly within the lumen 1146 and is configured to receive the drive screw 1183. In other embodiments, the actuator 1111 can include a captive nut configured to receive the drive screw 1183.

Figure 7:
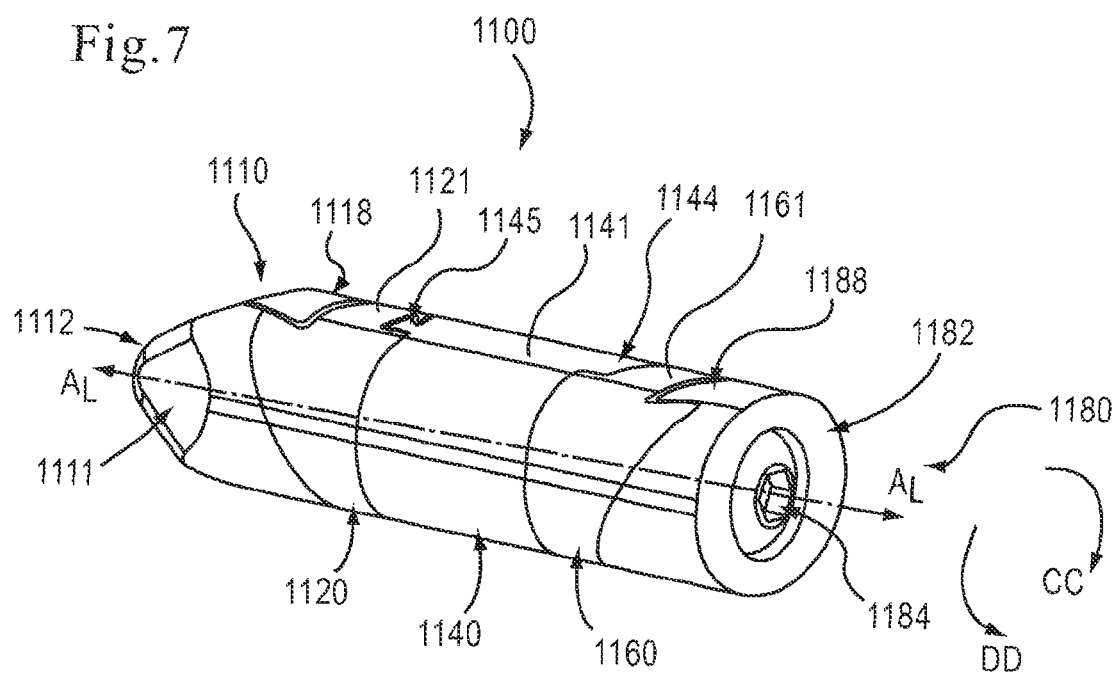
FIGS. 7 and 8 are perspective views of an implant, according to an embodiment in a first configuration and a second configuration, respectively.
Figure 8:
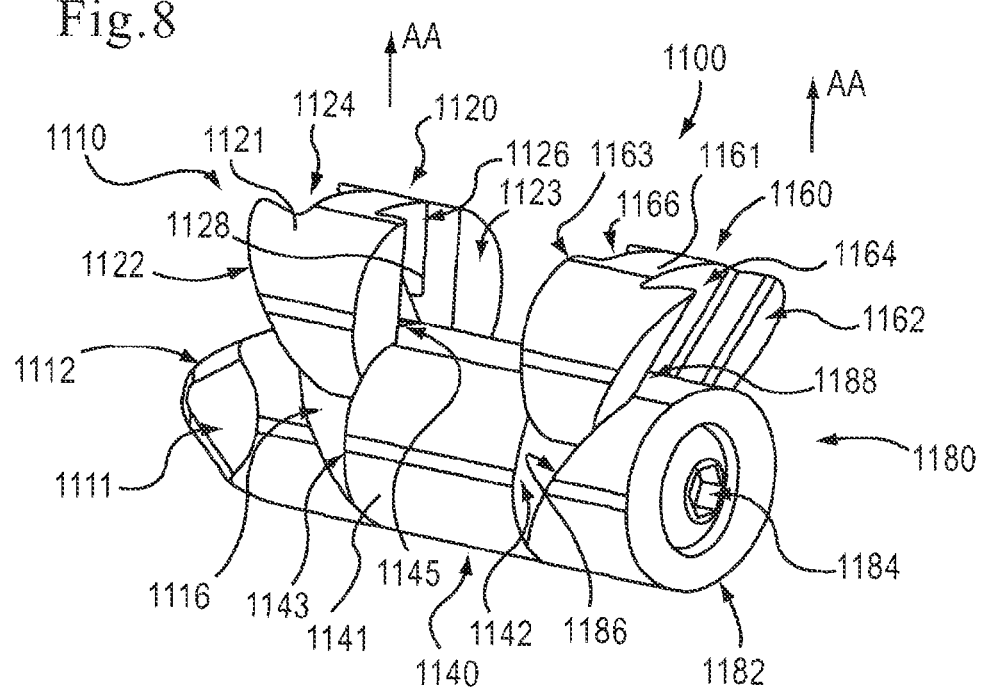
Figure 9:
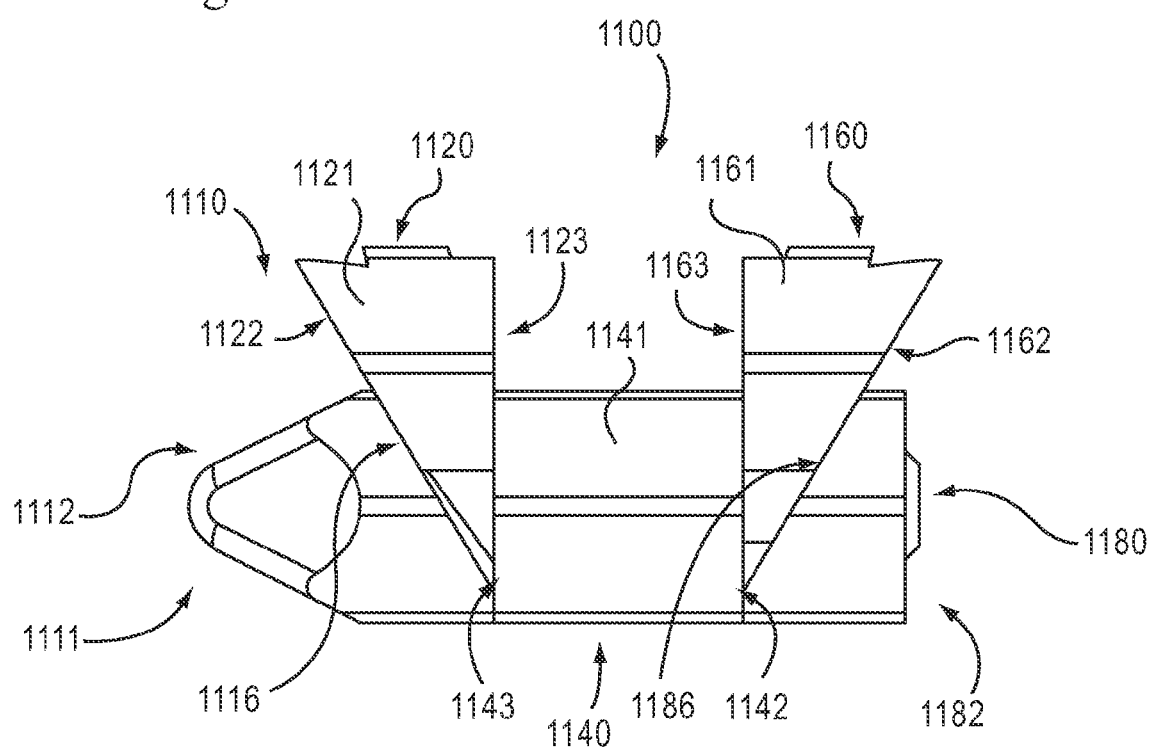
FIG. 9 is a side view of the implant shown in FIG. 8 in the second configuration.
Figure 10:
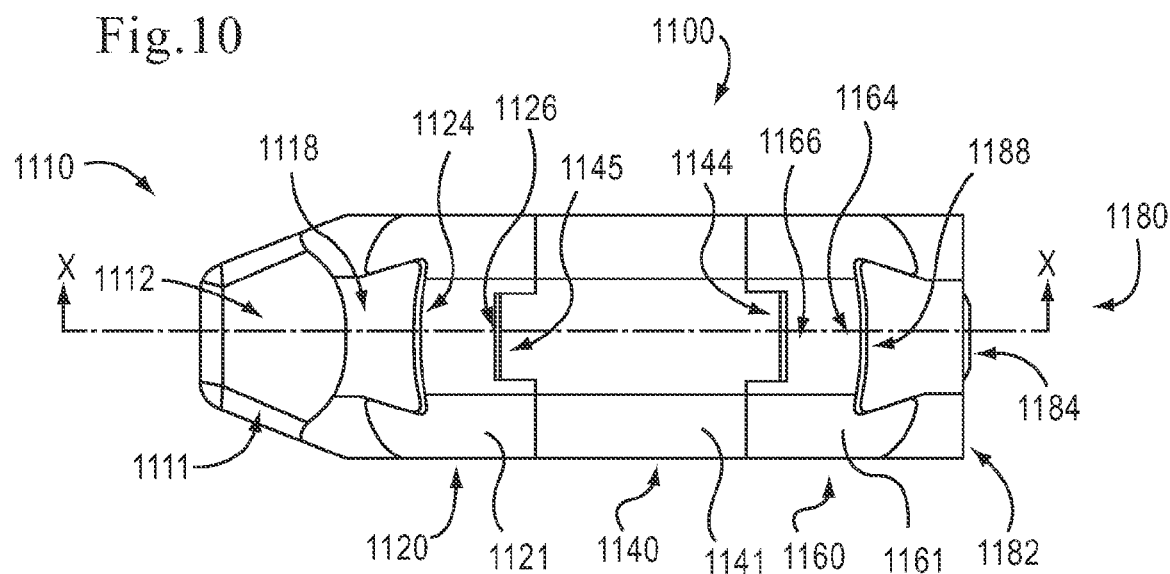
FIG. 10 is a top view of the implant shown in FIG. 7 in the first configuration.
Figure 11:
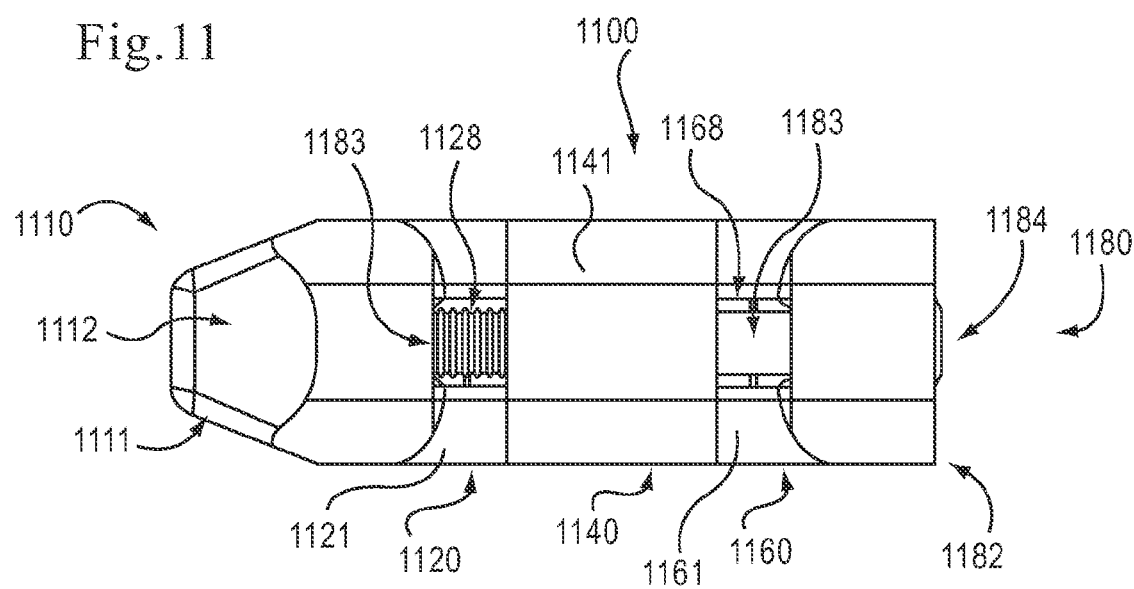
FIG. 11 is a bottom view of the implant shown in FIG. 7 in the first configuration.
Figure 12:
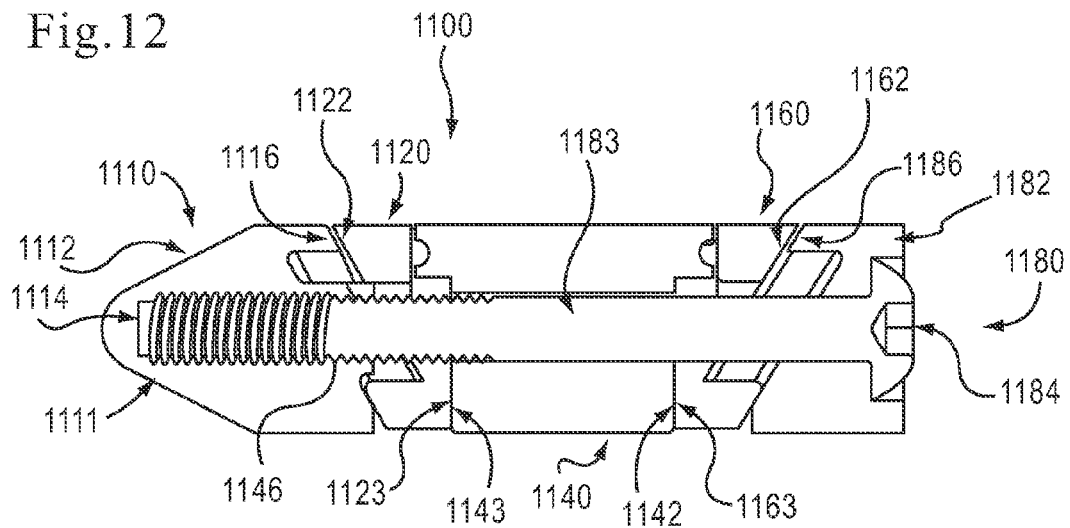
FIG. 12 is a cross-sectional view of the implant shown in FIGS. 7, 10 and 11 in the first configuration, taken along line X-X in FIG. 10.
Figure 13:
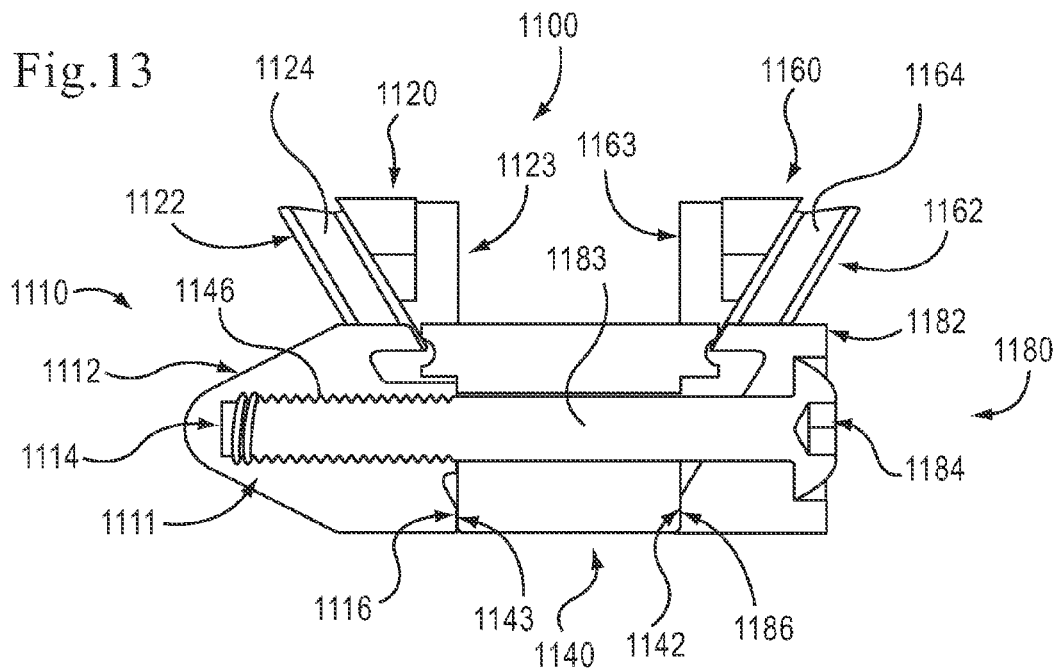
FIG. 13 is a cross-sectional view of the implant shown in FIG. 12 in the second configuration.
Figure 14:
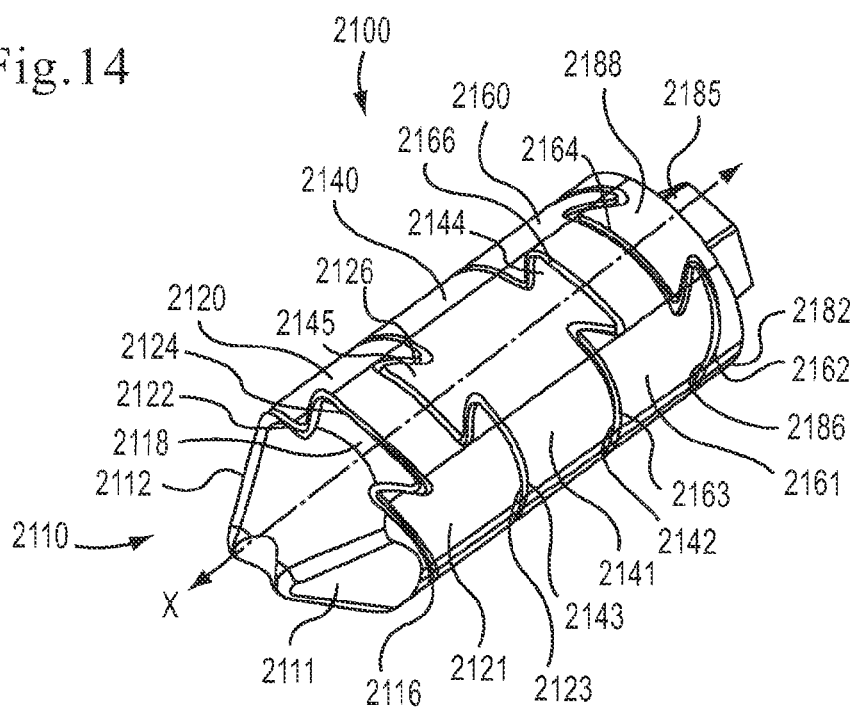
FIG. 14 is a top perspective view of an implant according to an embodiment, in a first configuration.

The engagement surface 1116 of the actuator 1111 is angularly offset from the longitudinal axis $A_L$ of the implant 1100 by an angle between 0 degrees and 90 degrees. Said another way, the engagement surface 1116 of the actuator 1111 is angularly offset from the longitudinal axis $A_L$ of the implant 1100 by an acute angle. As described above, the angular offset of the engagement surface 1116 is associated with moving the implant 1100 between a first configuration (FIG. 7) and a second configuration (FIG. 8).

The protrusion 1118 of the engagement surface 1116 has an undercut such that the distal retention member 1120 is slidably coupled to the actuator 1111. More particularly, the protrusion 1118 has a trapezoidal cross-sectional shape. In this embodiment, the protrusion 1118 is a dovetail protrusion.

Distal retention member 1120 includes an outer surface 1121, a first engagement surface 1122, and a second engagement surface 1123 opposite the first engagement surface 1122. The distal retention member 1120 defines a notch 1128 (see FIG. 11) configured to allow the drive screw 1183 to pass through the distal retention member 1120 when the implant 1100 is in the first configuration. Said another way, when the implant 1100 is in the first configuration, the notch 1128 is aligned with the lumen 1146.

The first engagement surface 1122 of the distal retention member 1120 defines a plane that is angularly offset from the longitudinal axis $A_L$ of the implant 1100 by an angle between 90 degrees and 180 degrees. Said another way, the first engagement surface 1122 of the distal retention member 1120 defines a plane that is angularly offset from the longitudinal axis $A_L$ by an obtuse angle. Moreover, the first engagement surface 1122 of the distal retention member 1120 is substantially parallel to the engagement surface 1116 of the actuator 1111. Said another way, the angular offset of the first engagement surface 1122 of the distal retention member 1120 is supplementary with the angular offset of the engagement surface 1116 of the actuator 1111. Accordingly, the distal retention member 1120 is slidably disposed against actuator 1111.

The first engagement surface 1122 of the distal retention member 1120 defines a first groove 1124 having a trapezoidal cross-sectional shape. In this embodiment, the first groove 1124 has a dovetail shape that corresponds to the shape of the protrusion 1118 of the actuator 1111. The first groove 1124 is configured to slidingly receive the protrusion 1118 of the actuator 1111. The undercut of the protrusion 1118 of the actuator 1111 slidably maintains the protrusion 1118 of the actuator 1111 within the first groove 1124. The first groove 1124 of the first engagement surface 1122 and the protrusion 1118 of the actuator 1111 collectively allow movement of the distal retention member 1120, with respect to the actuator 1111, in a direction substantially parallel to the first engagement surface 1122 of the distal retention member 1120. Moreover, the first groove 1124 of the first engagement surface 1122 and the protrusion 1118 of the actuator 1111 collectively limit movement of the distal retention member 1120, with respect to the actuator 1111, in a direction substantially normal to the first engagement surface 1122 of the distal retention member 1120. The first engagement surface 1122 of the distal retention member 1120 contacts and is configured to slide along the engagement surface 1116 of the actuator 1111 when the first groove 1124 slides about the protrusion 1118 of the actuator 1111. In this manner, the first groove 1124 and the protrusion 1118 collectively maintain the actuator 1111 in sliding contact with the distal retention member 1120.

The second engagement surface 1123 of the distal retention member 1120 is substantially parallel to the distal engagement surface 1143 of the central portion 1140 and defines a plane substantially normal to the longitudinal axis $A_L$ of the implant 1100. The second engagement surface 1123 of the distal retention member 1120 defines a second groove 1126. The second groove 1126 has a shape that corresponds to the shape of the distal protrusion 1145 of the central portion 1140. The second engagement surface 1123 of the distal retention member 1120 is slidably disposed against and/or coupled to the central portion 1140 of the implant 1100, as described in more detail herein.

Proximal end portion 1180 of implant 1100 includes a tool engagement member 1182 and a proximal retention member 1160. Tool engagement member 1182 is configured to mate with and/or receive an insertion tool, as described in more detail below. Tool engagement member 1182 includes an engagement surface 1186 and a protrusion 1188. The engagement surface 1186 of the tool engagement member 1182 is angularly offset from the longitudinal axis $A_L$ of the implant 1100 by an angle between 0 degrees and 90 degrees. Said another way, the engagement surface 1186 of the tool engagement member 1182 is angularly offset from the longitudinal axis $A_L$ of the implant 1100 by an acute angle. As described above, the angular offset of the engagement surface 1186 is associated with moving the implant 1100 between a first configuration (FIG. 7) and a second configuration (FIG. 8).

The protrusion 1188 of the engagement surface 1186 has an undercut such that the proximal retention member 1160 can be slidably coupled to the tool engagement member 1182. More particularly, the protrusion 1188 has a trapezoidal cross-sectional shape. In some embodiments, the protrusion 1188 is a dovetail protrusion.

Proximal retention member 1160 includes an outer surface 1161, a first engagement surface 1162, and a second engagement surface 1163 opposite the first engagement surface 1162. The proximal retention member 1160 defines a notch 1168 (see FIG. 11) configured to allow the drive screw 1183 to pass through the proximal retention member 1160 when the implant 1100 is in the first configuration. Said another way, when the implant 1100 is in the first configuration, the notch 1168 is aligned with the lumen 1146.

The first engagement surface 1162 of the proximal retention member 1160 defines a plane that is angularly offset from the longitudinal axis $A_L$ of the implant 1160 by an angle between 90 degrees and 180 degrees. The first engagement surface 1162 of the proximal retention member 1160 is substantially parallel to the engagement surface 1186 of the tool engagement member 1182. Said another way, the angular offset of the first engagement surface 1162 of the proximal retention member 1160 is supplementary with the angular offset of the engagement surface 1186 of the tool engagement member 1182. Accordingly, the proximal retention member 1160 is slidably disposed against the tool engagement member 1182.

Moreover, the first engagement surface 1162 of the proximal retention member 1160 defines a first groove 1164 having a trapezoidal cross-sectional shape. In this embodiment, the first groove 1164 has a dovetail shape that corresponds to the shape of the protrusion 1188 of the tool engagement member 1182. The first groove 1164 is configured to slidably receive the protrusion 1188 of the tool engagement member 1182. The undercut of the protrusion 1188 of the tool engagement member 1182 maintains the protrusion 1188 of the tool engagement member 1182 within the first groove 1164. The first groove 1164 of the first engagement surface 1162 and the protrusion 1188 of the tool engagement member 1182 collectively allow movement of the proximal retention member 1160, with respect to the tool engagement member 1182, in a direction substantially parallel to the second engagement surface 1163 of the proximal retention member 1160. Moreover, the first groove 1164 of the first engagement surface 1162 and the protrusion 1188 of the tool engagement member 1182 collectively limit movement of the proximal retention member 1160, with respect to the tool engagement member 1182, in a direction substantially normal to the second engagement surface 1163 of the proximal retention member 1160. The first engagement surface 1162 of the proximal retention member 1160 contacts and is configured to slide along the engagement surface 1186 of the tool engagement member 1182 when the first groove 1164 of the proximal retention member 1160 slides along the protrusion 1188 of the tool engagement member 1182. In this manner, the first groove 1164 and the protrusion 1188 collectively maintain the tool engagement member 1182 in sliding contact with the proximal retention member 1160.

The second engagement surface 1163 of the proximal retention member 1160 is substantially parallel to the proximal engagement surface 1142 of the central portion 1140 and defines a plane substantially normal to the longitudinal axis $A_L$ of the implant 1100. In other embodiments, however, the plane defined by the second engagement surface 1163 of the proximal retention member 1160 can be angularly offset from the longitudinal axis $A_L$ of the implant 1100 by an angle other than 90 degrees. Moreover, the second engagement surface 1163 of the proximal retention member 1160 defines a second groove 1166. The second groove 1166 has a shape that corresponds to the shape of the proximal protrusion 1144 of the central portion 1140. The second engagement surface 1163 of the proximal retention member 1160 is slidably disposed against and/or coupled to the central portion 1140 of the implant 1100, as described in more detail herein.

The central portion 1140 of implant 1100 includes a proximal engagement surface 1142, a distal engagement surface 1143, a proximal protrusion 1144, a distal protrusion 1145 and an outer surface 1141. The distal retention member 1120 is slidably coupled to the central portion 1140. More particularly, the second groove 1126 of the distal retention member 1120 is configured to slidingly receive the distal protrusion 1145 of the central portion 1140. The second engagement surface 1123 of the distal retention member 1120 contacts and is configured to slide along the distal engagement surface 1143 of the central portion 1140 when the second groove 1126 of the distal retention member 1120 slides along the distal protrusion 1145 of the central portion 1140.

Similarly, the proximal retention member 1160 is slidably coupled to the central portion 1140. The second groove 1166 of the proximal retention member 1160 is configured to slidingly receive the proximal protrusion 1144 of the central portion 1140. The proximal protrusion 1144 of the central portion 1140 is slidably maintained within the second groove 1166 of the proximal retention member 1160. The second engagement surface 1163 of the proximal retention member 1160 contacts and is configured to slide along the proximal engagement surface 1142 of the central portion 1140 when the second groove 1166 of the proximal retention member 1160 slides along the proximal protrusion 1144 of the central portion 1140.

Implant 1100 has a first configuration (FIG. 7) and a second configuration (FIG. 8). As shown in FIG. 7, when the implant 1100 is in the first configuration, the proximal end portion 1180, the distal end portion 1110 and the central portion 1140 are substantially coaxial (i.e., substantially share a common longitudinal axis). Said another way, when the implant 1100 is in the first configuration, the outer surface 1121 of the distal retention member 1120 and the outer surface 1161 of the proximal retention member 1160 are substantially aligned with the outer surface 1141 of the central portion 1140. Said another way, the outer surface 1121 of the distal retention member 1120, the outer surface 1161 of the proximal retention member 1160, and the outer surface 1141 of the central portion 1140 form a substantially continuous surface. Said yet another way, the outer surface 1121 of the distal retention member 1120 and the outer surface 1161 of the proximal retention member 1160 are flush with the outer surface 1141 of the central portion 1140.

The implant 1100 can be moved between the first configuration and the second configuration as illustrated in FIG. 8. To move the implant 1100 from the first configuration to the second configuration, the drive screw 1183 is rotated as indicated by the arrow CC in FIG. 7. When the drive screw 1183 is rotated, the drive screw 1183 moves the actuator 1111 and the tool engagement member 1182 toward the central portion 1140. More particularly, when the drive screw 1183 is rotated, the engagement surface 1116 of the actuator 1111 exerts an axial force on the first engagement surface 1122 of the distal retention member 1120. Because the engagement surface 1116 of the actuator 1111 is at an acute angle with respect to the longitudinal axis $A_L$, a component of the axial force transmitted via the engagement surface 1116 to the first engagement surface 1122 of the distal retention member 1120 has a direction as shown by the arrow AA in FIG. 8. Said another way, a component of the force exerted by the actuator 1111 on the distal retention member 1120 has a direction that is substantially normal to the longitudinal axis $A_L$. This force causes the distal retention member 1120 to slide on the engagement surface 1116 of the actuator 1111 causing the distal retention member 1120 to move in the direction AA and into the second configuration. Once the distal retention member 1120 slides on the engagement surface 1116 of the actuator 1111 a predetermined distance, a portion of the engagement surface 1116 of the actuator 1111 contacts a portion of the distal engagement surface 1143 of the central portion 1140 (see e.g., FIG. 9) preventing the distal retention member 1120 from sliding further.

Similarly, when the drive screw 1183 is rotated as indicated by the arrow CC in FIG. 7, the engagement surface 1186 of the tool engagement member 1182 exerts an axial force on the first engagement surface 1162 of the proximal retention member 1160. Because the engagement surface 1186 of the tool engagement member 1182 is at an acute angle with respect to the longitudinal axis $A_L$, a component of the axial force transmitted via the engagement surface 1186 to the first engagement surface 1162 of the proximal retention member 1160 has a direction as shown by the arrow AA in FIG. 8. Said another way, a component of the force exerted by the tool engagement member 1182 on the proximal retention member 1160 has a direction that is substantially normal to the longitudinal axis $A_L$. This force causes the proximal retention member 1160 to slide on the engagement surface 1186 of the tool engagement member 1182 causing the proximal retention member 1160 to move in the direction AA and into the second configuration. Once the proximal retention member 1160 slides on the engagement surface 1186 of the tool engagement member 1182 a predetermined distance, a portion of the engagement surface 1186 of the tool engagement member 1182 contacts the proximal engagement surface 1142 of the central portion 1140 preventing the proximal retention member 1160 from sliding further.

When the implant 1100 is in the second configuration the distal retention member 1120 and/or the proximal retention member 1160 are offset from the central portion 1140 in a direction substantially normal to the longitudinal axis $A_L$. Said another way, the outer surface 1121 of the distal retention member 1120 and/or the outer surface 1161 of the proximal retention member 1160 are not aligned with the outer surface 1141 of the central portion 1140 and are discontinuous with the outer surface 1141 of the central portion 1140.

In use, implant 1100 in the first configuration, is inserted percutaneously between a pair of adjacent spinous processes (not shown in FIGS. 7-13). For example, a medical practitioner can insert the implant 1100 percutaneously (e.g., through a cannula, over a guide wire, or the like) into a body of a patient. In some embodiments, an insertion tool such as those described in U.S. patent application Ser. No. 12/182,425 entitled "Tools and Methods for Insertion and Removal of Medical Implants," which is incorporated herein by reference in its entirety, can be used to insert the implant 1100 into a body of a patient. The insertion tool can be configured to be removably coupled to the tool engagement member 1182 such that rotation of the tool engagement member 1182 relative to the insertion tool about the longitudinal axis $A_L$ is limited. In some embodiments, the insertion tool can be configured to be removably coupled to the tool engagement member 1182 such that axial movement of the tool engagement member 1182 relative to the insertion tool is limited. In some embodiments, for example, the insertion tool can be coupled to an outer surface of the tool engagement member 1182. In such embodiments, the outer surface of the tool engagement member 1182 can be configured to facilitate the docking of the insertion tool (not shown) to the implant 1100. For example, in some embodiments, the outer surface of the tool engagement member 1182 can include a lead-in chamfer, a tapered portion and/or a beveled edge to facilitate the docking of the insertion tool onto the tool engagement member 1182 of the implant 1100. In other embodiments, the insertion tool can be matingly coupled to a protrusion and/or a recess of the tool engagement member. The insertion tool can include an actuator configured to be inserted into the tool head 1184 of the drive screw 1183 to rotate the drive screw 1183 about the longitudinal axis $A_L$. This arrangement allows the drive screw 1183 to be rotated without rotating the other portions of the implant 1100.

When inserting the implant 1100 into a body of a patient, the distal end portion 1110 of the implant 1100 is inserted first and is moved past the spinous processes until at least a portion of the central portion 1140 is positioned within a space between the spinous processes. In this manner, the central portion 1140 of the implant 1100 can distract and/or maintain a minimal spacing between the adjacent spinous processes. The distance between the top portion and the bottom portion of the outer surface 1141 of the central portion 1140 can be slightly smaller than the space between the spinous processes to account for surrounding ligaments and tissue. Similar to the central portion 140 of implant 100, in some embodiments, the central portion 1140 in the first configuration directly contacts the spinous processes between which it is positioned. In some embodiments, the central portion 1140 of implant 1100 is a relatively fixed size and is not substantially compressible or expandable.

Once between the spinous processes, the implant 1100 can be moved from the first configuration to the second configuration. As described above, the implant 1100 can be moved between the first configuration and the second configuration in situ using an insertion tool. In the second configuration, the proximal retention member 1160 and the distal retention member 1120 are offset from the central portion 1140 and positioned to limit lateral movement of the implant 1100 with respect to the spinous processes. The proximal retention member 1160 and the distal retention member 1120 are configured to engage the superior spinous process (i.e., either directly or through surrounding tissue) and/or be adjacent to the superior spinous process when in the second configuration. Said another way, the distal retention member 1120, the proximal retention member 1160 and the spacer 1140 form a saddle, within which a spinous process can be disposed. Once the implant 1100 is in the second configuration, the implant 1100 can be released from the insertion tool and the insertion tool can be removed from the patient's body. Although described as engaging the superior spinous process, in other embodiments, the implant 1100 can be oriented within the body such that the proximal retention member 1160 and the distal retention member 1120 engage the inferior spinous process when actuated.

To remove from and/or reposition the implant 1100 within the body, the drive screw 1183 is rotated as indicated by the arrow DD in FIG. 7, by for example, a removal tool (may be similar to an insertion tool). Rotating the drive screw in direction DD causes the dovetail configuration of the protrusion 1118 of the actuator 1111 and/or the dovetail configuration of the protrusion 1188 of the tool engagement member 1182 to pull the distal retention member 1120 and the proximal retention member 1160 back into the first configuration. After the implant 1100 is in the first configuration, a medical practitioner can remove the implant 1100 from and/or reposition the implant 1100 within the body.

FIGS. 14-21 show an implant 2100, according to an embodiment. Implant 2100 includes a distal end portion 2110, a central portion 2140 and a proximal end portion 2180. At least a portion of the central portion 2140 is disposed between the distal end portion 2110 and the proximal end portion 2180. The implant 2100 defines a lumen 2146 (see e.g., FIGS. 20 and 21) and includes a drive screw 2183 disposed within the lumen 2146. Drive screw 2183 has a tool head 2184 configured to mate with and/or receive a tool for rotating the drive screw 2183, as further described herein.

Figure 17:
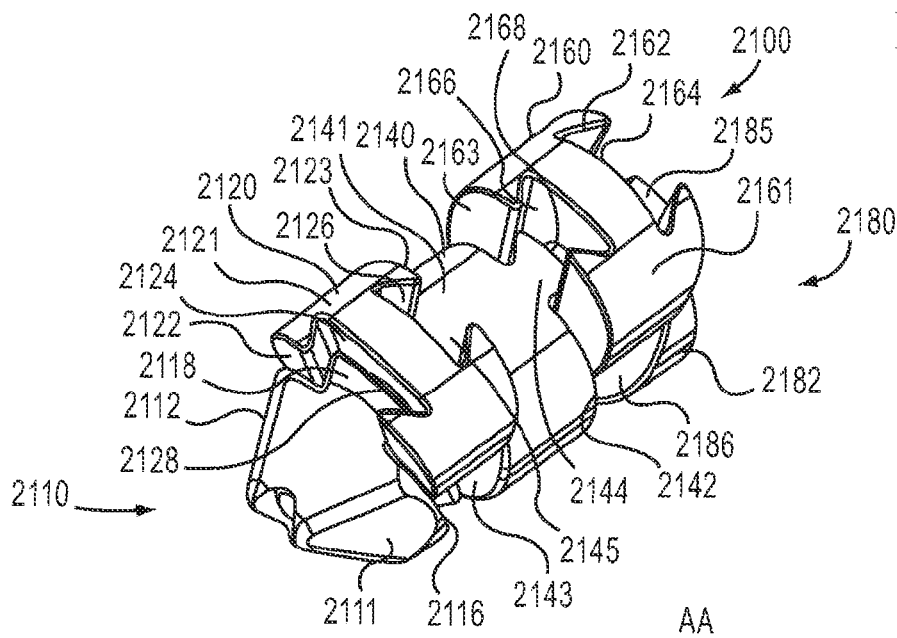
FIG. 17 is a top perspective view of the implant shown in FIG. 14 in a second configuration.

The distal end portion 2110 of implant 2100 includes an actuator 2111 and a distal retention member 2120. Actuator 2111 includes a tapered surface 2112, a threaded portion 2114 (see FIG. 16), and an engagement surface 2116. The threaded portion 2114 is disposed fixedly within the lumen 2146 and is configured to receive the drive screw 2183, as described above. The engagement surface 2116 of the actuator 2111 is angularly offset from the longitudinal axis $A_L$ of the implant 2100 by an angle between 0 degrees and 90 degrees. As described in more detail herein, the angular offset of the engagement surface 2116 is associated with moving the implant 2100 between a first configuration (FIG. 14) and a second configuration (FIG. 17). The engagement surface 2116 includes a protrusion 2118 having an undercut such that the distal retention member 2120 can be coupled to the actuator 2111. More particularly, the protrusion 2118 has a trapezoidal cross-sectional shape. In some embodiments, the protrusion 2118 is a dovetail protrusion.

Distal retention member 2120 includes an outer surface 2121, a first engagement surface 2122, and a second engagement surface 2123 opposite the first engagement surface 2122. The distal retention member 2120 defines a notch 2128 (see FIG. 19) configured to allow the drive screw 2183 to pass through the distal retention member 2120 when the implant 2100 is in the first configuration. The first engagement surface 2122 of the distal retention member 2120 defines a plane that is angularly offset from the longitudinal axis $A_L$ of the implant 2100 by an angle between 90 degrees and 180 degrees. Moreover, the first engagement surface 2122 of the distal retention member 2120 is substantially parallel to the engagement surface 2116 of the actuator 2111. Accordingly, the distal retention member 2120 is slidably disposed against actuator 2111.

The first engagement surface 2122 of the distal retention member 2120 defines a first groove 2124 having a trapezoidal cross-sectional shape. In this embodiment, the first groove 2124 has a dovetail shape that corresponds to the shape of the protrusion 2118 of the actuator 2111. The first groove 2124 of the first engagement surface 2122 and the protrusion 2118 of the actuator 2111 collectively allow movement of the distal retention member 2120, with respect to the actuator 2111, in a direction substantially parallel to the second engagement surface 2123 of the distal retention member 2120. Moreover, the first groove 2124 of the first engagement surface 2122 and the protrusion 2118 of the actuator 2111 collectively limit movement of the distal retention member 2120, with respect to the actuator 2111, in a direction substantially normal to the second engagement surface 2123 of the distal retention member 2120. The first engagement surface 2122 of the distal retention member 2120 contacts and is configured to slide along the engagement surface 2116 of the actuator 2111 when the first groove 2124 slides along the protrusion 2118 of the actuator 2111.

The second engagement surface 2123 of the distal retention member 2120 is substantially parallel to the distal engagement surface 2143 of the central portion 2140 and defines a plane substantially normal to the longitudinal axis $A_L$ of the implant 2100. The second engagement surface 2123 of the distal retention member 2120 defines a second groove 2126 having a trapezoidal cross-sectional shape. In this embodiment, the second groove 2126 has a dovetail shape that corresponds to the shape of the distal protrusion 2145 of the central portion 2140. The second groove 2126 of the second engagement surface 2123 and the distal protrusion 2145 of the central body 2140 collectively limit movement of the distal retention member 2120, with respect to the central portion 2140, in a direction substantially normal to the second engagement surface 2123 of the distal retention member 2120. The second engagement surface 2123 of the distal retention member 2120 is slidably disposed against and/or coupled to the central portion 2140 of the implant 2100, as described in more detail herein.

Figure 18:
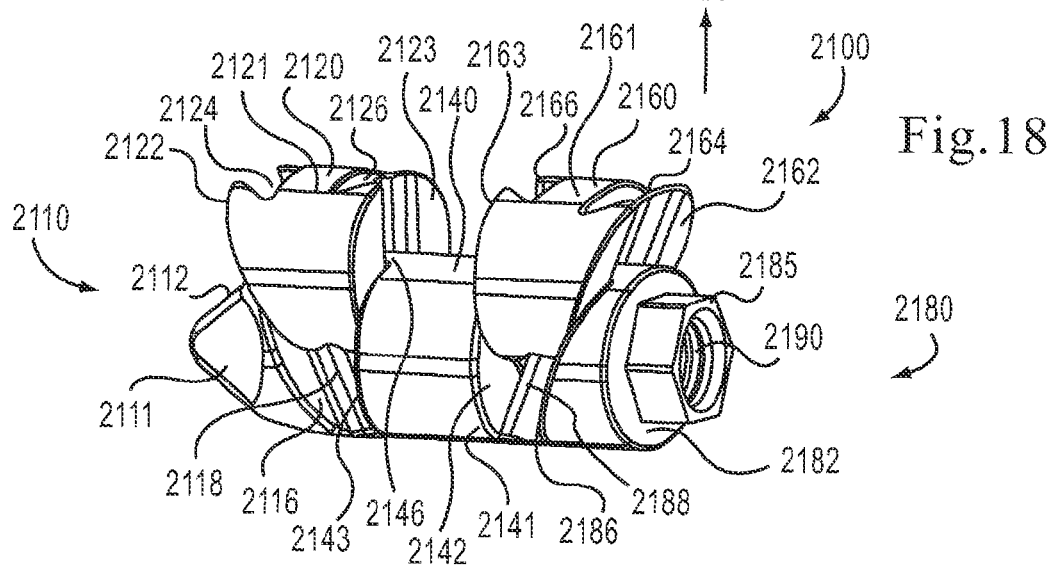
FIG. 18 is a side perspective view of the implant shown in FIG. 14 in the second configuration.
Figure 19:
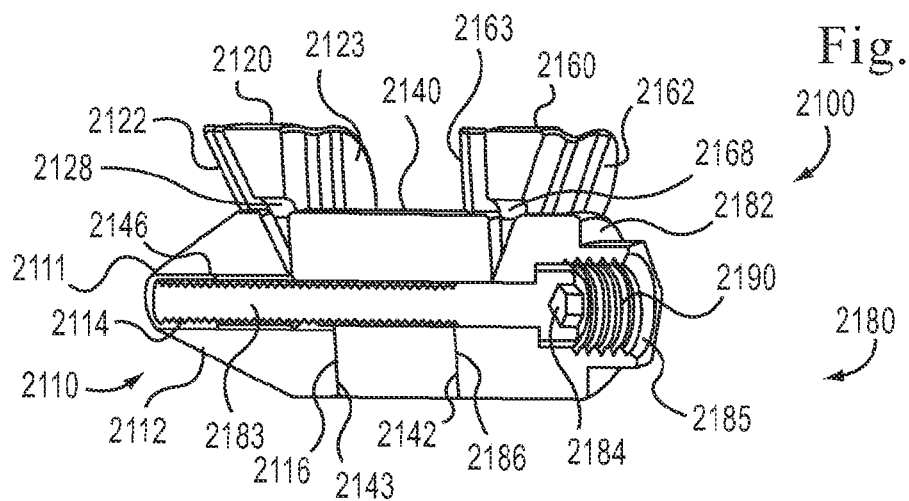
FIG. 19 is a cross-sectional view of the implant shown in FIGS. 17 and 18 in the second configuration.

As shown in FIGS. 18-19, the first engagement surface 2122 of the distal retention member 2120 is non-parallel to the second engagement surface 2123 of the distal retention member 2120. The mating protrusion and grooves, as discussed above, and the non-parallel arrangement of the first engagement surface 2122 and the second engagement surface 2123 collectively lock the distal retention member 2120 between the actuator 2111 and the central body 2140. Said another way, because the first groove 2124 and the protrusion 2118 of the actuator 2111 collectively limit movement of the distal retention member 2120, with respect to the actuator 2111, in a direction substantially normal to the second engagement surface 2123 and the second groove 2126 and the distal protrusion 2145 of the central body 2140 collectively limit movement of the distal retention member 2120, with respect to the central portion 2140, in a direction substantially normal to the second engagement surface 2123, the distal retention member 2120 cannot move unless the actuator 2111 is moved. This arrangement prevents the distal retention member 2120 from becoming inadvertently decoupled from the actuator 2111 and/or the central body 2140.

Proximal end portion 2180 of implant 2100 includes a tool engagement member 2182 and a proximal retention member 2160. Tool engagement member 2182 is configured to mate with and/or receive an insertion tool. Tool engagement member 2182 includes an engagement surface 2186 and a hex portion 2185. The hex portion 2185 includes a hexagonal shaped outer surface configured to be matingly received within a portion of an insertion tool. In this manner, the hex portion 2185 of the tool engagement member 2182 can limit rotational motion of the implant 2100 about the longitudinal axis $A_L$, when the implant 2100 is coupled to an insertion tool. In some embodiments, the hexagonal shaped outer surface of the hex portion 2185 can be configured to facilitate the docking of the insertion tool (not shown) onto the hex portion 2185 of the implant 2100. For example, in some embodiments, the outer surface of the hex portion 2185 can include a lead-in chamfer, a tapered portion and/or a beveled edge to facilitate the docking of the insertion tool onto the hex portion 2185 of the implant 2100.

The hex portion 2185 defines a threaded portion 2190 configured to mate with and/or receive a corresponding threaded portion of an insertion tool (not shown). In some embodiments, for example, the threaded portion 2190 can receive a portion of the threaded intermediate shaft 1430 of the tool shown and described in U.S. patent application Ser. No. 12/182,425 entitled "Tools and Methods for insertion and Removal of Medical Implants," which is incorporated herein by reference in its entirety. In this manner, the threaded portion 2190 can limit axial movement of the implant 2100 with respect to the insertion tool when the implant 2100 is inserted into a body of a patient, as described in further detail below. Moreover, when the shaft of the insertion tool is coupled within the threaded portion 2190, movement of the drive screw 2183 along the longitudinal axis relative to the tool engagement member 2182 is limited. In this manner, the coupling of an insertion tool within the threaded portion 2190 can prevent the drive screw 2183 from moving, thereby maintaining the implant 2100 in the first configuration. In other embodiments, the threaded portion 2190 can include a retainer (e.g., a snap ring, an E-ring or the like) to prevent translation of the drive screw 2183 relative to the tool engagement member 2182.

Similar to the engagement surface 1186 of the tool engagement member 1182, the engagement surface 2186 of the tool engagement member 2182 is angularly offset from the longitudinal axis $A_L$ of the implant 2100 by an angle between 0 degrees and 90 degrees. The engagement surface 2186 includes a protrusion 2188 having an undercut such that the proximal retention member 2160 can be coupled to the tool engagement member 2182. More particularly, the protrusion 2188 has a trapezoidal cross-sectional shape. In this embodiment, the protrusion 2188 is a dovetail protrusion.

Proximal retention member 2160 includes an outer surface 2161, a first engagement surface 2162, and a second engagement surface 2163 opposite the first engagement surface 2162. The proximal retention member 2160 defines a notch 2168 (see FIG. 21) configured to allow the drive screw 2183 to pass through the proximal retention member 2160 when the implant 2100 is in the first configuration. The first engagement surface 2162 of the proximal retention member 2160 defines a plane that is angularly offset from the longitudinal axis $A_L$ of the implant 2160 by an angle between 90 degrees and 180 degrees. Moreover, the first engagement surface 2162 of the proximal retention member 2160 is substantially parallel to the engagement surface 2186 of the tool engagement member 2182. Accordingly, the proximal retention member 2160 is slidably disposed against the tool engagement member 2182.

The first engagement surface 2162 of the proximal retention member 2160 defines a first groove 2164 having a trapezoidal cross-sectional shape. In this embodiment, the first groove 2164 has a dovetail shape that corresponds to the shape of the protrusion 2188 of the tool engagement member 2182. The undercut of the protrusion 2188 of the tool engagement member 2182 slidably maintains the protrusion 2188 of the tool engagement member 2182 within the first groove 2164. More particularly, the first groove 2164 of the first engagement surface 2162 and the protrusion 2188 of the tool engagement member 2182 collectively allow movement of the proximal retention member 2160, with respect to the tool engagement member 2182, in a direction substantially parallel to the second engagement surface 2163 of the proximal retention member 2160. Moreover, the first groove 2164 of the first engagement surface 2162 and the protrusion 2188 of the tool engagement member 2182 collectively limit movement of the proximal retention member 2160, with respect to the tool engagement member 2182, in a direction substantially normal to the second engagement surface 2163 of the proximal retention member 2160. The first engagement surface 2162 of the proximal retention member 2160 contacts and is configured to slide along the engagement surface 2186 of the tool engagement member 2182 when the first groove 2164 of the proximal retention member 2160 slides along the protrusion 2188 of the tool engagement member 2182.

The second engagement surface 2163 of the proximal retention member 2160 is substantially parallel to the proximal engagement surface 2142 of the central portion 2140 and defines a plane substantially normal to the longitudinal axis $A_L$ of the implant 2100. The second engagement surface 2163 of the proximal retention member 2160 defines a second groove 2166 having a trapezoidal cross-sectional shape. In this embodiment, the second groove 2166 has a dovetail shape that corresponds to the shape of the proximal protrusion 2144 of the central portion 2140. The second groove 2166 of the second engagement surface 2163 and the proximal protrusion 2144 of the central portion 2140 collectively limit movement of the proximal retention member 2160, with respect to the central body 2140, in a direction substantially normal to the second engagement surface 2163 of the proximal retention member 2160. The second engagement surface 2163 of the proximal retention member 2160 is slidably disposed against and/or coupled to the central portion 2140 of the implant 2100, as described in more detail herein.

As shown in FIGS. 18-19, the first engagement surface 2162 of the proximal retention member 2160 is non-parallel to the second engagement surface 2163 of the proximal retention member 2160. The mating protrusion and grooves, as discussed above, and the non-parallel arrangement of the first engagement surface 2162 and the second engagement surface 2163 collectively lock the proximal retention member 2160 between the tool engagement member 2182 and the central body 2140. Said another way, because the first groove 2164 and the protrusion 2188 of the tool engagement member 2182 collectively limit movement of the proximal retention member 2160, with respect to the tool engagement member 2182, in a direction substantially normal to the first engagement surface 2162 and the second groove 2166 and the proximal protrusion 2144 of the central body 2140 collectively limit movement of the proximal retention member 2160, with respect to the central portion 2140, in a direction substantially normal to the second engagement surface 2163, the proximal retention member 2160 cannot move unless the tool engagement member 2182 is moved. This arrangement prevents the proximal retention member 2160 from becoming inadvertently decoupled from the tool engagement member 2182 and/or the central body 2140.

The central portion 2140 of implant 2100 includes a proximal engagement surface 2142, a distal engagement surface 2143, a proximal protrusion 2144, a distal protrusion 2145 and an outer surface 2141. The distal retention member 2120 is slidably coupled to the central portion 2140. The second groove 2126 of the distal retention member 2120 is configured to slidingly receive the distal protrusion 2145 of the central portion 2140. The distal protrusion 2145 of the central portion 2140 has a dovetail shape slidably maintaining it within the second groove 2126 of the distal retention member 2120. The second engagement surface 2123 of the distal retention member 2120 contacts and is configured to slide along the distal engagement surface 2143 of the central portion 2140 when the second groove 2126 of the distal retention member 2120 slides along the distal protrusion 2145 of the central portion 2140.

Similarly, the proximal retention member 2160 is slidably coupled to the central portion 2140. The second groove 2166 of the proximal retention member 2160 is configured to slidingly receive the proximal protrusion 2144 of the central portion 2140. The proximal protrusion 2144 of the central portion 2140 has a dovetail shape slidably maintaining it within the second groove 2166 of the proximal retention member 2160. The second engagement surface 2163 of the proximal retention member 2160 contacts and is configured to slide along the proximal engagement surface 2142 of the central portion 2140 when the second groove 2166 of the proximal retention member 2160 slides along the proximal protrusion 2144 of the central portion 2140.

The implant 2100 has a first configuration (FIG. 14) and a second configuration (FIG. 18). When the implant 2100 is in the first configuration, the proximal end portion 2180, the distal end portion 2110 and the central portion 2140 are substantially coaxial (i.e., substantially share a common longitudinal axis). As described above, the implant 2100 can be moved between the first configuration and the second configuration by rotating the drive screw 2183. When the drive screw 2183 is rotated as indicated by the arrow CC in FIG. 15, the drive screw 2183 moves the actuator 2111 and the tool engagement member 2182 toward the central portion 2140.

The engagement surface 2116 of the actuator 2111 exerts an axial force on the first engagement surface 2122 of the distal retention member 2120. Because the engagement surface 2116 of the actuator 2111 is at an acute angle with respect to the longitudinal axis $A_L$, a component of the axial force transmitted via the engagement surface 2116 to the first engagement surface 2122 of the distal retention member 2120 has a direction as shown by the arrow AA in FIG. 18. Said another way, a component of the force exerted by the actuator 2111 on the distal retention member 2120 has a direction that is substantially normal to the longitudinal axis $A_L$. This force causes the distal retention member 2120 to slide on the engagement surface 2116 of the actuator 2111 causing the distal retention member 2120 to move in the direction AA and into the second configuration. Once the distal retention member 2120 slides on the engagement surface 2116 of the actuator 2111 a predetermined distance, a portion of the engagement surface 2116 of the actuator 2111 contacts a portion of the distal engagement surface 2143 of the central portion 2140 preventing the distal retention member 2120 from sliding further.

Figure 15:
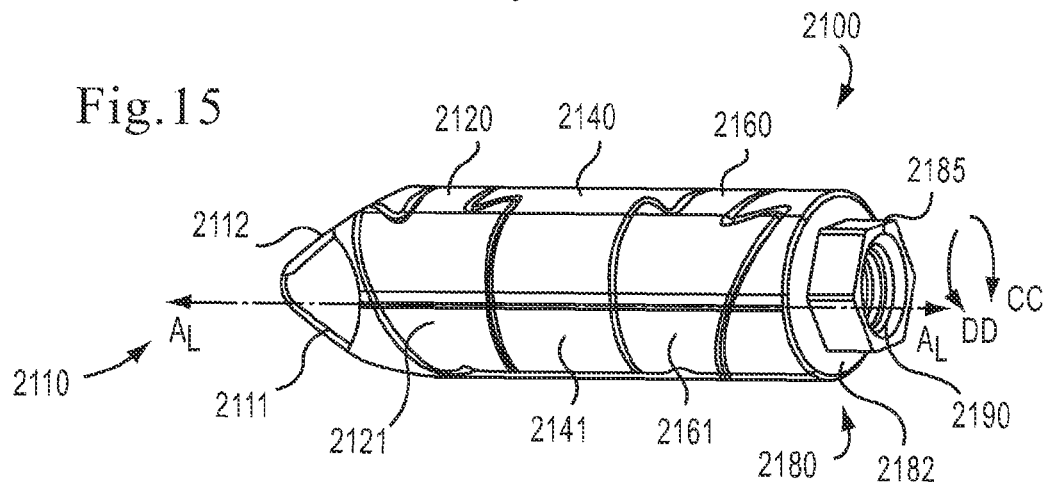
FIG. 15 is a side perspective view of the implant shown in FIG. 14 in the first configuration.
Figure 16:
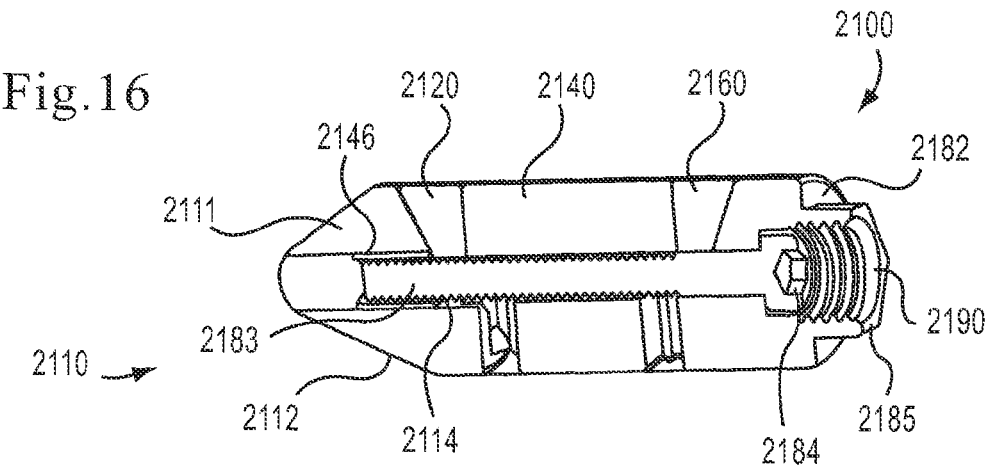
FIG. 16 is a cross-sectional view of the implant shown in FIGS. 14 and 15, taken along line X-X in FIG. 14.

Similarly, when the drive screw 2183 is rotated as indicated by the arrow CC in FIG. 15, the engagement surface 2186 of the tool engagement member 2182 exerts an axial force on the first engagement surface 2162 of the proximal retention member 2160. Because the engagement surface 2186 of the tool engagement member 2182 is at an acute angle with respect to the longitudinal axis $A_L$, a component of the axial force transmitted via the engagement surface 2186 to the first engagement surface 2162 of the proximal retention member 2160 has a direction as shown by the arrow AA in FIG. 18. Said another way, a component of the force exerted by the tool engagement member 2182 on the proximal retention member 2160 has a direction that is substantially normal to the longitudinal axis $A_L$. This force causes the proximal retention member 2160 to slide on the engagement surface 2186 of the tool engagement member 2182 causing the proximal retention member 2160 to move in the direction AA and into the second configuration. Once the proximal retention member 2160 slides on the engagement surface 2186 of the tool engagement member 2180 a predetermined distance, a portion of the engagement surface 2186 of the tool engagement member 2180 contacts the proximal engagement surface 2142 of the central portion 2140 preventing the proximal retention member 2160 from sliding further. Similar to implant 1100, when the implant 2100 is in the second configuration the distal retention member 2120 and/or the proximal retention member 2160 are offset from the central portion 2140 in a direction substantially normal to the longitudinal axis $A_L$.

In use, implant 2100 in the first configuration, is inserted percutaneously between a pair of adjacent spinous processes (not shown in FIGS. 14-21). For example, a medical practitioner can insert the implant 2100 percutaneously (e.g., through a cannula, over a guide wire, or the like) into a body of a patient. In some embodiments, an insertion tool such as those described in U.S. patent application Ser. No. 12/182,425 entitled "Tools and Methods for insertion and Removal of Medical Implants," which is incorporated herein by reference in its entirety, can be used to insert the implant 2100 into a body of a patient. The insertion tool can be configured to be removably coupled to the tool engagement member 2182 such that rotation of the tool engagement member 2182 relative to the insertion tool about the longitudinal axis $A_L$ is limited. More particularly, a portion of the insertion tool can be disposed about the hex portion 2185 of the tool engagement member 2182 such that rotational motion about the longitudinal axis $A_L$ is limited. Additionally, the insertion tool can include a threaded portion configured to be threadedly coupled within the threaded portion 2190 of the hex portion 2185. In this manner, the insertion tool can be removably coupled to the tool engagement member 2182 such that axial movement of the tool engagement member 2182 relative to the insertion tool is limited.

The insertion tool can include actuator configured to be inserted into the tool head 2184 of the drive screw 2183 to rotate the drive screw 2183 about the longitudinal axis $A_L$. This arrangement allows the drive screw 2183 to be rotated without rotating the other portions of the implant 2100. Accordingly, the implant 2100 can be inserted into, repositioned within and/or removed from a body, as described above.

Once between the spinous processes, the implant 2100 can be moved from the first configuration to the second configuration. In the second configuration, the proximal retention member 2160 and the distal retention member 2120 are offset from the central portion 2140 and positioned to limit lateral movement of the implant 2100 with respect to the spinous processes. The proximal retention member 2160 and the distal retention member 2120 are configured to engage a spinous process (i.e., either directly or through surrounding tissue) and/or be adjacent to a spinous process when in the second configuration. Said another way, the distal retention member 2120, the proximal retention member 2160 and the central portion 2140 form a saddle, within which a spinous process can be disposed.

Figure 22:
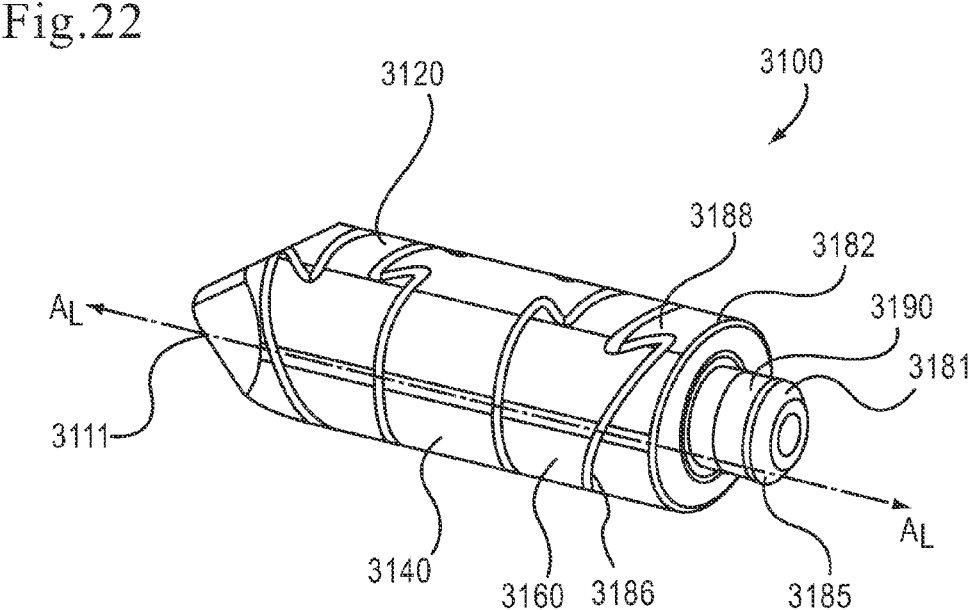
FIG. 22 is a perspective view of an implant according to an embodiment, in a first configuration.
Figure 23:
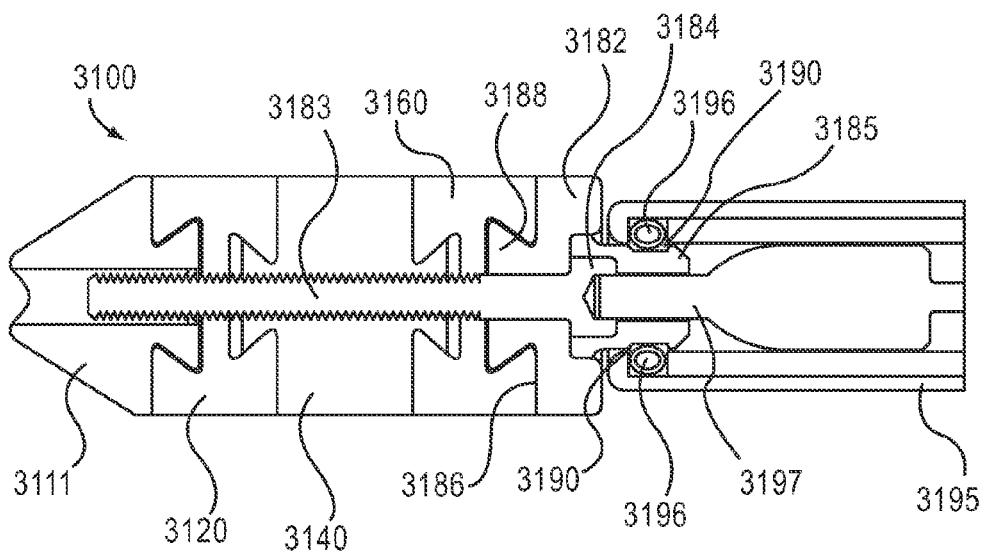
FIG. 23 is a cross-sectional view of the implant shown in FIG. 22 coupled to an insertion tool.

FIGS. 22-23 show an implant 3100, according to an embodiment. As shown in FIG. 22, the implant 3100 includes an actuator 3111, a distal retention member 3120, a central portion 3140, a proximal retention member 3160, and a tool engagement member 3182. The structure and operation of the actuator 3111, distal retention member 3120, central portion 3140, and proximal retention member 3160 are similar to the structure and operation of the actuator 2111, distal retention member 2120, central portion 2140, and proximal retention member 2160, respectively. Accordingly, only the tool engagement member 3182 is described in detail below.

Tool engagement member 3182 includes an engagement surface 3186 and a coupling protrusion 3185. The engagement surface 3186 includes a dovetail protrusion 3188, which is similar to the structure and operation of the engagement surface 2186 and the protrusion 2188 of implant 2100, respectively. As such, the engagement surface 3186 and the dovetail protrusion 3188 are not described in detail.

The tool coupling protrusion 3185 is configured to be removably coupled to an insertion tool 3195. Details of the insertion tool 3195 are described in more detail in copending U.S. patent application Ser. No. 12/182,425 entitled "Tools and Methods for insertion and Removal of Medical Implants," which is incorporated herein by reference in its entirety. Specifically, the tool coupling protrusion 3185 is configured receive a shaft 3197 of the insertion tool 3195. The end of the shaft 3197 is configured to engage a tool head 3184 of a drive screw 3183. In use, the shaft 3197 can rotate the drive screw 3183 to move the implant 3100 between a first configuration and a second configuration, as described above.

Moreover, the tool coupling protrusion 3185 includes a groove 3190 configured to receive a snap-ring 3196 of the insertion tool 3195. The snap-ring 3196 can be, for example, spring coil. In this manner, the insertion tool 3195 can retain the implant 3100, when the implant 3100 is inserted into a body of a patient. More particularly, the snap-ring 3196 and the groove 3190 can collectively form an interference fit such both axial and rotation movement of the implant 3100 relative to the insertion tool 3195 is limited.

The tool coupling protrusion 3185 includes a lead-in chamfer 3181 to facilitate the docking of the insertion tool 3195 to the implant 3100. Although not shown in FIG. 23, in some embodiments, the lumen defined by the coupling protrusion 3185 can also include a lead-in chamfer, a tapered portion and/or a beveled edge to facilitate the insertion of the shaft 3197 the insertion tool 3195 into the coupling protrusion 3185. Said another way, in some embodiments, the coupling protrusion 3185 can include an inner-diameter chamfer.

FIGS. 24-30 show an implant 4100, according to an embodiment. Implant 4100 includes a distal end portion 4110, a central portion 4140 and a proximal end portion 4180. At least a portion of the central portion 4140 is between the distal end portion 4110 and the proximal end portion 4180. The implant 4100 defines a lumen 4146 and includes a drive screw 4183 disposed within the lumen 4146. The drive screw 4183 has a tool head 4184 configured to mate with and/or receive a tool for rotating the drive screw 4183, as further described herein.

Distal end portion 4110 of implant 4100 includes an actuator 4111, a first distal retention member 4120 and a second distal retention member 4130. Actuator 4111 includes a tapered surface 4112, a threaded portion 4114 (see FIG. 28), a first engagement surface 4116, a second engagement surface 4117, a first protrusion 4118, a second protrusion 4119, a first stabilizing pin 4113 and a second stabilizing pin 4115 (see FIG. 28). The threaded portion 4114 is disposed fixedly within the lumen 4146 and is configured to receive the drive screw 4183. In other embodiments, the insertion member can include a captive nut configured to receive the drive screw. The first stabilizing pin 4113 and the second stabilizing pin 4115 of the actuator 4111 are elongated members configured to slidably couple the actuator 4111 to the central portion 4140 to prevent independent rotational movement of the actuator 4111 with respect to the central portion 4140.

The first engagement surface 4116 of the actuator 4111 is angularly offset from the longitudinal axis $A_L$ of the implant 4100 by an angle between 0 degrees and 90 degrees. As described in more detail herein, the angular offset of the first engagement surface 4116 is associated with moving the implant 4100 between a first configuration (FIG. 24) and a second configuration (FIG. 25).

The first engagement surface 4116 includes a first protrusion 4118 having an undercut. More particularly, the first protrusion 4118 has a trapezoidal cross-sectional shape. In this embodiment, the first protrusion 4118 is a dovetail protrusion. The first protrusion 4118 is configured to engage a groove 4124 of the first distal retention member 4120. Similarly, the second engagement surface 4117 includes a second protrusion 4119 having an undercut. More particularly, the second protrusion 4119 has a trapezoidal cross-sectional shape. In this embodiment, the second protrusion 4119 is a dovetail protrusion. The second protrusion 4119 is configured to engage a groove 4134 of the second distal retention member 4130.

The first distal retention member 4120 includes an outer surface 4121, a first engagement surface 4122, and a second engagement surface 4123, opposite the first engagement surface 4122. The first distal retention member 4120 defines a notch 4128 configured to allow the drive screw 4183 to pass therethrough when the implant 4100 is in the first configuration. Said another way, when the implant 4100 is in the first configuration, the notch 4128 is aligned with the lumen 4146.

The first engagement surface 4122 of the first distal retention member 4120 defines a plane that is angularly offset from the longitudinal axis $A_L$ of the implant 4100 by an angle between 90 degrees and 180 degrees. Said another way, the first engagement surface 4122 of the first distal retention member 4120 defines a plane that is angularly offset from the longitudinal axis $A_L$ by an obtuse angle. Moreover, the first engagement surface 4122 of the first distal retention member 4120 is substantially parallel to the first engagement surface 4116 of the actuator 4111. Said another way, the angular offset of the first engagement surface 4122 of the distal retention member 4120 is supplementary to the angular offset of the first engagement surface 4116 of the actuator 4111. Accordingly, the first distal retention member 4120 is slidably disposed against actuator 4111.

Moreover, the first engagement surface 4122 of the first distal retention member 4120 defines a groove 4124. The groove 4124 has a trapezoidal cross-sectional shape. In this embodiment, the groove 4124 has a dovetail shape that corresponds to the shape of the first protrusion 4118 of the actuator 4111. The groove 4124 is configured to slidingly receive the first protrusion 4118 of the actuator 4111. The undercut of the first protrusion 4118 of the actuator 4111 slidably maintains the first protrusion 4118 of the actuator 4111 within the groove 4124. The groove 4124 of the first engagement surface 4122 and the protrusion 4118 of the actuator 4111 collectively allow movement of the first distal retention member 4120, with respect to the actuator 4111, in a direction substantially parallel to the first engagement surface 4122 of the first distal retention member 4120. Moreover, the groove 4124 of the first engagement surface 4122 and the protrusion 4118 of the actuator 4111 collectively limit movement of the first distal retention member 4120, with respect to the actuator 4111, in a direction substantially normal to the first engagement surface 4122 of the distal retention member 4120. The first engagement surface 4122 of the first distal retention member 4120 contacts and is configured to slide along the first engagement surface 4116 of the actuator 4111 when the groove 4124 slides along the first protrusion 4118 of the actuator 4111.

The second engagement surface 4123 of the first distal retention member 4120 is substantially parallel to the distal engagement surface 4143 of the central portion 4140 and defines a plane substantially normal to the longitudinal axis $A_L$ of the implant 4100. The second engagement surface 4123 of the first distal retention member 4120 can be slidably disposed against and/or coupled to the central portion 4140 of the implant 4100.

The second distal retention member 4130 includes an outer surface 4131, a first engagement surface 4132, and a second engagement surface 4133, opposite the first engagement surface 4132. The second distal retention member 4130 defines a notch 4138 configured to allow the drive screw 4183 to pass therethrough when the implant 4100 is in the first configuration. Moreover, the first engagement surface 4132 of the second distal retention member 4130 defines a groove 4134. The structure and function of second distal retention member 4130 is similar to that of the first distal retention member 4120, and is therefore not described in detail.

Proximal end portion 4180 of implant 4100 includes a tool engagement member 4182, a first proximal retention member 4160 and a second proximal retention member 4170. Tool engagement member 4182 is configured to mate with and/or receive an insertion tool, such as those described in copending U.S. patent application Ser. No. 12/182,425 entitled "Tools and Methods for Insertion and Removal of Medical Implants," which is incorporated herein by reference in its entirety. In some embodiments, for example, an insertion tool (not shown) can be coupled to an outer surface of the tool engagement member 4182. In such embodiments, the outer surface of the tool engagement member 4182 can be configured to facilitate the docking of the insertion tool (not shown) to the implant 4100. For example, in some embodiments, the outer surface of the tool engagement member 4182 can include a lead-in chamfer, a tapered portion and/or a beveled edge to facilitate the docking of the insertion tool onto the tool engagement member 4182 of the implant 4100.

Tool engagement member 4182 includes a first engagement surface 4186, a second engagement surface 4187, a first stabilizing pin 4181 and a second stabilizing pin 4185 (see FIG. 28). The first stabilizing pin 4181 and the second stabilizing pin 4185 of the tool engagement member 4182 are elongated members configured to slidably couple the tool engagement member 4182 to the central portion 4140 to prevent independent rotational movement of the tool engagement member 4182 with respect to the central portion 4140.

The first engagement surface 4186 of the tool engagement member 4182 is angularly offset from the longitudinal axis $A_L$ of the implant 4100 by an angle between 0 degrees and 90 degrees. As described in more detail herein, the angular offset of the first engagement surface 4186 is associated with moving the implant 4100 between a first configuration (FIG. 24) and a second configuration (FIG. 25).

The first engagement surface 4186 includes a first protrusion 4188 having an undercut. More particularly, the first protrusion 4188 has a trapezoidal cross-sectional shape. In this embodiment, the first protrusion 4188 is a dovetail protrusion. The first protrusion 4188 is configured to engage a groove 4164 of the first proximal retention member 4160. Similarly, the second engagement surface 4187 of the tool engagement member 4182 includes a second protrusion 4189 having an undercut. More particularly, the second protrusion 4189 has a trapezoidal cross-sectional shape. In this embodiment, the second protrusion 4189 is a dovetail protrusion. The second protrusion 4189 is configured to engage a groove 4174 of the second proximal retention member 4170.

The first proximal retention member 4160 includes an outer surface 4161, a first engagement surface 4162, and a second engagement surface 4163, opposite the first engagement surface 4162. The first proximal retention member 4160 defines a notch 4168 configured to allow the drive screw 4183 to pass therethrough when the implant 4100 is in the first configuration. Said another way, when the implant 4100 is in the first configuration, the notch 4168 is aligned with the lumen 4146.

The first engagement surface 4162 of the first proximal retention member 4160 defines a plane that is angularly offset from the longitudinal axis $A_L$ of the implant 4100 by an angle between 90 degrees and 180 degrees. Moreover, the first engagement surface 4162 of the first proximal retention member 4120 is substantially parallel to the first engagement surface 4186 of the tool engagement member 4182. Said another way, the angular offset of the first engagement surface 4162 of the first proximal retention member 4160 is supplementary with the angular offset of the first engagement surface 4186 of the tool engagement member 4182. Accordingly, the first proximal retention member 4160 is slidably disposed against the tool engagement member 4182.

The first engagement surface 4162 of the first proximal retention member 4160 defines a groove 4164. The groove 4164 has a trapezoidal cross-sectional shape. In this embodiment, the groove 4164 has a dovetail shape that corresponds to the shape of the first protrusion 4188 of the tool engagement member 4182. The groove 4164 is configured to slidingly receive the first protrusion 4188 of the tool engagement member 4182. The undercut of the first protrusion 4188 of the tool engagement member 4182 slidably maintains the first protrusion 4188 of the tool engagement member 4182 within the first groove 1124. The groove 4164 of the first engagement surface 4162 and the first protrusion 4188 of the tool engagement member 4182 collectively allow movement of the first proximal retention member 4160, with respect to the tool engagement member 4182, in a direction substantially parallel to the second engagement surface 4163 of first the proximal retention member 4160. Moreover, the groove 4164 of the first engagement surface 4162 and the first protrusion 4188 of the tool engagement member 4182 collectively limit movement of the first proximal retention member 4160, with respect to the tool engagement member 4182, in a direction substantially normal to the first engagement surface 4162 of the first proximal retention member 4160. The first engagement surface 4162 of the first proximal retention member 4160 contacts and is configured to slide along the first engagement surface 4186 of the tool engagement member 4182 when the groove 4164 slides along the first protrusion 4188 of the tool engagement member 4182.

The second engagement surface 4163 of the first proximal retention member 4160 is substantially parallel to the proximal engagement surface 4142 of the central portion 4140 and defines a plane substantially normal to the longitudinal axis $A_L$ of the implant 4100. In other embodiments, the plane defined by the second engagement surface 4163 of the first proximal retention member 4160 can be angularly offset from the longitudinal axis $A_L$ of the implant 4100 by an angle other than 90 degrees. The second engagement surface 4163 of the first proximal retention member 4160 can be slidably disposed against and/or coupled to the central portion 4140 of the implant 4100.

The second proximal retention member 4170 includes an outer surface 4171, a first engagement surface 4172, and a second engagement surface 4173, opposite the first engagement surface 4172. The second proximal retention member 4170 defines a notch 4178 configured to allow the drive screw 4183 to pass through the second proximal retention member 4170 when the implant 4100 is in the first configuration. Moreover, the first engagement surface 4172 of the second proximal retention member 4170 defines a groove 4174. The second proximal retention member 4170 is configured similar to the first proximal retention member 4160, and is therefore not discussed in detail below.

The central portion 4140 of implant 4100 includes an outer surface 4141, a proximal engagement surface 4142 and a distal engagement surface 4143. The central portion 4140 also defines a first proximal stabilizing groove 4144, a second proximal stabilizing groove (not shown in FIG. 28), a first distal stabilizing groove (not shown in FIG. 28) and a second distal stabilizing groove 1149 (see FIG. 28).

The second engagement surface 4163 of the first proximal retention member 4160 and the second engagement surface 4173 of the second proximal retention member 4170 are both configured to slide along the proximal engagement surface 4142 of the central portion 4140. Likewise, the second engagement surface 4123 of the first distal retention member 4120 and the second engagement surface 4133 of the second distal retention member 4130 are both configured to slide along the distal engagement surface 4143 of the central portion 4140.

Figure 24:
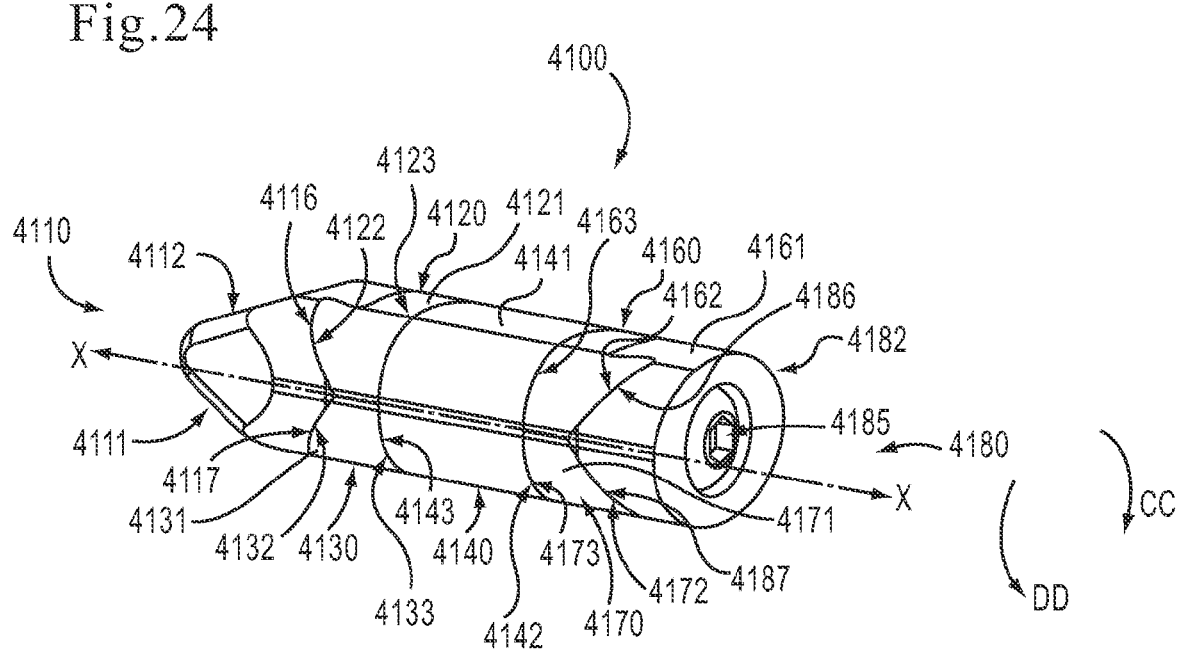
Figure 29:
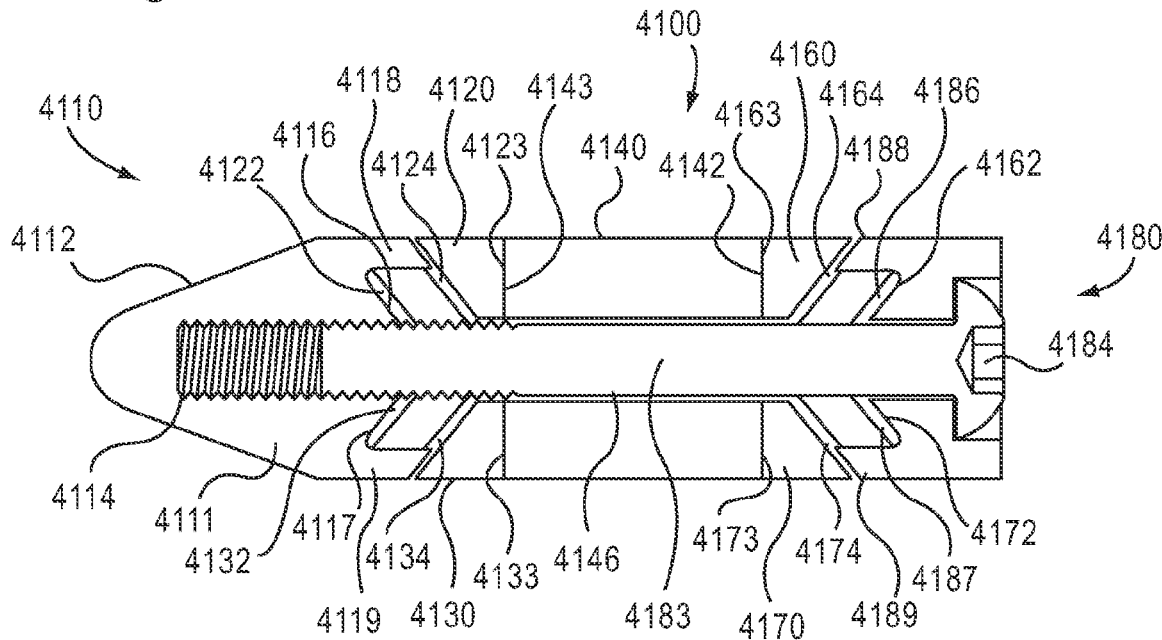
FIG. 29 is a cross-sectional view of the implant shown in FIG. 27, taken along line X-X in FIG. 27.
Figure 30:
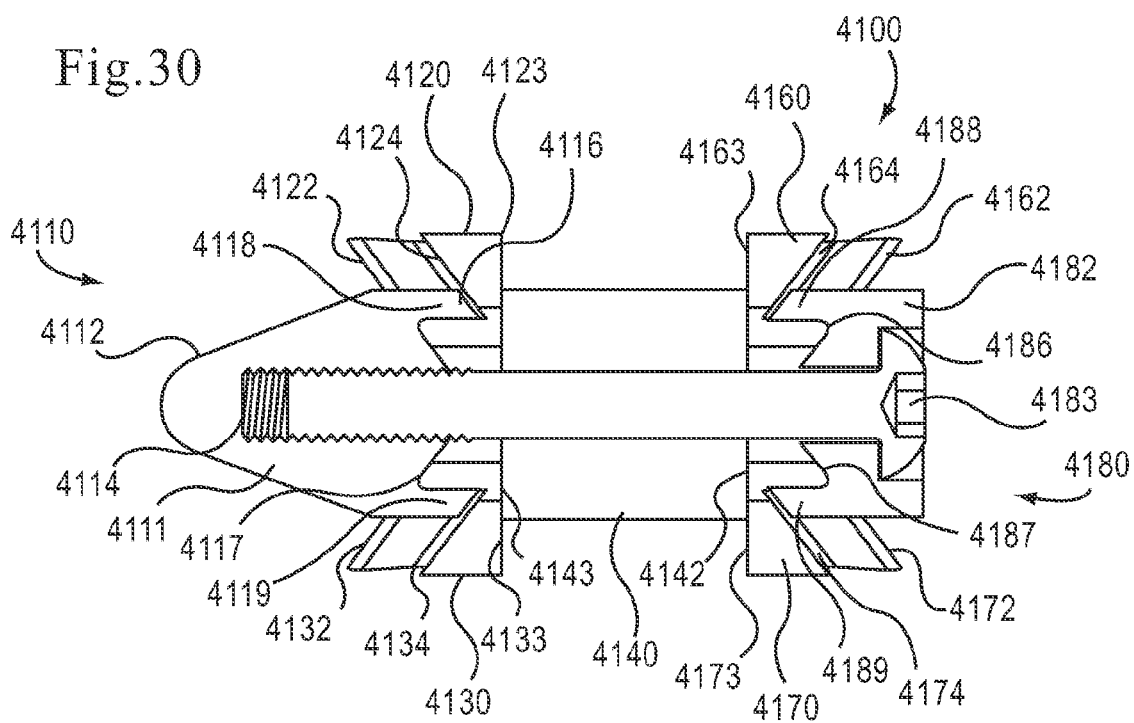
FIG. 30 is a cross-sectional view of the implant shown in FIG. 29 in the second configuration.
Figure 34:
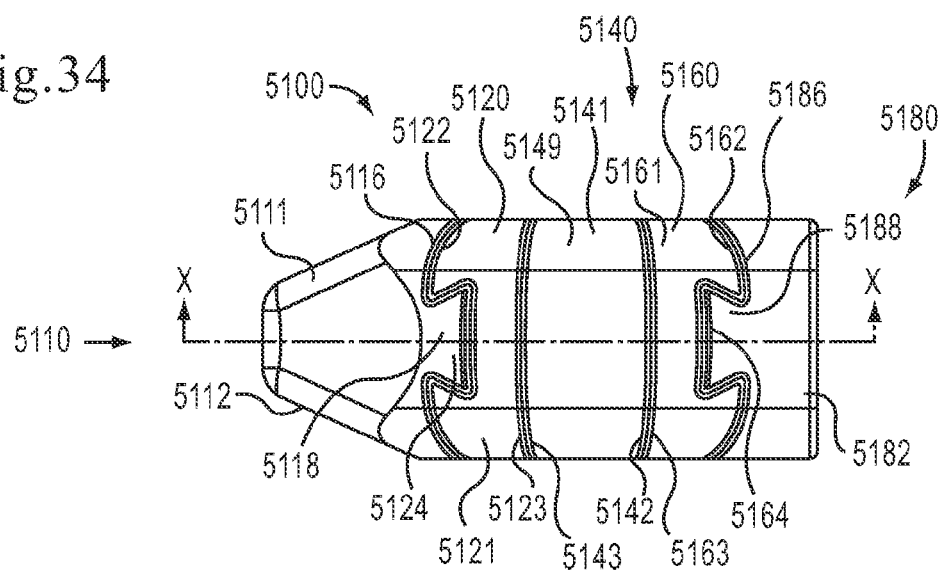
FIG. 34 is a top view of the implant shown in FIG. 31 in the first configuration.
Figure 35:
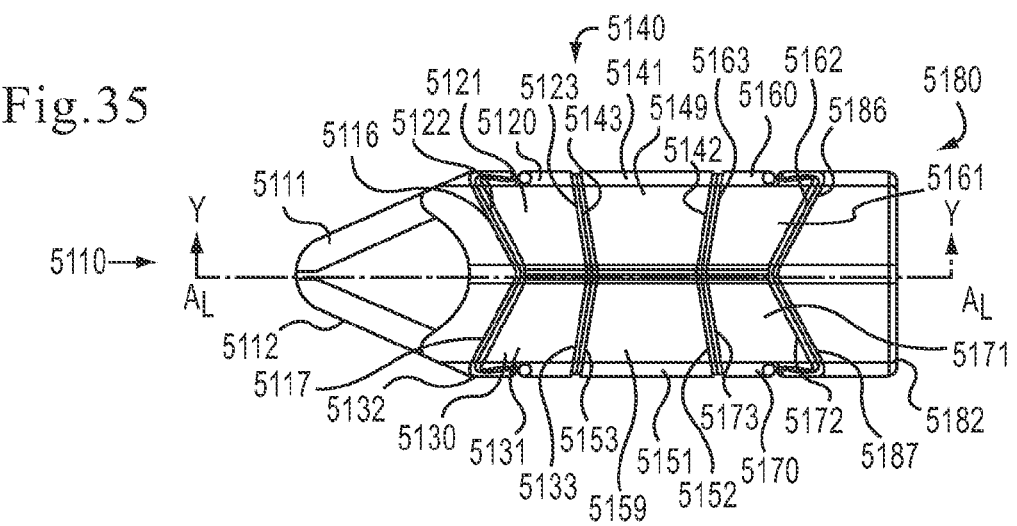
FIG. 35 is a side view of the implant shown in FIG. 31 in the first configuration.
Figure 36:
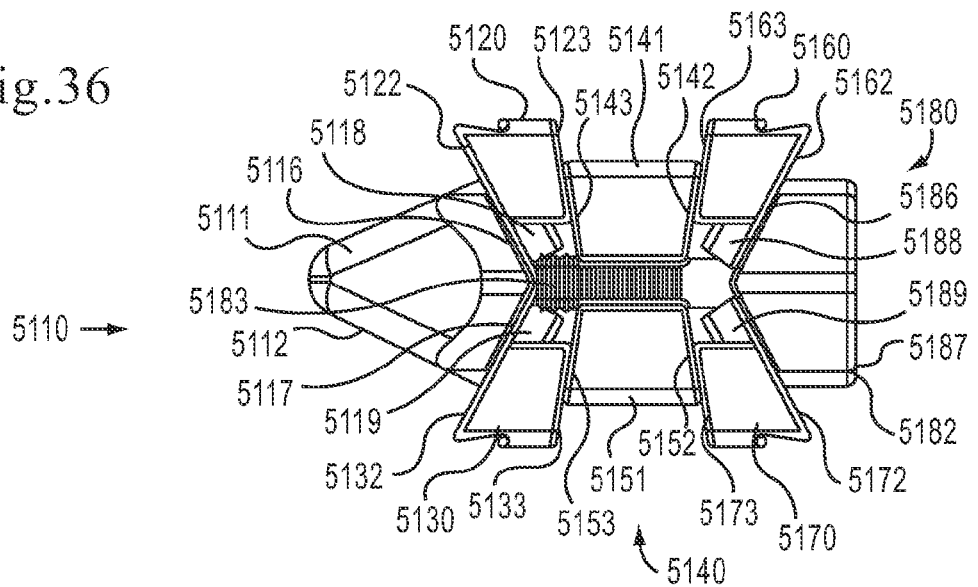
FIG. 36 is a side view of the implant shown in FIG. 32 in the second configuration.

FIG. 28 is a cross-sectional view of the implant illustrated in FIG. 24, taken along line X-X in FIG. 24. The first distal stabilizing groove (not shown in FIG. 28) and the second distal stabilizing groove 4149 of the central portion 4140 are configured to receive the first stabilization pin 4113 and the second stabilization pin 4115 of the actuator 4111 respectively. Likewise, the first proximal stabilizing groove 4144 and the second proximal stabilizing groove (not shown in FIG. 28) of the central portion 4140 are configured to receive the first stabilization pin 4181 and the second stabilization pin 4185 of the tool engagement member 4182 respectively. This configuration prevents the proximal end portion 4180 and the distal end portion 4110 from rotating with respect to the central portion 4140.

Implant 4100 has a first configuration and a second configuration. FIG. 24 shows the implant 4100 in a first configuration. When the implant 4100 is in the first configuration, the proximal end portion 4180, the distal end portion 4110 and the central portion 4140 are substantially coaxial (i.e., substantially share a common longitudinal axis). Said another way, when the implant 4100 is in the first configuration, the outer surface 4121 of the first distal retention member 4120 and the outer surface 4161 of the first proximal retention member 4160 are substantially aligned with the outer surface 4141 of the central portion 4140. Said another way, the outer surface 4121 of the first distal retention member 4120, the outer surface 4161 of the first proximal retention member 4160, and the outer surface 4141 of the central portion 4140 form a substantially continuous surface. Similarly, the outer surface 4131 of the second distal retention member 4130 and the outer surface 4171 of the second proximal retention member 4170 are similarly aligned with the outer surface 4141 of the central portion 4140 when the implant 4100 is in the first configuration.

The implant 4100 can be moved between the first configuration and the second configuration as illustrated in FIG. 25. To move the implant 4100 from the first configuration to the second configuration, the drive screw 4183 is rotated. When the drive screw 4183 is rotated as indicated by the arrow CC in FIG. 24, the drive screw 4183 pulls the actuator 4111 and the tool engagement member 4182 toward the central portion 4140. The first engagement surface 4116 of the actuator 4111 exerts an axial force on the first engagement surface 4122 of the first distal retention member 4120 and the second engagement surface 4117 of the actuator 4111 exerts an axial force on the first engagement surface 4132 of the second distal retention member 4130. Because the first engagement surface 4116 of the actuator 4111 is at an acute angle with respect to the longitudinal axis $A_L$, a component of the axial force transmitted via the first engagement surface 4116 of the actuator 4111 to the first engagement surface 4122 of the first distal retention member 4120 has a direction as shown by the arrow AA in FIG. 25. Similarly, because the second engagement surface 4117 of the actuator 4111 is at an acute angle with respect to the longitudinal axis $A_L$, a component of the axial force transmitted via the second engagement surface 4117 of the actuator 4111 to the first engagement surface 4132 of the second distal retention member 4130 has a direction as shown by the arrow BB in FIG. 25. Said another way, a component of the forces exerted by the actuator 4111 on the first distal retention member 4120 and the second distal retention member 4130 has a direction that is substantially normal to the longitudinal axis $A_L$. These forces cause the first distal retention member 4120 to slide on the first engagement surface 4116 of the actuator 4111 causing the first distal retention member 4120 to move in the direction AA and the second distal retention member 4130 to slide on the second engagement surface 4117 of the actuator 4111 causing the second distal retention member 4130 to move in the direction BB.

Similarly, when the drive screw 4183 is rotated as indicated by the arrow CC in FIG. 24, the first engagement surface 4186 of the tool engagement member 4182 exerts an axial force on the first engagement surface 4182 of the first proximal retention member 4160 and the second engagement surface 4187 of the tool engagement member 4182 exerts an axial force on the first engagement surface 4172 of the second proximal retention member 4170. Because the first engagement surface 4186 of the tool engagement member 4182 is at an acute angle with respect to the longitudinal axis $A_L$, a component of the axial force transmitted via the first engagement surface 4186 of the tool engagement member 4182 to the first engagement surface 4162 of the first proximal retention member 4160 has a direction as shown by the arrow AA in FIG. 25. Similarly, because the second engagement surface 4187 of the tool engagement member 4182 is at an acute angle with respect to the longitudinal axis $A_L$, a component of the axial force transmitted via the second engagement surface 4187 of the tool engagement member 4182 to the first engagement surface 4172 of the second proximal retention member 4170 has a direction as shown by the arrow BB in FIG. 25. Said another way, a component of the forces exerted by the tool engagement member 4182 on the first proximal retention member 4160 and the second proximal retention member 4170 has a direction that is substantially normal to the longitudinal axis $A_L$. These forces cause the first proximal retention member 4160 to slide on the first engagement surface 4186 of the tool engagement member 4182 causing the first proximal retention member 4160 to move in the direction AA and the second proximal retention member 4170 to slide on the second engagement surface 4187 of the tool engagement member 4182 causing the second proximal retention member 4170 to move in the direction BB. The dovetail configuration of the grooves 4124, 4134, 4164, 4174 of the retention members 4120, 4130, 4160, 4170 prevents the retention members 4120, 4130, 4160, 4170 from sliding past the second configuration.

When the implant 4100 is in the second configuration the first distal retention member 4120, the second distal retention member 4130, the first proximal retention member 4160 and/or the second proximal retention member 4170 are offset from the central portion 4140 in a direction substantially normal to the longitudinal axis $A_L$. Said another way, the outer surface 4121 of the first distal retention member 4120 and/or the outer surface 4161 of the first proximal retention member 4160 are not aligned with the outer surface 4141 of the central portion 4140 and are discontinuous with the outer surface 4141 of the central portion 4140. Similarly, the outer surface 4131 of the second distal retention member 4130 and the outer surface 4171 of the second proximal retention member 4170 are similarly situated with respect to the outer surface 4141 of the central portion 4140 when the implant 4100 is in the second configuration.

As described above, when the implant 4100 is positioned between the spinous processes, the implant 4100 can be moved from the first configuration to the second configuration. In the second configuration, the first distal retention member 4120 and the first proximal retention member 4160 are offset from the central portion 4140 to limit lateral movement of the implant 4100 with respect to the spinous processes. Said another way, the first distal retention member 4120, the first proximal retention member 4160 and the central portion 4140 form a saddle, within which a first spinous process can be disposed. Similarly, in the second configuration, the second distal retention member 4130 and the second proximal retention member 4170 are offset from the central portion 4140 to limit lateral movement of the implant 4100 with respect to the spinous processes. Said another way, the second distal retention member 4130, the second proximal retention member 4170 and the central portion 4140 form a saddle, within which a second spinous process can be disposed.

FIGS. 31-44 show an implant 5100, according to an embodiment. Implant 5100 includes a distal end portion 5110, a central portion 5140 and a proximal end portion 5180. The central portion 5140 is coupled between the distal end portion 5110 and the proximal end portion 5180. The implant 5100 defines a lumen 5146 and includes a drive screw 5183 disposed within the lumen 5146 (see FIG. 37). The drive screw 5183 has a tool head 5184 configured to mate with and/or receive a tool for rotating the drive screw 5183, as further described herein.

Distal end portion 5110 of implant 5100 includes an actuator 5111, a first distal retention member 5120 and a second distal retention member 5130. Actuator 5111 includes a tapered surface 5112, a threaded portion 5114 (see FIG. 37), a first engagement surface 5116, a second engagement surface 5117, a first protrusion 5118 and a second protrusion 5119. The threaded portion 5114 is disposed fixedly within the lumen 5146 and is configured to receive the drive screw 5183. In other embodiments, the actuator 5111 can include a captive nut configured to receive the drive screw 5183.

The first engagement surface 5116 of the actuator 5111 is angularly offset from the longitudinal axis $A_L$ of the implant 5100 by an angle between 0 degrees and 90 degrees. The first engagement surface 5116 includes a first protrusion 5118 having a trapezoidal cross-sectional shape. In this embodiment, the first protrusion 5118 is a dovetail protrusion. As described in more detail below, the first distal retention member 5120 is maintained in sliding contact with the actuator 5111 via the first protrusion 5118.

The second engagement surface 5117 of the actuator 5111 is angularly offset from the longitudinal axis $A_L$ of the implant 5100 by an angle between 0 degrees and 90 degrees. The second engagement surface 5117 includes a second protrusion 5119 having a trapezoidal cross-sectional shape. In this embodiment, the second protrusion 5119 is a dovetail protrusion. As described in more detail below, the second distal retention member 5130 is maintained in sliding contact with the actuator 5111 via the second protrusion 5119.

The first distal retention member 5120 includes an outer surface 5121, a first engagement surface 5122, a second engagement surface 5123 opposite the first engagement surface 5122, and a protrusion 5126. The first distal retention member 5120 defines a notch 5128 (see FIG. 42) configured to allow the drive screw 5183 to pass through the first distal retention member 5120 when the implant 5100 is in the first configuration. Said another way, when the implant 5100 is in the first configuration, the notch 5128 is aligned with the lumen 5146.

The protrusion 5126 has a trapezoidal cross-sectional shape and is configured to be received within a groove of the first support member 5141. In this embodiment, the second protrusion 5126 is a dovetail protrusion. In this manner, the first distal retention member 5120 is maintained in sliding contact with the first support member 5141 via the protrusion 5126. Additionally, the protrusion 5126 of the first distal retention member 5120 is configured to engage a portion of the first support member 5141 (see e.g., FIG. 33) to limit movement of the first distal retention member 5120 relative to the first support member 5141 and/or move the first support member 5141 in a direction normal to the longitudinal axis $A_L$.

The first engagement surface 5122 of the first distal retention member 5120 defines a plane that is angularly offset from the longitudinal axis $A_L$ of the implant 5100 by an angle between 90 degrees and 180 degrees. Moreover, the first engagement surface 5122 of the first distal retention member 5120 is substantially parallel to the first engagement surface

5116 of the actuator 5111. Accordingly, the first distal retention member 5120 is slidably disposed against the actuator 5111.

The first engagement surface 5122 of the first distal retention member 5120 defines a groove 5124. The groove 5124 has a trapezoidal cross-sectional shape. In this embodiment, the groove 5124 has a dovetail shape that corresponds to the shape of the first protrusion 5118 of the actuator 5111. The groove 5124 is configured to slidingly receive the first protrusion 5118 of the actuator 5111. The undercut of the first protrusion 5118 of the actuator 5111 slidably maintains the first protrusion 5118 of the actuator 5111 within the groove 5124. The groove 5124 of the first engagement surface 5122 and the first protrusion 5118 of the actuator 5111 collectively allow movement of the first distal retention member 5120, with respect to the actuator 5111, in a direction substantially parallel to the first engagement surface 5122 of the first distal retention member 5120. Moreover, the groove 5124 of the first engagement surface 5122 and the first protrusion 5118 of the actuator 5111 collectively limit movement of the first distal retention member 5120, with respect to the actuator 5111, in a direction substantially normal to the first engagement surface 5122 of the first distal retention member 5120. The first engagement surface 5122 of the first distal retention member 5120 contacts and is configured to slide along the first engagement surface 5116 of the actuator 5111 when the groove 5124 slides along the first protrusion 5118 of the actuator 5111.

The second engagement surface 5123 of the first distal retention member 5120 is substantially parallel to the distal engagement surface 5143 of the first support member 5141 of the central portion 5140, and defines a plane that is angularly offset from the longitudinal axis $A_L$ of the implant 5100 by an angle between 0 degrees and 90 degrees. Moreover, the angular offset of the second engagement surface 5123 of the first distal retention member 5120 is different than the angular offset of the first engagement surface 5122 of the first distal retention member 5120. Accordingly, the first distal retention member 5120 is slidably disposed against the first support member 5141 of the central portion 5140.

The second distal retention member 5130 includes an outer surface 5131, a first engagement surface 5132, a second engagement surface 5133 opposite the first engagement surface 5132, and a protrusion 5136. The second distal retention member 5130 defines a notch 5138 configured to allow the drive screw 5183 to pass the second distal retention member 5130 when the implant 5100 is in the first configuration. Moreover, the first engagement surface 5132 of the second distal retention member 5130 defines a groove 5134. The second distal retention member 5130 is configured similar to the first distal retention member 5120, and is therefore not described in detail.

The proximal end portion 5180 of implant 5100 includes a tool engagement member 5182, a first proximal retention member 5160 and a second proximal retention member 5170. Tool engagement member 5182 is configured to mate with and/or receive an insertion tool, such as those described in U.S. patent application Ser. No. 12/182,425 entitled "Tools and Methods for insertion and Removal of Medical Implants," which is incorporated herein by reference in its entirety. In some embodiments, for example, an insertion tool can be coupled to an outer surface of the tool engagement member 5182. In such embodiments, the outer surface of the tool engagement member 5182 can be configured to facilitate the docking of the insertion tool (not shown) to the implant 5100. For example, in some embodiments, the outer surface of the tool engagement member 5182 can include a lead-in chamfer, a tapered portion and/or a beveled edge to facilitate the docking of the insertion tool onto the tool engagement member 5182 of the implant 5100. Tool engagement member 5182 includes a first engagement surface 5186, a second engagement surface 5187, a first protrusion 5188, a second protrusion 5189 and a cap 5185. The cap 5185 is configured to hold the drive screw 5183 in place, preventing axial movement of the drive screw 5183.

The first engagement surface 5186 of the tool engagement member 5182 is angularly offset from the longitudinal axis $A_L$ of the implant 5100 by an angle between 0 degrees and 90 degrees. Said another way, the first engagement surface 5186 of the tool engagement member 5182 is angularly offset from the longitudinal axis $A_L$ of the implant 5100 by an acute angle. As described in more detail herein, the angular offset of the first engagement surface 5186 is associated with moving the implant 5100 between a first configuration (FIG. 31) and a second configuration (FIG. 32).

The first protrusion 5188 of the tool engagement member 5182 has an undercut such that the first proximal retention member 5160 can be slidably coupled to the tool engagement member 5182. The first protrusion 5188 has a trapezoidal cross-sectional shape. In this embodiment, the first protrusion 5188 is a dovetail protrusion.

The second engagement surface 5187 of the tool engagement member 5182 is similar to the first engagement surface 5186 of the tool engagement member 5182. The second protrusion 5189 of the tool engagement member 5182 has an undercut such that the second proximal retention member 5170 can be slidably coupled to the tool engagement member 5182. The second protrusion 5189 has a trapezoidal cross-sectional shape. In this embodiment, the second protrusion 5189 is a dovetail protrusion.

The first proximal retention member 5160 includes an outer surface 4161, a first engagement surface 5162, a second engagement surface 5163 opposite the first engagement surface 5162, and a protrusion 5166. The protrusion 5166 of the first proximal retention member 5160 has an undercut such that the first support member 5141 of the central portion 5140 can be slidably coupled to the first proximal retention member 5160. The protrusion 5166 has a trapezoidal cross-sectional shape. In this embodiment, the protrusion 5166 is a dovetail protrusion. The first proximal retention member 5160 defines a notch 5168 configured to allow the drive screw 5183 to pass through the first proximal retention member 5160 when the implant 5100 is in the first configuration. Said another way, when the implant 5100 is in the first configuration, the notch 5168 is aligned with the lumen 5146.

The first engagement surface 5162 of the first proximal retention member 5160 defines a plane that is angularly offset from the longitudinal axis $A_L$ of the implant 5100 by an angle between 90 degrees and 180 degrees. Said another way, the first engagement surface 5162 of the first proximal retention member 5160 defines a plane that is angularly offset from the longitudinal axis $A_L$ by an obtuse angle. Moreover, the first engagement surface 5162 of the first proximal retention member 5120 is substantially parallel to the first engagement surface 5186 of the tool engagement member 5182. Said another way, the angular offset of the first engagement surface 5162 of the first proximal retention member 5160 is supplementary with the angular offset of the first engagement surface 5186 of the tool engagement member 5182. Accordingly, the first proximal retention member 5160 is slidably disposed against the tool engagement member 5182.

Moreover, the first engagement surface 5162 of the first proximal retention member 5160 defines a groove 5164. The groove 5164 has a trapezoidal cross-sectional shape. In this embodiment, the groove 5164 has a dovetail shape that corresponds to the shape of the first protrusion 5188 of the tool engagement member 5182. The groove 5164 is configured to slidingly receive the first protrusion 5188 of the tool engagement member 5182. The undercut of the first protrusion 5188 of the tool engagement member 5182 slidably maintains the first protrusion 5188 of the tool engagement member 5182 within the groove 5164. The groove 5164 of the first engagement surface 5162 and the first protrusion 5188 of the tool engagement member 5182 collectively allow movement of the first proximal retention member 5160, with respect to the central portion 5140, in a direction substantially parallel to the second engagement surface 5163 of the first proximal retention member 5160. Moreover, the groove 5164 of the first engagement surface 5162 and the first protrusion 5188 of the tool engagement member 5182 collectively limit movement of the first proximal retention member 5160, with respect to the central portion 5140, in a direction substantially normal to the second engagement surface 5163 of the first proximal retention member 5160. The first engagement surface 5162 of the first proximal retention member 5160 contacts and is configured to slide along the first engagement surface 5186 of the tool engagement member 5182 when the groove 5164 slides along the first protrusion 5188 of the tool engagement member 5182.

The second engagement surface 5163 of the first proximal retention member 5160 is substantially parallel to the proximal engagement surface 5142 of the first support member 5141 of the central portion 5140, and defines a plane that is angularly offset from the longitudinal axis $A_L$ of the implant 5100 by an angle between 0 degrees and 90 degrees. Moreover, the angular offset of the second engagement surface 5163 of the first proximal retention member 5160 is supplementary with the angular offset of the proximal engagement surface 5142 of the first support member 5141 of the central portion 5140. Accordingly, the first proximal retention member 5160 is slidably disposed against the first support member 5141 of the central portion 5140. In other embodiments, the plane defined by the second engagement surface 5163 of the first proximal retention member 5160 can be normal to the longitudinal axis $A_L$ of the implant 5100.

The second proximal retention member 5170 includes an outer surface 4171, a first engagement surface 5172, a second engagement surface 5173 opposite the first engagement surface 5172, and a protrusion 5176. The protrusion 5176 of the second proximal retention member 5170 has an undercut such that the second support member 5151 of the central portion 5140 can be slidably coupled to the second proximal retention member 5170. The protrusion 5176 has a trapezoidal cross-sectional shape. In this embodiment, the protrusion 5176 is a dovetail protrusion. Additionally, the second proximal retention member 5170 defines a notch 5178 configured to allow the drive screw 5183 to pass through the second proximal retention member 5170 when the implant 5100 is in the first configuration. Moreover, the first engagement surface 5172 of the second proximal retention member 5170 defines a groove 5174. The second proximal retention member 5170 is configured similar to the first proximal retention member 5160.

The central portion 5140 of implant 5100 includes a first support member 5141 and a second support member 5151. The first support member 5141 includes an outer surface 5149, a proximal engagement surface 5142, and a distal engagement surface 5143. The first support member 5141 defines a notch 5148 (see FIG. 41) configured to allow the drive screw 5183 to pass through the first support member 5141 when the implant 5100 is in the first configuration. Said another way, when the implant 5100 is in the first configuration, the notch 5148 is aligned with the lumen 5146.

The distal engagement surface 5143 of the first support member 5141 defines a plane that is angularly offset from the longitudinal axis $A_L$ of the implant 5100 by an angle between 90 degrees and 180 degrees. Moreover, the angular offset of the distal engagement surface 5143 of the first support member 5141 is supplementary with the angular offset of the second engagement surface 5123 of the first distal retention member 5120. Accordingly, the first support member 5141 is slidably disposed against the first distal retention member 5120.

Moreover, the distal engagement surface 5143 of the first support member 5141 defines a distal groove 5145. The distal groove 5145 is configured to slidingly receive the protrusion 5126 of the first distal retention member 5120. The undercut of the protrusion 5126 of the first distal retention member 5120 slidably maintains the protrusion 5126 of the first distal retention member 5120 within the distal groove 5145. The distal engagement surface 5143 of the first support member 5141 contacts and is configured to slide along the second engagement surface 5123 of the first distal retention member 5120 when the distal groove 5145 slides along the protrusion 5126 of the first distal retention member 5120.

The proximal engagement surface 5142 of the first support member 5141 defines a plane that is angularly offset from the longitudinal axis $A_L$ of the implant 5100 by an angle between 90 degrees and 180 degrees. Moreover, the angular offset of the proximal engagement surface 5142 of the first support member 5141 is supplementary with the angular offset of the second engagement surface 5163 of the first proximal retention member 5160. Accordingly, the first support member 5141 is slidably disposed against the first proximal retention member 5160.

Moreover, the proximal engagement surface 5142 of the first support member 5141 defines a proximal groove 5144. The proximal groove 5144 is configured to slidingly receive the protrusion 5166 of the first proximal retention member 5160. The undercut of the protrusion 5166 of the first proximal retention member 5160 slidably maintains the protrusion 5166 of the first proximal retention member 5160 within the proximal groove 5144. The proximal engagement surface 5142 of the first support member 5141 contacts and is configured to slide along the second engagement surface 5163 of the first proximal retention member 5160 when the proximal groove 5144 slides along the protrusion 5166 of the first proximal retention member 5160.

Likewise, the second support member 5151 of the central portion 5140 includes an outer surface 5159, a proximal engagement surface 5152, and a distal engagement surface 5153. The second support member 5151 defines a notch 5156 configured to allow the drive screw 5183 to pass through the second support member 5151 when the implant 5100 is in the first configuration. The proximal engagement surface 5152 defines a proximal groove 5154 and the distal engagement surface 5153 defines a distal groove 5155. The second support member 5151 is configured similar to the first support member 5141.

Implant 5100 has a first configuration and a second configuration. FIG. 31 shows the implant 5100 in a first configuration. When the implant 5100 is in the first configuration, the proximal end portion 5180, the distal end portion 5110 and the central portion 5140 are substantially coaxial (i.e., substantially share a common longitudinal axis). Said another way, when the implant 5100 is in the first configuration, the outer surface 5121 of the first distal retention member 5120 and the outer surface 5161 of the first proximal retention member 5160 are substantially aligned with the outer surface 5149 of the first support member 5141 of the central portion 5140. Said another way, the outer surface 5121 of the first distal retention member 5120, the outer surface 5161 of the first proximal retention member 5160, and the outer surface 5149 of the first support member 5141 of the central portion 5140 form a substantially continuous surface. Said yet another way, the outer surface 5121 of the first distal retention member 5120 and the outer surface 5161 of the first proximal retention member 5160 are flush with the outer surface 5149 of the first support member 5141 of the central portion 5140. Similarly, the outer surface 5131 of the second distal retention member 5130 and the outer surface 5171 of the second proximal retention member 5170 are similarly aligned with the outer surface 5159 of the second support member 5151 of the central portion 5140 when the implant 5100 is in the first configuration.

The implant 5100 can be moved between the first configuration and the second configuration as illustrated in FIG. 32. To move the implant 5100 from the first configuration to the second configuration, the drive screw 5183 is rotated. When the drive screw 5183 is rotated as indicated by the arrow CC in FIG. 31, the drive screw 5183 pulls the actuator 5111 and the tool engagement member 5182 toward the central portion 5140. The first engagement surface 5116 of the actuator 5111 exerts an axial force on the first engagement surface 5122 of the first distal retention member 5120 and the second engagement surface 5117 of the actuator 5111 exerts an axial force on the first engagement surface 5132 of the second distal retention member 5130. Because the first engagement surface 5116 of the actuator 5111 is at an acute angle with respect to the longitudinal axis $A_L$, a component of the axial force transmitted via the first engagement surface 5116 of the actuator 5111 to the first engagement surface 5122 of the first distal retention member 5120 has a direction as shown by the arrow AA in FIG. 31. Similarly, because the second engagement surface 5117 of the actuator 5111 is at an acute angle with respect to the longitudinal axis $A_L$, a component of the axial force transmitted via the second engagement surface 5117 of the actuator 5111 to the first engagement surface 5132 of the second distal retention member 5130 has a direction as shown by the arrow BB in FIG. 31. Said another way, a component of the forces exerted by the actuator 5111 on the first distal retention member 5120 and the second distal retention member 5130 has a direction that is substantially normal to the longitudinal axis $A_L$. These forces cause the first distal retention member 5120 to slide on the first engagement surface 5116 of the actuator 5111 causing the first distal retention member 5120 to move in the direction AA and the second distal retention member 5130 to slide on the second engagement surface 5117 of the actuator 5111 causing the second distal retention member 5130 to move in the direction BB.

Similarly, when the drive screw 5183 is rotated as indicated by the arrow CC in FIG. 31, the first engagement surface 5186 of the tool engagement member 5182 exerts an axial force on the first engagement surface 5182 of the first proximal retention member 5160 and the second engagement surface 5187 of the tool engagement member 5182 exerts an axial force on the first engagement surface 5172 of the second proximal retention member 5170. Because the first engagement surface 5186 of the tool engagement member 5182 is at an acute angle with respect to the longitudinal axis $A_L$, a component of the axial force transmitted via the first engagement surface 5186 of the tool engagement member 5182 to the first engagement surface 5162 of the first proximal retention member 5160 has a direction as shown by the arrow AA in FIG. 31. Similarly, because the second engagement surface 5187 of the tool engagement member 5182 is at an acute angle with respect to the longitudinal axis $A_L$, a component of the axial force transmitted via the second engagement surface 5187 of the tool engagement member 5182 to the first engagement surface 5172 of the second proximal retention member 5170 has a direction as shown by the arrow BB in FIG. 31. Said another way, a component of the forces exerted by the tool engagement member 5182 on the first proximal retention member 5160 and the second proximal retention member 5170 has a direction that is substantially normal to the longitudinal axis $A_L$. These forces cause the first proximal retention member 5160 to slide on the first engagement surface 5186 of the tool engagement member 5182 causing the first proximal retention member 5160 to move in the direction AA and the second proximal retention member 5170 to slide on the second engagement surface 5187 of the tool engagement member 5182 causing the second proximal retention member 5170 to move in the direction BB.

As the first proximal retention member 5160 and the first distal retention member 5120 move in direction AA, the protrusions 5166, 5126 of the first proximal retention member 5160 and the first distal retention member 5120, respectively, contact the upper surface of the proximal groove 5144 and the distal groove 5145 of the first support member 5141 respectively, causing the first support member 5141 to move in the direction AA. In the second configuration, as seen in FIG. 33, the first support member 5141 is displaced from its position in the first configuration in the direction AA. Likewise, as the second proximal retention member 5170 and the second distal retention member 5130 move in direction BB, the protrusions 5176, 5136 of the second proximal retention member 5170 and the second distal retention member 5130, respectively, contact the upper surface of the proximal groove 5154 and the distal groove 5155 of the second support member 5151 respectively, causing the second support member 5151 to move in the direction BB. In the second configuration, as seen in FIG. 33, the second support member 5151 is displaced from its position in the first configuration in the direction BB. In this manner, the first support member 5141 and the second support member 5151 can distract the adjacent spinous processes.

When the implant 5100 is in the second configuration the first distal retention member 5120, the second distal retention member 5130, the first proximal retention member 5160 and/or the second proximal retention member 5170 are offset from the central portion 5140. Said another way, the outer surface 5121 of the first distal retention member 5120 and/or the outer surface 5161 of the first proximal retention member 4160 are not aligned with the outer surface 5149 of the first support member 5141 of the central portion 5140 and are discontinuous with the outer surface 5149 of the first support member 5141 of the central portion 5140. Similarly, the outer surface 5131 of the second distal retention member 5130 and the outer surface 5171 of the second proximal retention member 5170 are similarly situated with respect to the outer surface 5159 of the second support member 5151 of the central portion 5140 when the implant 5100 is in the second configuration. Moreover, when the implant is in the second configuration, the first support member 5141 of the central portion 5140 and the second support member 5151 of the central portion 5140 are offset from the longitudinal axis $A_L$ in a direction substantially normal to the longitudinal axis $A_L$.

In use, implant 5100 is inserted percutaneously between a pair of adjacent spinous processes (not shown in FIGS. 31-44), in the first configuration. For example, a medical practitioner can insert the implant 5100 percutaneously (e.g., through a cannula, over a guide wire, or the like) into a body of a patient. An insertion tool, such as those described in U.S. patent application Ser. No. 12/182,425 entitled "Tools and Methods for insertion and Removal of Medical Implants," which is incorporated herein by reference in its entirety, can be used to insert the implant 5100 into a body of a patient. The insertion tool is configured to be removably coupled to the tool engagement member 5182. In this manner, the insertion tool retains the implant 5100. Said another way, the insertion tool limits the rotational movement of the implant 5100, with respect to the insertion tool, about the longitudinal axis $A_L$ and limits the axial movement of the implant 5100, with respect to the insertion tool, about the longitudinal axis $A_L$. The insertion tool has an actuator configured to be inserted into the tool head 5184 of the drive screw 5183. The actuator of the insertion tool is configured to rotate the drive screw 5183 about the longitudinal axis $A_L$, without rotating the other components of the implant 5100. Said another way, the insertion tool limits rotational movement of the tool engagement member 5182 while rotating the drive screw 5183 about the longitudinal axis $A_L$.

When inserting the implant 5100 into a body of a patient, the distal end portion 5110 is inserted first and is moved past the spinous processes until the central portion 5140 is positioned between the spinous processes. In this manner, the central portion 5140 of the implant 5100 can distract and/or maintain a minimal spacing between the adjacent spinous processes. The distance between the top surface and the bottom surface of the central portion 5140 can be slightly smaller than the space between the spinous processes to account for surrounding ligaments and tissue. Similar to implant 100, in some embodiments, the central portion 5140 in its first configuration directly contacts the spinous processes between which it is positioned.

Once between the spinous processes, the implant 5100 can be moved from the first configuration to the second configuration. In the second configuration, the first and second proximal retention members 5160, 5170 and the first and second distal retention members 5120, 5130 are offset from the actuator 5111 and the tool engagement member 5182, and positioned to limit lateral movement of the implant 5100 with respect to the spinous processes. Said another way, the first distal retention member 5120, the first proximal retention member 5160 and the central portion 5140 form a saddle, within which a first spinous process can be disposed. Similarly, the second distal retention member 5130, the second proximal retention member 5170 and the central portion 5140 form a saddle, within which a second spinous process can be disposed. The first and second proximal retention members 5160, 5170 and the first and second distal retention members 5120, 5130 can also further distract the spinous processes. The proximal retention member 5160 and the distal retention member 5120 are configured to engage the superior spinous processes (i.e., either directly or through surrounding tissue) and the second proximal retention member 5170 and the second distal retention member 5130 are configured to engage the inferior spinous process (i.e., either directly or through surrounding tissue) in the second configuration. Additionally, in the second configuration, the first support member 5141 of the central portion 5140 and the second support member 5151 of the central portion are offset from the actuator 5111 and the tool engagement member 5182 and positioned to distract the spinous processes. Once in the second configuration, the implant 5100 can be released from the insertion tool and the insertion tool can be removed from the patient's body.

To remove from and/or reposition the implant 5100 within the body, the drive screw 5183 is rotated as indicated by the arrow DD in FIG. 31, by for example, a removal tool (may be similar to an insertion tool). Rotating the drive screw in direction DD, causes the dovetail configuration of the protrusions 5118, 5119 of the insertion member 1111 and the dovetail configurations of the protrusions 5188, 5189 of the tool engagement member 5182 to pull the distal retention members 5120, 5130 and the proximal retention members 5160, 5170 back into the first configuration. This causes the dovetail configurations of the protrusions 5126, 5136 of the distal retention members 5120, 5130 and the dovetail configurations of the protrusions 5166, 5176 of the proximal retention members 5160, 5170 to pull the support members 5141, 5151 back into the first configuration. After the implant 5100 is in the first configuration, a medical practitioner can remove from and/or reposition the implant 5100 within the body.

Although the implant 5100 is shown is being movable between a first configuration (FIG. 31) and a second configuration (FIG. 32), the implant 5100 can be maintained in any number of different configurations. For example, the implant 5100 can be maintained in any suitable configuration between the first configuration and the second configuration. Said another way, the implant 5100 can be placed in an infinite number of different configurations between the first configuration and the second configuration. Thus, the spinous processes can be distracted by the first support member 5141 and the second support member 5151 by any desired amount within a predetermined range. In this manner, a single implant 5100 can be used to treat a wide range of conditions and/or locations within the body requiring different amounts of distraction. Moreover, this arrangement allows the amount of distraction to be varied in situ over time.

For example, in some embodiments, the amount of distraction can be varied within a range of approximately 10 mm to 16 mm. Within this range, the size of the central portion 5140 can be adjusted to any desired amount by rotating the drive screw 5183 a predetermined amount, as described above. In other embodiments, the range of distraction can be approximately 3 mm (e.g., a range from 10 mm to 13 mm, a range from 12 mm to 15 mm, or the like). In yet other embodiments, the range of distraction can be approximately 2 mm (e.g., a range from 10 mm to 12 mm, a range from 12 mm to 14 mm, or the like).

Although the implants shown and described above are configured to be disposed within a space between adjacent spinous processes, in other embodiments an implant can be configured to be disposed within a spinal disc space, for example, to stabilize and/or distract a spinal segment after disc material is removed from the disc space. In some embodiments, for example, an apparatus includes a spacer and an actuator. The spacer has a first spacer member configured to engage an endplate of a first vertebra and a second spacer member configured to engage an endplate of a second vertebra. The second vertebra can be adjacent the first vertebra. The actuator has a first actuator member and a second actuator member coupled to the first actuator member. The first actuator member is matingly and movably coupled to the first spacer member. Similarly, the first actuator is matingly and movably coupled to the second spacer member. The second actuator member is matingly and movably coupled to the first spacer member. Similarly, the second actuator member is matingly and movably coupled to the second spacer member. The actuator is configured to move the spacer between a first configuration and a second configuration. The first spacer member is in contact with the second spacer member when the spacer is in the first configuration. The first spacer member is spaced apart from the second spacer member by a non-zero distance when the spacer is in the second configuration. This arrangement can, for example, allow for the insertion of bone material and/or bone growth enhancing substances between the first spacer member and the second spacer member.

In some embodiments, a disc implant can include one or more components having mating surfaces that are non-parallel to and non-normal to a longitudinal axis of the implant. For example, in some embodiments, a disc implant can include a spacer and an actuator. The spacer defines a longitudinal axis and has a first spacer member and a second spacer member. The first spacer member is configured to engage an endplate of a first vertebra, and has a first surface and a second surface. An axis within a plane defined by the first surface of the first spacer member is non-parallel to and non-normal to the longitudinal axis. An axis within a plane defined by the second surface of the first spacer member is non-parallel to and non-normal to the longitudinal axis. The second spacer member is configured to engage an endplate of a second vertebra, the second vertebra being adjacent the first vertebra. The second spacer member has a first surface and a second surface. An axis within a plane defined by the first surface of the second spacer member is non-parallel to and non-normal to the longitudinal axis. An axis within a plane defined by the second surface of the second spacer member is non-parallel to and non-normal to the longitudinal axis. The actuator has a first actuator member and a second actuator member movably coupled to the first actuator member. A first surface of the first actuator member is in contact with and substantially parallel to the first surface of the first spacer member. A second surface of the first actuator member is in contact with and substantially parallel to the first surface of the second spacer member. A first surface of the second actuator member is in contact with and substantially parallel to the second surface of the first spacer member. A second surface of the second actuator member is in contact with and substantially parallel to the second surface of the second spacer member. The actuator is configured to move the spacer between a first configuration and a second configuration. The first spacer member is in contact with the second spacer member when the spacer is in the first configuration. The first spacer member is spaced apart from the second spacer member by a non-zero distance when the spacer is in the second configuration.

In some embodiments, an apparatus includes a spacer and an actuator. The spacer defines a longitudinal axis and has a first spacer member configured to engage an endplate of a first vertebra, and a second spacer member configured to engage an endplate of a second vertebra. The first spacer member has a first surface and a second surface. The second spacer member has a first surface and a second surface. The actuator has a first actuator member and a second actuator member movably coupled to the first actuator member. A first surface of the first actuator member is matingly and movably coupled to the first surface of the first spacer member. A second surface of the first actuator is matingly and movably coupled to the first surface of the second spacer member. A first surface of the second actuator member is matingly and movably coupled to the second surface of the first spacer member. A second surface of the second actuator member is matingly and movably coupled to the second surface of the second spacer member. The actuator is configured to move the spacer between a first configuration and a second configuration. The spacer has a first size along a first axis substantially normal to the longitudinal axis and a second size along a second axis substantially normal to the longitudinal axis and substantially normal to the first axis. The first size when the spacer is in the second configuration is greater than the first size when the spacer is in the first configuration. The second size when the spacer is in the second configuration is substantially equal to the second size when the spacer is in the first configuration.

Figure 45:
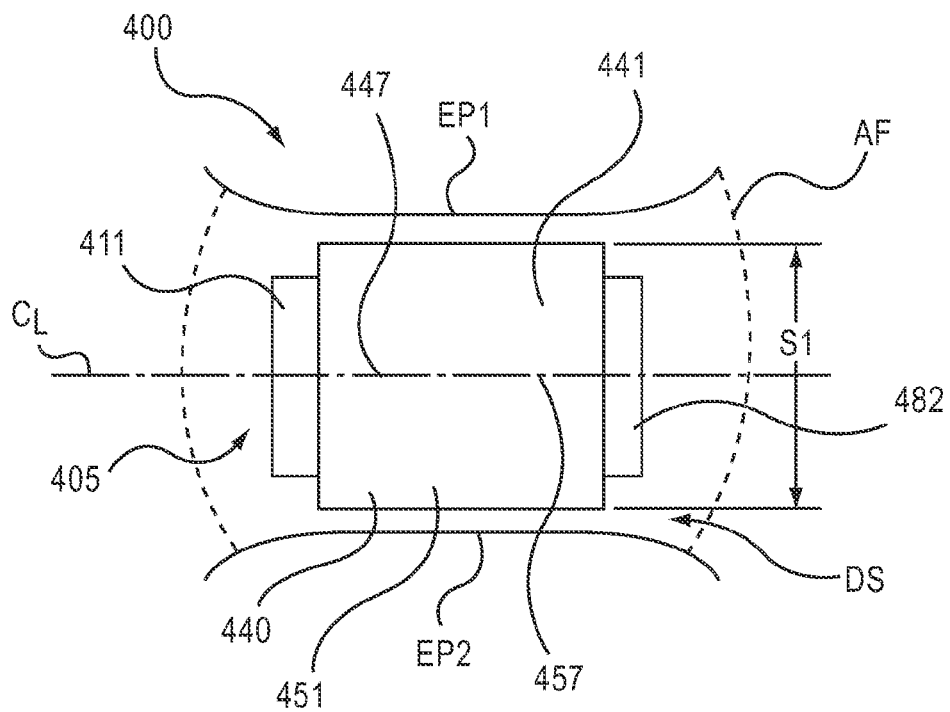
FIGS. 45 and 46 are schematic illustrations of an implant, according to an embodiment in a first configuration and a second configuration, respectively.
Figure 46:
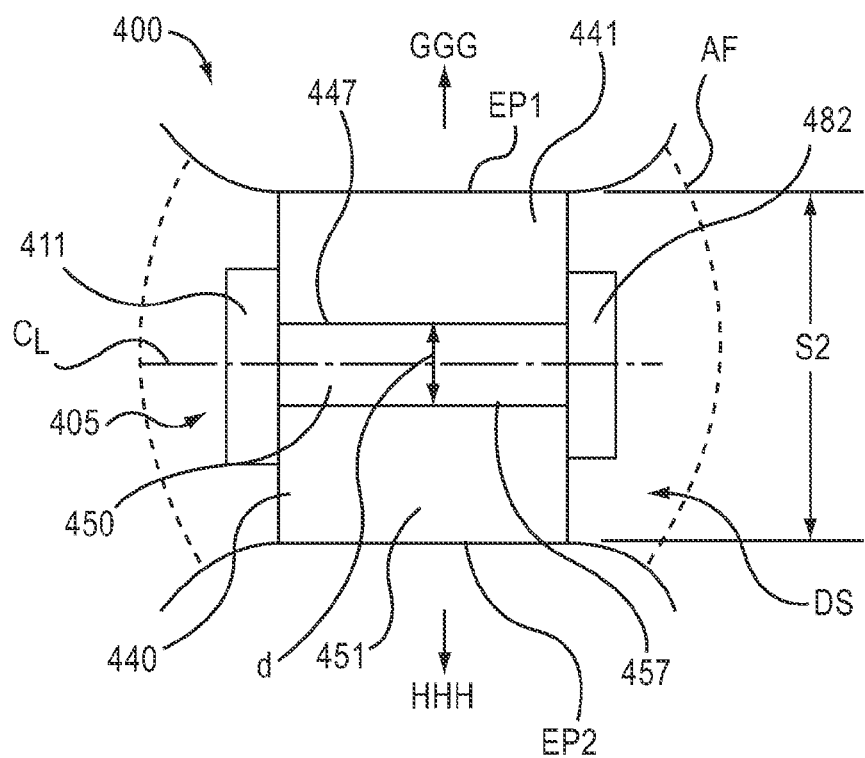

FIGS. 45 and 46 are schematic illustrations of an implant 400 according to an embodiment, in a first configuration and a second configuration, respectively. As shown, the implant 400 is configured to be disposed within a disc space DS. The disc space DS is bounded by a first endplate EP1, a second endplate EP2, and an annulus fibrosis AF of the disc (shown by the dashed lines in FIGS. 45 and 46). The implant 400 includes a spacer 440 and an actuator 405. The spacer 440 has a first spacer member 441 and a second spacer member 451, and defines a center line $C_L$. The center line $C_L$ can be, for example, parallel to a longitudinal axis of the spacer 440. As shown in FIG. 46, the first spacer member 441 is configured to engage the first endplate EP1. Similarly, the second spacer member 551 is configured to engage the second endplate EP2.

The actuator 405 has a first actuator member 411 and a second actuator member 482 coupled to the first actuator member 411. As shown in FIGS. 45 and 46, the first actuator member 411 is matingly and movably coupled to the first spacer member 441 and the second spacer member 451. Similarly, the second actuator member 482 is matingly and movably coupled to the first spacer member 441 and the second spacer member 451. The first actuator member 411 and/or the second actuator member 482 can be matingly coupled to the first spacer member 441 and/or the second spacer member 451 in any suitable manner. For example, in some embodiments, the first actuator member 411 and/or the second actuator member 482 can include a dovetail protrusion and/or dovetail groove, of the types shown and described above, configured to matingly engage a dovetail protrusion and/or dovetail groove of the first spacer member 441 and/or the second spacer member 451. In this manner, the first spacer member 441 and/or the second spacer member 451 can be maintained in movable contact with the first actuator member 411 and/or the second actuator member 482. Similarly stated, such an arrangement allows the first spacer member 441 and/or the second spacer member 451 to remain in sliding contact with the first actuator member 411 and/or the second actuator member 482 over a range of motion. Said another way, such an arrangement prevents movement of the first spacer member 441 and/or the second spacer member 451 in a first direction relative to the first actuator member 411 and/or the second actuator member 482 while allowing movement of the first spacer member 441 and/or the second spacer member 451 in a second direction relative to the first actuator member 411 and/or the second actuator member 482.

The actuator 405 is configured to move the spacer 440 between a first configuration (FIG. 45) and a second configuration (FIG. 46). The actuator 405 can move the spacer 440 between the first configuration and the second configuration by any suitable mechanism. For example, in some embodiments, the actuator 405 can include a biasing member configured to move the spacer 440 between the first configuration and the second configuration. In other embodiments, the actuator 405 can move between a first position and a second position (not shown in FIGS. 45 and 46) to move the spacer 440 between the first configuration and the second configuration. In yet other embodiments, the first actuator member 411 can be configured to move relative to the second actuator member 482 to move the spacer 440 between the first configuration and the second configuration.

As shown in FIG. 45, the first spacer member 441 is in contact with the second spacer member 451 when the spacer 440 is in the first configuration. More particularly, a surface 447 of the first spacer member 441 is in contact with a surface 457 of the second spacer member 451 when the spacer 440 is in the first configuration. Moreover, the spacer 440 has a first size S1 along an axis substantially normal to the center line C$_L$ (e.g., a vertical axis as shown in FIG. 45) when the spacer 440 is in the first configuration.

When the actuator 405 moves the spacer 440 from the first configuration to the second configuration, the first spacer member 441 moves relative to the second spacer member 451 in a direction substantially normal to the center line C$_L$, as shown by the arrow GGG in FIG. 46. Similarly stated, when the actuator 405 moves the spacer 440 from the first configuration to the second configuration, the second spacer member 451 moves relative to the first spacer member 441 in a direction substantially normal to the center line C$_L$, as shown by the arrow HHH in FIG. 46. Said another way, when the actuator 405 moves the spacer 440 from the first configuration to the second configuration, the first spacer member 441 is moved apart from the second spacer member 451.

Accordingly, when the spacer 440 is in the second configuration, the first spacer member 441 is spaced apart from the second spacer member 451 by a non-zero distance. Said another way, a lower portion of the surface 447 of the first spacer member 441 is spaced apart from an upper portion of the surface 457 of the second spacer member 451 by a non-zero distance d when the spacer 440 is in the second configuration. Said yet another way, the first spacer member 441 and the second spacer member 451 collectively define an opening 450 when the spacer 440 is in the second configuration. In this manner, bone material and/or bone growth enhancing substances can be disposed between the first spacer member 441 and the second spacer member 451 (e.g., within the opening 450) when the spacer 440 is in the second configuration. Also, bone growth can occur through the opening 450, promoting better fusion between the end plate EP1 and the end plate EP2.

Moreover, the spacer 440 has a second size S2 along the axis substantially normal to the center line C$_L$, greater than the size S1, when the spacer 440 is in the second configuration. Similarly stated, the size of the spacer 440 along at least one axis is increased when the spacer 440 is moved from the first configuration to the second configuration. Accordingly, in use, the implant 400 can be inserted into the disc space DS when the implant 400 is in the first configuration (see e.g., FIG. 45). For example, a user can insert the implant 400 percutaneously (e.g., through a cannula, over a guide wire, or the like) into a body of a patient. In some embodiments, a tool, such as those described in U.S. patent application Ser. No. 12/182,425 entitled "Tools and Methods for insertion and Removal of Medical Implants," which is incorporated herein by reference in its entirety can be used to insert the implant 400 into a body of a patient and/or actuate the implant 400, as described above.

In some embodiments, the spacer 440 can be repeatedly moved between the first configuration and the second configuration. In this manner, a user can remove the implant 400 from and/or reposition the implant 400 within the body in a minimally-invasive manner.

In use, implant 400 can be inserted percutaneously into a disc space (not shown). In this manner, the implant 400 can be used, for example, as a fusion cage. The implant 400 can be inserted when in the first configuration, by, for example, an insertion tool as shown and described in U.S. patent application Ser. No. 12/182,425 entitled "Tools and Methods for insertion and Removal of Medical Implants," which is incorporated herein by reference in its entirety. Once in the disc space, the implant 400 can be moved from the first configuration to the second configuration. In this manner, the first spacer member 441 and the second spacer member 451 can distract and/or maintain a minimal spacing of the disc space. More particularly, the first spacer member 441 and the second spacer member 451 can contact the vertebral endplates to stabilize the spinal segment within which the implant 400 is disposed.

FIGS. 47-60 show an implant 1200, according to an embodiment. Implant 1200 includes a distal end portion 1210, a central portion 1240 and a proximal end portion 1280. The central portion 1240 is disposed between the distal end portion 1210 and the proximal end portion 1280. The implant 1200 defines a lumen 1246 (see FIG. 54) and includes a drive screw 1283 disposed within the lumen 1246. The drive screw 1283 has a tool head 1284 configured to mate with and/or receive a tool for rotating the drive screw 1283, as described in U.S. patent application Ser. No. 12/182,425 entitled "Tools and Methods for insertion and Removal of Medical Implants," which is incorporated herein by reference in its entirety.

The distal end portion 1210 of implant 1200 includes an actuator 1211, a first distal intermediate member 1220 and a second distal intermediate member 1230. Actuator 1211 includes a tapered surface 1212, a threaded portion 1214 (see FIG. 55), a first engagement surface 1216, a second engagement surface 1217, a first protrusion 1218 and a second protrusion 1219. The threaded portion 1214 is disposed fixedly within the lumen 1246 and is configured to receive the drive screw 1283. In other embodiments, the insertion member can include a captive nut configured to receive the drive screw 1283.

Figure 47:
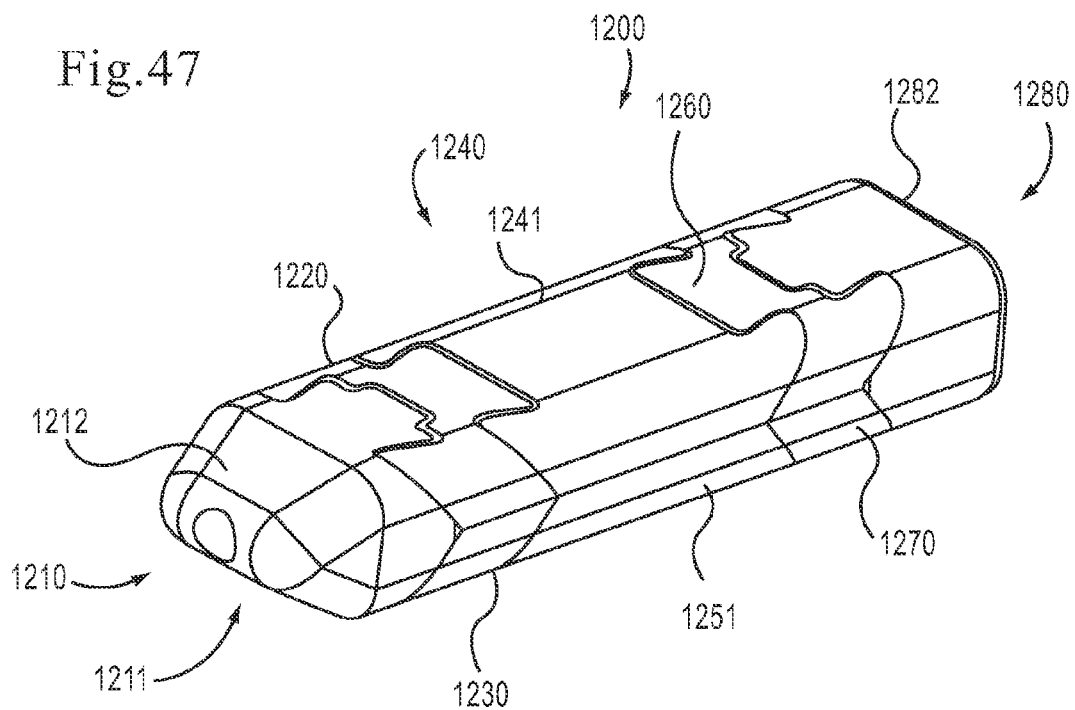
FIGS. 47 and 48 are perspective views of an implant, according to an embodiment in a first configuration and a second configuration, respectively.
Figure 48:
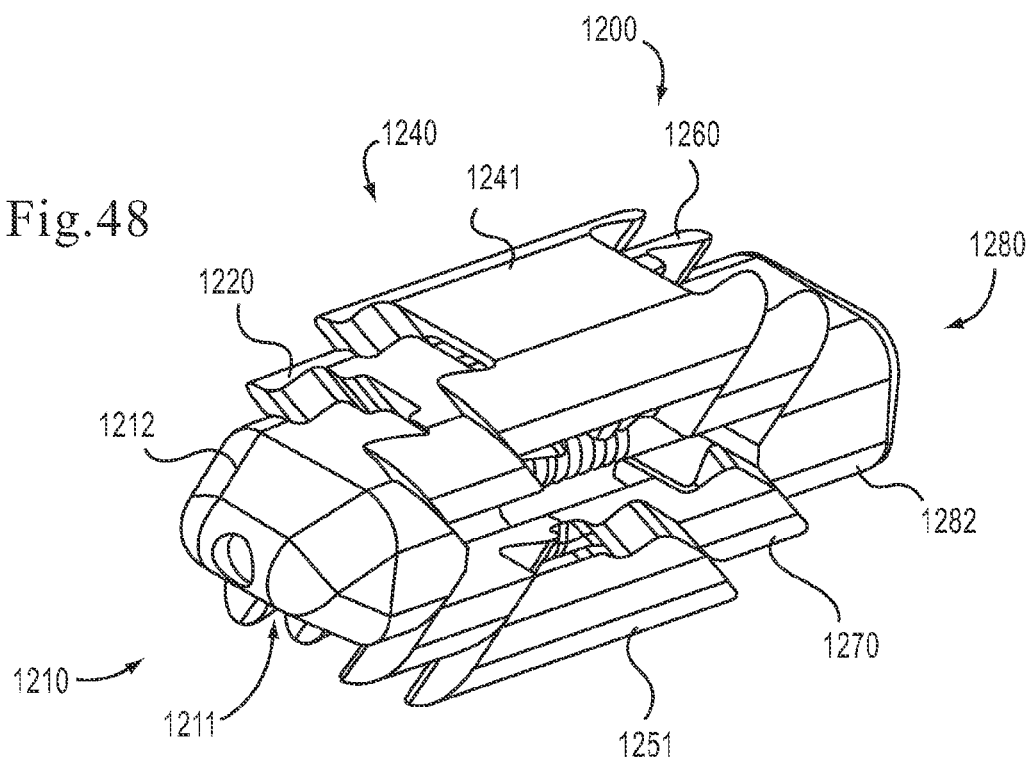

The first engagement surface 1216 of the actuator 1211 is angularly offset from the longitudinal axis A$_L$ of the implant 1200 by an angle between 0 degrees and 90 degrees. Similarly, the second engagement surface 1217 of the actuator 1211 is angularly offset from the longitudinal axis A$_L$ of the implant 1200 by an angle between 0 degrees and 90 degrees. As described above, the angular offset of the engagement surfaces 1216 and 1217 are associated with moving the implant 1200 between a first configuration (FIG. 47) and a second configuration (FIG. 48). More particularly, the angular offsets of the engagement surfaces 1216 and 1217 are associated with the force to move the implant 1200 between the first configuration and the second configuration. The angular offsets of the of the engagement surfaces 1216 and 1217 are also associated with the distance through which various components of the implant 1200 are moved when the implant 1200 is moved between the first configuration and the second configuration. Although the engagement surfaces 1216 and 1217 are shown and described as being non-parallel to and non-normal to the longitudinal axis A$_L$ of the implant 1200, in other embodiments, the engagement surfaces 1216 and 1217 can be substantially parallel to or substantially normal to the longitudinal axis A$_L$ of the implant 1200.

As shown in FIG. 57, the first protrusion 1218 of the actuator 1211 has an undercut such that the first distal intermediate member 1220 can be slidably coupled to the actuator 1211. More particularly, the first protrusion 1218 has a trapezoidal cross-sectional shape. In this embodiment, the first protrusion 1218 is a dovetail protrusion. Similarly, the second protrusion 1219 of the actuator 1211 has an undercut such that the second distal intermediate member 1230 can be slidably coupled to the actuator 1211. More particularly, the second protrusion 1219 has a trapezoidal cross-sectional shape. In this embodiment, the second protrusion 1219 is a dovetail protrusion.

The first distal intermediate member 1220 includes a first engagement surface 1222, a second engagement surface 1223 opposite the first engagement surface 1222 and a protrusion 1226. The first distal intermediate member 1220 defines a notch 1228 (see FIG. 59) configured to allow the drive screw 1283 to pass through the first distal intermediate member 1220 when the implant 1200 is in the first configuration. Said another way, when the implant 1200 is in the first configuration, the notch 1228 is aligned with the lumen 1246.

The protrusion 1226 of the first distal intermediate member 1220 extends from the second engagement surface 1223 and has a trapezoidal cross-sectional shape. In this embodiment, the protrusion 1226 is a dovetail protrusion configured to matingly and movably couple the first central support member 1241 of the central portion 1240 to the first distal intermediate member 1220.

The first engagement surface 1222 of the first distal intermediate member 1220 defines a plane that is angularly offset from the longitudinal axis $A_L$ of the implant 1200 by an angle between 90 degrees and 180 degrees. Moreover, the first engagement surface 1222 of the first distal intermediate member 1220 is substantially parallel to the engagement surface 1216 of the actuator 1211. Said another way, the angular offset of the first engagement surface 1222 of the distal retention member 1220 is supplementary with the angular offset of the engagement surface 1216 of the actuator 1211.

The first engagement surface 1222 of the first distal intermediate member 1220 defines a groove 1224 having a trapezoidal cross-sectional shape. In this embodiment, the groove 1224 has a dovetail shape that corresponds to the shape of the first protrusion 1218 of the actuator 1211. Accordingly, the first distal intermediate member 1220 and the actuator 1211 are matingly and movably coupled by the groove 1224 and the first protrusion 1218. Similarly stated, the groove 1224 and the first protrusion 1218 are collectively configured to limit movement of the first distal intermediate member 1220 relative to the actuator 1211 in a direction substantially normal to the first engagement surface 1222 of the first distal intermediate member 1220. Moreover, the groove 1224 and the first protrusion 1218 of the actuator 1211 collectively allow movement of the first distal intermediate member 1220 relative to the actuator 1211 in a direction substantially parallel to the first engagement surface 1222 of the first distal intermediate member 1220.

The second engagement surface 1223 of the first distal intermediate member 1220 defines a plane that is angularly offset from the longitudinal axis $A_L$ of the implant 1200 by an angle between 0 degrees and 90 degrees. Accordingly, the first distal intermediate member 1220 is slidably disposed against the first central support member 1241 of the central portion 1240.

The second distal intermediate member 1230 includes a first engagement surface 1232, a second engagement surface 1233 opposite the first engagement surface 1232, and a protrusion 1236. The protrusion 1236 of the second distal intermediate member 1230 extends from the second engagement surface 1233 and has a trapezoidal cross-sectional shape. In this embodiment, the protrusion 1236 is a dovetail protrusion configured to matingly and movably couple the second central support member 1251 of the central portion 1240 to the second distal intermediate member 1230.

Additionally, the second distal intermediate member 1230 defines a notch 1238 configured to allow the drive screw 1283 to pass through the second distal intermediate member 1230 when the implant 1200 is in the first configuration. Moreover, the first engagement surface 1232 of the second distal intermediate member 1230 defines a groove 1234. The second distal intermediate member 1230 is configured similar to the first distal intermediate member 1220, and is therefore not described in detail herein.

Proximal end portion 1280 of implant 1200 includes a tool engagement member 1282, a first proximal intermediate member 1260 and a second proximal intermediate member 1270. Tool engagement member 1282 is configured to mate with and/or receive an insertion tool, such as those described herein. Tool engagement member 1282 includes a first engagement surface 1286, a second engagement surface 1287, a first protrusion 1288 and a second protrusion 1289.

The first engagement surface 1286 of the tool engagement member 1282 is angularly offset from the longitudinal axis $A_L$ of the implant 1200 by an angle between 0 degrees and 90 degrees. Similarly, the second engagement surface 1287 of the tool engagement member 1282 is angularly offset from the longitudinal axis $A_L$ of the implant 1200 by an angle between 0 degrees and 90 degrees.

The first protrusion 1288 of the tool engagement member 1282 has an undercut such that the first proximal intermediate member 1260 can be slidably coupled to the tool engagement member 1282. More particularly, the first protrusion 1288 has a trapezoidal cross-sectional shape. In this embodiment, the first protrusion 1288 is a dovetail protrusion. Similarly, the second protrusion 1289 of the tool engagement member 1282 has an undercut such that the second proximal intermediate member 1270 can be slidably coupled to the tool engagement member 1282.

The first proximal intermediate member 1260 includes a first engagement surface 1262, a second engagement surface 1263 opposite the first engagement surface 1262 and a protrusion 1266. The first proximal intermediate member 1260 defines a notch 1268 configured to allow the drive screw 1283 to pass through the first proximal intermediate member 1260 when the implant 1200 is in the first configuration. Said another way, when the implant 1200 is in the first configuration, the notch 1268 is aligned with the lumen 1246.

The protrusion 1266 of the first proximal intermediate member 1260 extends from the second engagement surface 1263 and has a trapezoidal cross-sectional shape. In this embodiment, the protrusion 1266 is a dovetail protrusion configured to matingly and movably couple the first central support member 1241 of the central portion 1240 to the first proximal intermediate member 1260.

The first engagement surface 1262 of the first proximal intermediate member 1260 defines a plane that is angularly offset from the longitudinal axis $A_L$ of the implant 1200 by an angle between 90 degrees and 180 degrees. Moreover, the first engagement surface 1262 of the first proximal intermediate member 1260 is substantially parallel to the first engagement surface 1286 of the tool engagement member 1282.

The first engagement surface 1262 of the first proximal intermediate member 1260 defines a groove 1264 having a trapezoidal cross-sectional shape. In this embodiment, the groove 1264 has a dovetail shape that corresponds to the shape of the first protrusion 1288 of the tool engagement member 1282. Accordingly, the first proximal intermediate member 1260 and the tool engagement member 1282 are matingly and movably coupled by the groove 1264 and the first protrusion 1288. Similarly stated, the groove 1264 and the first protrusion 1288 are collectively configured to limit movement of the first proximal intermediate member 1260 relative to the tool engagement member 1282 in a direction substantially normal to the first engagement surface 1262 of the first proximal intermediate member 1260. Moreover, the groove 1264 and the first protrusion 1288 of the tool engagement member 1282 collectively allow movement of the first proximal intermediate member 1260 relative to the tool engagement member 1282 in a direction substantially parallel to the first engagement surface 1262 of the first proximal intermediate member 1260.

The second engagement surface 1263 of the first proximal intermediate member 1260 defines a plane that is angularly offset from the longitudinal axis $A_L$ of the implant 1200 by an angle between 0 degrees and 90 degrees. Accordingly, the first proximal intermediate member 1260 is slidably disposed against the first central support member 1241 of the central portion 1240.

The second proximal intermediate member 1270 includes a first engagement surface 1272, a second engagement surface 1273 opposite the first engagement surface 1272, and a protrusion 1276. The protrusion 1276 of the second proximal intermediate member 1270 extends from the second engagement surface 1273 and has a trapezoidal cross-sectional shape. In this embodiment, the protrusion 1276 is a dovetail protrusion configured to matingly and movably couple the second central support member 1251 of the central portion 1240 to the second proximal intermediate member 1270.

Additionally, the second proximal intermediate member 1270 defines a notch configured to allow the drive screw 1283 to pass through the second proximal intermediate member 1270 when the implant 1200 is in the first configuration. Moreover, the first engagement surface 1272 of the second proximal intermediate member 1270 defines a groove. The second proximal intermediate member 1270 is configured similar to the first proximal intermediate member 1260, and is therefore not described in detail herein.

The central portion 1240 of implant 1200 includes a first central support member 1241 and a second central support member 1251. The first central support member 1241 includes a proximal engagement surface 1242 and a distal engagement surface 1243. The first central support member 1241 defines a notch 1246 configured to allow the drive screw 1283 to pass through the first central support member 1241 when the implant 1200 is in the first configuration. Said another way, when the implant 1200 is in the first configuration, the notch 1246 is aligned with the lumen 1246.

The distal engagement surface 1243 of the first central support member 1241 defines a plane that is angularly offset from the longitudinal axis $A_L$ of the implant 1200 by an angle between 90 degrees and 180 degrees. Moreover, the angular offset of the distal engagement surface 1243 of the first central support member 1241 is supplementary with the angular offset of the second engagement surface 1223 of the first distal intermediate member 1220. Accordingly, the first central support member 1241 is slidably disposed against the first distal intermediate member 1220.

Moreover, the distal engagement surface 1243 of the first central support member 1241 defines a distal groove 1245. The distal groove 1245 is configured to receive and to slide along the protrusion 1226 of the first distal intermediate member 1220. The trapezoidal cross-section of the protrusion 1226 of the first distal intermediate member 1220 slidably maintains the protrusion 1226 of the first distal intermediate member 1220 within the distal groove 1245. The distal engagement surface 1243 of the first central support member 1241 contacts and is configured to slide along the second engagement surface 1223 of the first distal intermediate member 1220 when the distal groove 1245 slides along the protrusion 1226 of the first distal intermediate member 1220.

The proximal engagement surface 1242 of the first central support member 1241 defines a plane that is angularly offset from the longitudinal axis $A_L$ of the implant 1200 by an angle between 90 degrees and 180 degrees. Moreover, the angular offset of the proximal engagement surface 1242 of the first central support member 1241 is supplementary with the angular offset of the second engagement surface 1263 of the first proximal intermediate member 1260. Accordingly, the first central support member 1241 is slidably disposed against the first proximal intermediate member 1260.

Moreover, the proximal engagement surface 1242 of the first central support member 1241 defines a proximal groove 1244. The proximal groove 1244 is configured to receive and to slide along the protrusion 1266 of the first proximal intermediate member 1260. The trapezoidal cross-section of the protrusion 1266 of the first proximal intermediate member 1260 slidably maintains the protrusion 1266 of the first proximal intermediate member 1260 within the proximal groove 1244. The proximal engagement surface 1242 of the first central support member 1241 contacts and is configured to slide along the second engagement surface 1263 of the first proximal intermediate member 1260 when the proximal groove 1244 slides along the protrusion 1266 of the first proximal intermediate member 1260.

Likewise, the second central support member 1251 of the central portion 1240 includes a proximal engagement surface 1252 and a distal engagement surface 1253. The second central support member 1251 defines a notch 1256 configured to allow the drive screw 1283 to pass through the second central support member 1251 when the implant 1200 is in the first configuration. The proximal engagement surface 1252 defines a proximal groove 1254 and the distal engagement surface 1253 defines a distal groove 1255. The second central support member 1251 is configured similar to the first central support member 1241 described above.

Implant 1200 has multiple configurations. FIG. 47 shows the implant 1200 in a first configuration. In the first configuration, the proximal end portion 1280, the distal end portion 1210 and the central portion 1240 are substantially coaxial (i.e., substantially share a common longitudinal axis). Moreover, the first central support member 1241 is in contact with the second central support member 1251.

The implant 1200 can be moved from the first configuration to a second configuration as illustrated in FIG. 48. In the second configuration the first distal intermediate member 1220, the second distal intermediate member 1230, the first proximal intermediate member 1260, the second proximal intermediate member 1270, the first central support member 1241 and/or the second central support member 1251 can be offset from the actuator 1211 and the tool engagement member 1282.

In use, implant 1200 can be inserted percutaneously into a disc space (not shown in FIGS. 47-60). In this manner, the implant 1200 can be used, for example, as a fusion cage. Accordingly, in some embodiments, various portions of the implant 1200 (e.g., the outer surfaces of the central element 1240) can include features to enhance its biomechanical performance. Such features can include, for example, holes and/or textured surfaces within which bone material and/or bone growth enhancing substances can be disposed.

The implant 1200 can be inserted when in the first configuration, by, for example, an insertion tool as shown herein. The distal end portion 1210 can be inserted first and is moved past the center of the disc space until at least the central portion 1240 is positioned within the disc space. Once in the disc space, the implant 1200 can be moved from the first configuration to the second configuration. In the second configuration, the first and second proximal intermediate members 1260, 1270 and the first and second distal intermediate members 1220, 1230 can be offset from the actuator 1211 and the tool engagement member 1282. This causes the first central support member 1241 of the central portion 1240 and the second central support member 1251 of the central portion 1240 to move in relation to the actuator 1211 and the tool engagement member 1282 as further described herein. In this manner, the first central support member 1241 and the second central support member 1251 can distract and/or maintain a minimal spacing of the disc space. More particularly, the first central support member 1241 and the second central support member 1251 can contact the vertebral endplates to stabilize the spinal segment within which the implant 1200 is disposed.

To move the implant 1200 from the first configuration to the second configuration, the drive screw 1283 is rotated within the actuator 1211. In some embodiments, the drive screw 1283 can be rotated by an insertion tool such as those described in U.S. patent application Ser. No. 12/182,425 entitled "Tools and Methods for insertion and Removal of Medical Implants," which is incorporated herein by reference in its entirety. The insertion tool (not shown) can be configured to be removably coupled to the tool engagement member 1282 such that rotation of the tool engagement member 1282 relative to the insertion tool about the longitudinal axis $A_L$ is limited. In some embodiments, the insertion tool can be configured to be removably coupled to the tool engagement member 1282 such that axial movement of the tool engagement member 1282 relative to the insertion tool is limited. In some embodiments, for example, the insertion tool can be coupled to an outer surface of the tool engagement member 1282. In such embodiments, the outer surface of the tool engagement member 1282 can be configured to facilitate the docking of the insertion tool (not shown) to the implant 1200. For example, in some embodiments, the outer surface of the tool engagement member 1282 can include a lead-in chamfer, a tapered portion and/or a beveled edge to facilitate the docking of the insertion to onto the tool engagement member 1282 of the implant 1200. In other embodiments, the insertion tool can be matingly coupled to a protrusion and/or a recess of the tool engagement member 1282. The insertion tool can include an actuator configured to be inserted into the tool head 1284 of the drive screw 1283 to rotate the drive screw 1283 about the longitudinal axis $A_L$. This arrangement allows the drive screw 1283 to be rotated without rotating the other portions of the implant 1200.

Figure 49:
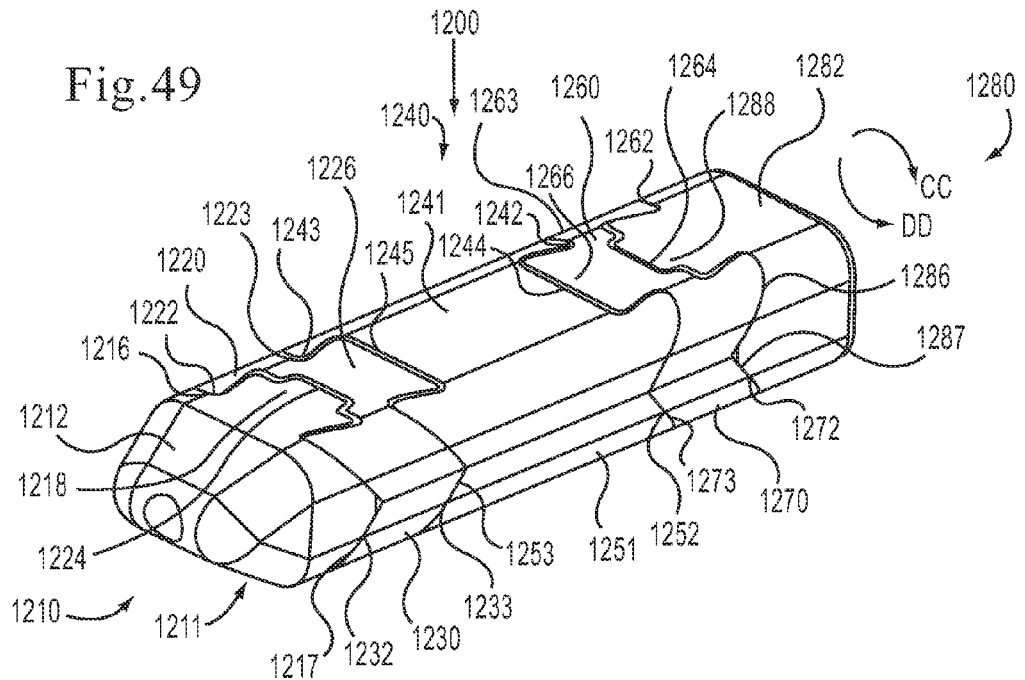
FIGS. 49 and 50 are perspective views of the implant shown in FIG. 47 in a first configuration and a second configuration, respectively.
Figure 50:
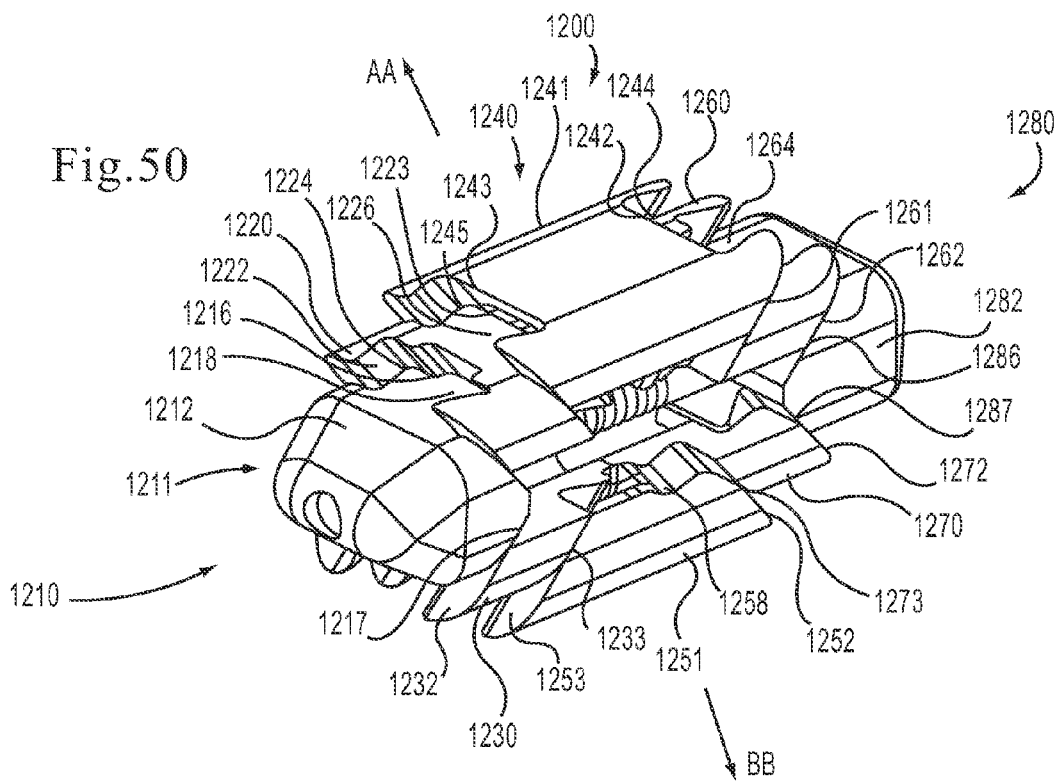

When the drive screw 1283 is rotated as indicated by the arrow CC in FIG. 49, the drive screw 1283 moves the actuator 1211 relative to the tool engagement member 1282, and towards the central portion 1240. Accordingly, the first engagement surface 1216 of the actuator 1211 exerts a force on the first engagement surface 1222 of the first distal intermediate member 1220, and the second engagement surface 1217 of the actuator 1211 exerts a force on the first engagement surface 1232 of the second distal intermediate member 1230. These forces cause the first distal intermediate member 1220 to slide on the first engagement surface 1216 of the actuator 1211 causing the first distal intermediate member 1220 to move in the direction AA (see FIG. 50), and the second distal intermediate member 1230 to slide on the second engagement surface 1217 of the actuator 1211 causing the second distal intermediate member 1230 to move in the direction BB.

Similarly, when the drive screw 1283 is rotated as indicated by the arrow CC in FIG. 49, the first engagement surface 1286 of the tool engagement member 1282 exerts a force on the first engagement surface 1262 of the first proximal intermediate member 1260 and the second engagement surface 1287 of the tool engagement member 1282 exerts a force on the first engagement surface 1272 of the second proximal intermediate member 1270. These forces cause the first proximal intermediate member 1260 to slide on the first engagement surface 1286 of the tool engagement member 1282 causing the first proximal intermediate member 1260 to move in the direction AA, and the second proximal intermediate member 1270 to slide on the second engagement surface 1287 of the tool engagement member 1282 causing the second proximal intermediate member 1270 to move in the direction BB.

As the first distal intermediate member 1220 slides on the first engagement surface 1216 of the actuator 1211, the second engagement surface 1223 of the first distal intermediate member 1220 exerts a force on the distal engagement surface 1243 of the first central support member 1241 of the central portion 1240. Likewise, as the first proximal intermediate member 1260 slides on the first engagement surface 1286 of the tool engagement portion 1282, the second engagement surface 1263 of the first distal intermediate member 1260 exerts a force on the proximal engagement surface 1242 of the first central support member 1241 of the central portion 1240. The force exerted on the distal engagement surface 1243 of the first central support member 1241 and the force exerted on the proximal engagement surface 1242 of the first central support member 1241 cause the first central support member 1241 to move in the direction AA.

Furthermore, as the second distal intermediate member 1230 slides on the second engagement surface 1217 of the actuator 1211, the second engagement surface 1233 of the second distal intermediate member 1230 exerts a force on the distal engagement surface 1253 of the second central support member 1251 of the central portion 1240. Likewise, as the second proximal intermediate member 1270 slides on the second engagement surface 1287 of the tool engagement portion 1282, the second engagement surface 1273 of the second distal intermediate member 1270 exerts a force on the proximal engagement surface 1252 of the second central support member 1251 of the central portion 1240. The force exerted on the distal engagement surface 1253 of the second central support member 1251 and the force exerted on the proximal engagement surface 1252 of the second central support member 1251 causes the second central support member 1251 to move in the direction AA.

To remove and/or reposition the implant 1200, the drive screw 1283 is rotated as indicated by the arrow DD in FIG. 49, by for example, a removal tool (may be similar to an insertion tool). Rotating the drive screw 1283 in direction DD, causes the dovetail configuration of the protrusions 1218, 1219 of the actuator 1211 and the dovetail configurations of the protrusions 1288, 1289 of the tool engagement member 1282 to pull the distal intermediate members 1220, 1230 and the proximal intermediate members 1260, 1270 back into the first configuration. This causes the dovetail configurations of the protrusions 1226, 1236 of the distal intermediate members 1220, 1230 and the dovetail configurations of the protrusions 1266, 1276 of the proximal intermediate members 1260, 1270 to pull the support members 1241, 1251 back into the first configuration.

Although the implant 1200 is shown is being movable between a first configuration (FIG. 49) and a second configuration (FIG. 50), the implant 1200 can be maintained in any number of different configurations. For example, the implant 1200 can be maintained in any suitable configuration between the first configuration and the second configuration. Said another way, the implant 1200 can be placed in an infinite number of different configurations between the first configuration and the second configuration. Thus, the disc space can be distracted by the first central support member 1241 and the second central support member 1251 by any desired amount within a predetermined range. In this manner, a single implant 1200 can be used to treat a wide range of conditions and/or locations within the body requiring different amounts of distraction. Moreover, this arrangement allows the amount of distraction to be varied in situ over time.

For example, in some embodiments, the amount of distraction can be varied within a range of approximately 8 mm to 16 mm. Within this range, the size of the central portion 1240 can be adjusted to any desired amount by rotating the drive screw 1283 a predetermined amount, as described above. In other embodiments, the range of distraction can be approximately 4 mm (e.g., a range from 5 mm to 9 mm, a range from 12 mm to 16 mm, or the like). In yet other embodiments, the range of distraction can be approximately 3 mm (e.g., a range from 10 mm to 13 mm, a range from 12 mm to 15 mm, or the like).

Figure 62:
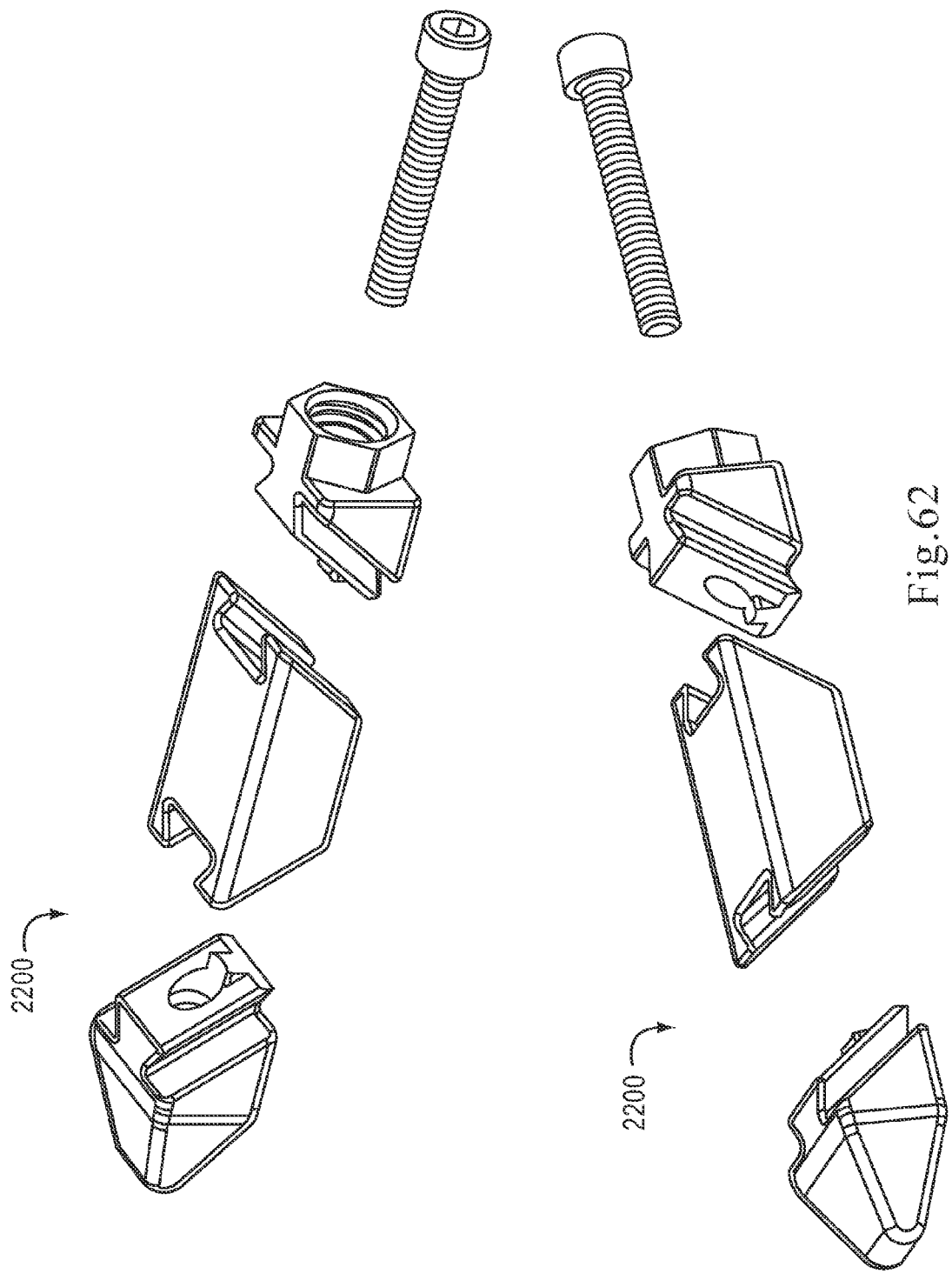
Figure 63:
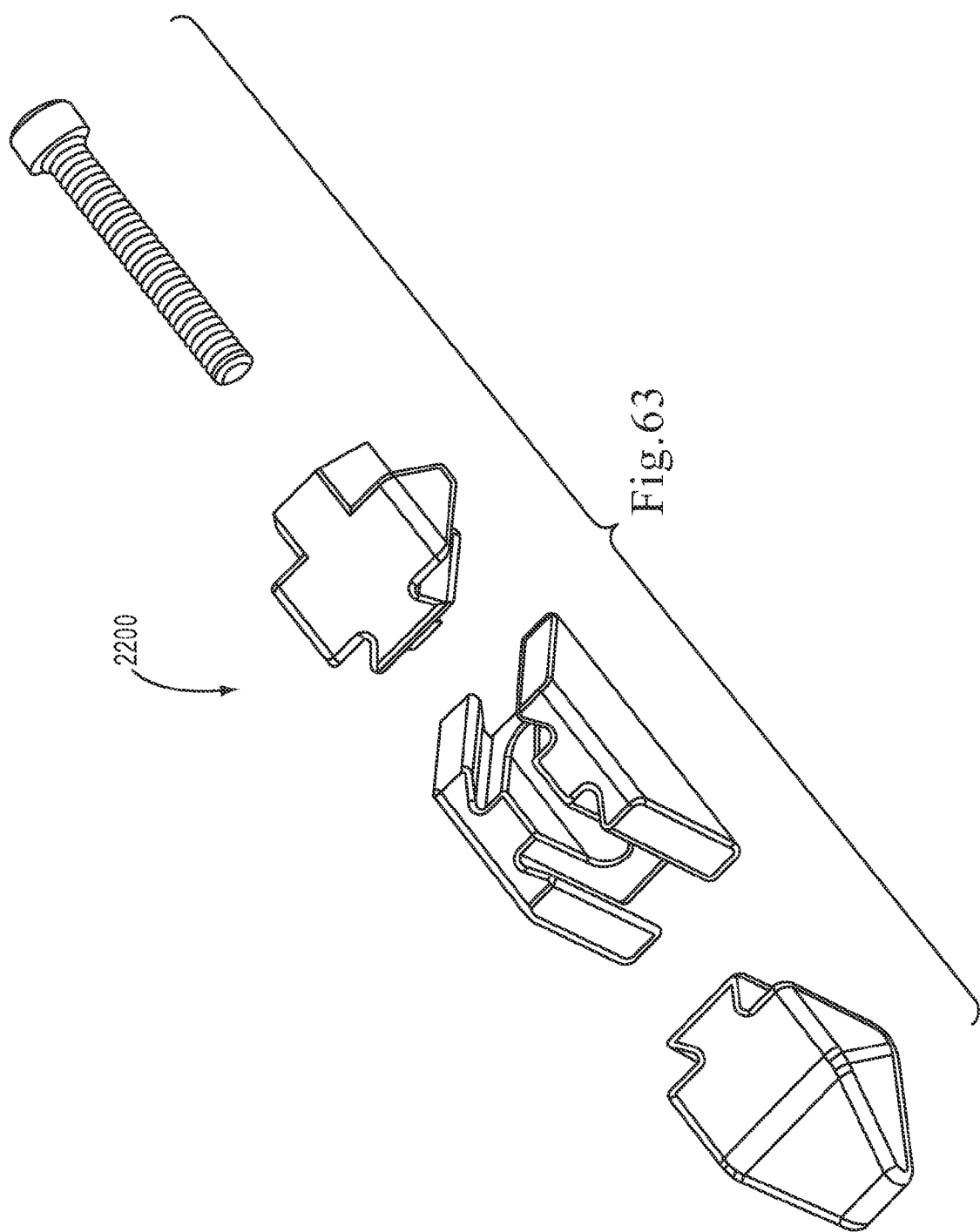

FIGS. 61-63 show an implant 2200 according to an embodiment. The implant 2200 is structured like and functions similar to the implant 1220 without intermediate members 2220, 2230, 2260 and 2270, but with a single central support member. FIG. 61 shows various views of the implant 2200 in a first configuration and a second configuration. FIGS. 62 and 63 show exploded views of the implant 2200. In use, implant 2200 is inserted percutaneously into a disc space (not shown in FIGS. 61-63), in the first configuration, by, for example, an insertion tool as described in U.S. patent application Ser. No. 12/182,425 entitled "Tools and Methods for insertion and Removal of Medical Implants," which is incorporated herein by reference in its entirety. The implant 2200 can then be moved into the second configuration to maintain a minimal spacing of the disc space. The implant 2200 may also be used as a distraction tool; in such a use, the implant 2200 can be moved into the second configuration to move the spinous processes.

The various implants, deployment/insertion tools, and guide members described herein can be constructed with various biocompatible materials such as, for example, titanium, titanium alloyed, surgical steel, biocompatible metal alloys, stainless steel, plastic, polyetheretherketone (PEEK), carbon fiber, ultra-high molecular weight (UHMW) polyethylene, biocompatible polymeric materials, etc. The material of a central portion of the implant can have, for example, a compressive strength similar to or higher than that of bone. In one embodiment, the central portion of the implant, which is placed between the two adjacent spinous processes, is configured with a material having an elastic modulus higher than the elastic modulus of the bone, which forms the spinous processes. In another embodiment, the central portion of the implant is configured with a material having a higher elastic modulus than the materials used to configure the distal and proximal portions of the implant. For example, the central portion of the implant may have an elastic modulus higher than bone, while the proximal and distal portions have a lower elastic modulus than bone. In yet another embodiment, the implant is configured with an outer shell and an inner core. The outer shell can be configured with material having a higher elastic modulus than the inner core (e.g., outer shell is made with titanium alloyed, while the inner core is made with a polymeric material). Alternatively, the outer shell can be configured with a material having a lower elastic modulus than the inner core (e.g., the outer shell is made with a polymeric material while the inner core is made with a titanium alloyed material).

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although the interspinous process implant 1100 and the disc implant 1200 are shown and described as including protrusions and grooves configured to matingly couple various components thereof, in other embodiments, an interspinous process implant and/or a disc implant need not include components that are matingly coupled. For example, in some embodiments, a disc implant can include an actuator configured to actuate a spacer that is devoid of mating protrusions and/or grooves. Similarly, in some embodiments, an interspinous process implant can include an actuator configured to actuate a retention member that is devoid of mating protrusions and/or grooves. For example, in such embodiments, a retention member can be magnetically coupled to the actuator.

Although the engagement surfaces are shown and described above as being planar, in some embodiments, an implant can include an engagement surface that is curved.

In some embodiments, the implants shown and described can be biased in the first configuration or the second configuration. For example in some embodiments, an implant can include a spring and/or the like to bias a portion of the implant as desired. Additionally, in some embodiments an implant can include a locking member to temporally maintain the implant in a particular configuration. Similarly stated, in some embodiments an implant can include a locking member configured to temporally maintain the implant in the first configuration if the implant is biased to be in the second configuration, and vise versa. For example, a locking member can be disposed within a retention member such that an end portion of the locking member is received within a recess of a central body to temporarily maintain the implant in a first and/or a second configuration. In other embodiments, an implant can include a first locking member or detent to temporarily maintain the implant in a first configuration and/or a second locking member or detent to temporarily maintain the implant in a second configuration.

As discussed herein, the implants shown and described above can be inserted into the body percutaneously and/or in a minimally-invasive manner. For example, in some embodiments, an implant of the types shown and described above can be inserted through a skin incision of less than 20 mm in length. In other embodiments, an implant of the types shown and described above can be inserted through a skin incision of less than 15 mm in length. In yet other embodiments, an implant of the types shown and described above can be inserted through a skin incision of less than 10 mm in length.

Figure 64:
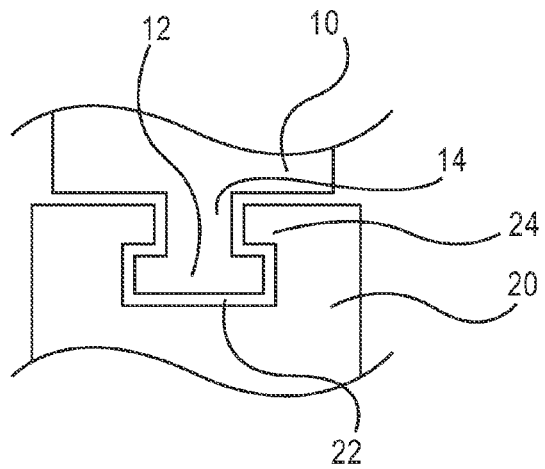
FIG. 64 shows a connection portion of an implant according to an embodiment.
Figure 65:
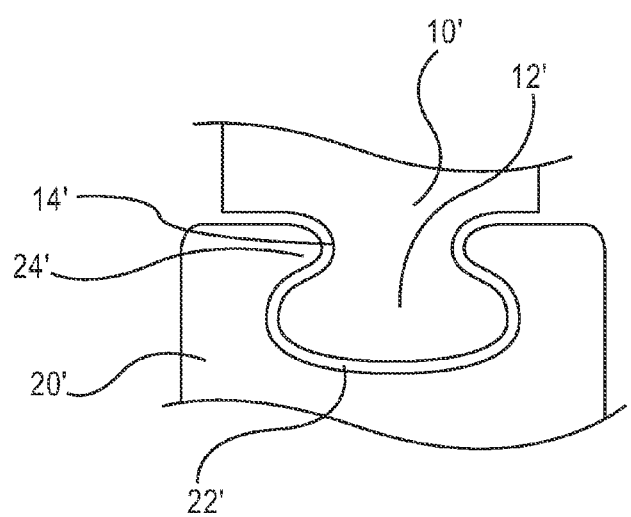
FIG. 65 shows a connection portion of an implant according to an embodiment.
Figure 66:
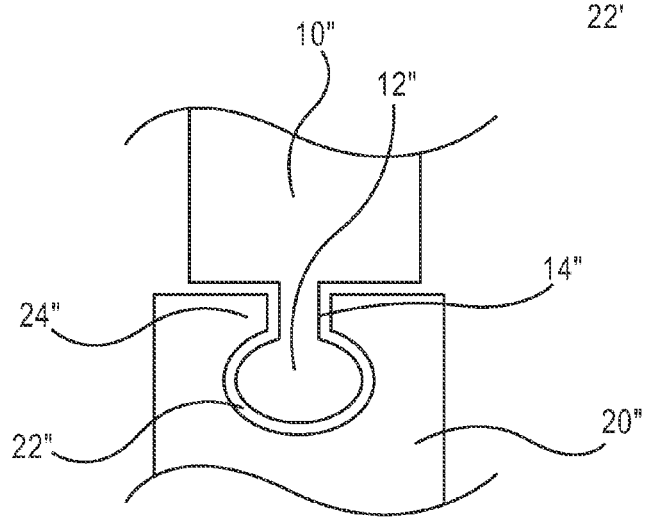
FIG. 66 shows a connection portion of an implant according to an embodiment.

Although many of the implants shown and described above include components (e.g., an actuator) having a dovetail protrusion configured to be matingly and movably coupled to other components (e.g., a retention member or spacer) having a dovetail groove, it should be understood that either component can include the protrusion and/or the groove. Moreover, although the protrusions and/or grooves are described above as being dovetail protrusions and/or grooves, in other embodiments, an implant can include components that are matingly and movably coupled together by any suitable type of protrusion and groove. For example, FIGS. 64-66 show examples of protrusions and grooves that can be used to matingly and movably couple components of any of the implants described herein. FIG. 64 shows a first implant component 10 matingly and movably coupled to a second implant component 20. The first implant component 10 has a protrusion 12 having an undercut 14. The second implant 20 defines a groove 22 having an undercut 24. The protrusion 12 is disposed within the groove 22 such that the first implant component 10 can move relative to the second implant component 20 (e.g., in a direction normal to the plane shown in FIG. 64), while remaining coupled together.

FIG. 65 shows a first implant component 10' matingly and movably coupled to a second implant component 20'. The first implant component 10' has a curved protrusion 12' having an undercut 14'. The second implant 20' defines a groove 22' having a curved shape and having an undercut 24'. The protrusion 12' is disposed within the groove 22' such that the first implant component 10' can move relative to the second implant component 20' (e.g., in a direction normal to the plane shown in FIG. 65), while remaining coupled together.

FIG. 66 shows a first implant component 10" matingly and movably coupled to a second implant component 20". The first implant component 10" has a circular protrusion 12" having an undercut 14". The protrusion 12" can also be a substantially spherical protrusion. The second implant 20" defines a groove 22" having a circular (or substantially spherical) shape and having an undercut 24". The protrusion 12" is disposed within the groove 22" such that the first implant component 10" can move relative to the second implant component 20" (e.g., in a direction normal to the plane shown in FIG. 66), while remaining coupled together.

Although various embodiments have been described as having particular features and/or combinations of components, other embodiments are possible having a combination of any features and/or components from any of embodiments where appropriate. For example, in some embodiments, a disc implant similar to the implant 1200 can include a tool engagement portion similar to the tool engagement portion of the implant 3100.

What is claimed is:

1. A spinal implant, comprising:
   a spacer configured to engage a first spinous process and a second spinous process; the spacer having a proximal surface and a distal surface opposite the proximal surface;
   a proximal retention member disposed proximally relative to the spacer and movably coupled to the spacer such that a portion of the proximal retention member is in contact with the proximal surface of the spacer;
   a distal retention member having a first surface and a second surface, the distal retention member disposed distally relative to the spacer and movably coupled to the spacer such that the second surface is in contact with the distal surface of the spacer;
   a drive screw extending along a longitudinal axis;
   an axis within a plane defined by the first surface of the distal retention member being non-parallel to and non-normal to the longitudinal axis;
   an actuator segment disposed distally relative to the distal retention member;
   the actuator segment movably coupled to the spacer for movement relative to the spacer along the longitudinal axis;
   the actuator segment having an actuation surface slidably coupled to and substantially parallel to the first surface of the distal retention member;
   wherein the distal retention member is separate and distinct from both the spacer and the actuator segment;
   wherein the proximal retention member is separate and distinct from both the spacer and the actuator segment;
   wherein the implant is changeable from a retracted configuration to a deployed configuration;
   wherein, in the retracted configuration:
   the actuator segment is spaced from the distal surface of the spacer and the distal retention member longitudinally separates the actuator segment from the spacer;
   an outer surface of the proximal retention member and an outer surface of the distal retention member are disposed relatively closer to the longitudinal axis;
   the drive screw extends into the actuator segment a first distance;
   wherein, in the deployed configuration:
   the actuator segment abuts the distal surface of the spacer on a first side of the longitudinal axis and the distal retention member is disposed between the actuator segment and the distal surface of the spacer on a second side of the longitudinal axis;
   the outer surface of the proximal retention member and the outer surface of the distal retention member are disposed relatively farther from the longitudinal axis;
   the drive screw extends into the actuator segment a second distance larger than the first distance.

2. The spinal implant of claim 1 wherein the proximal retention member and the distal retention member are configured to collectively limit movement of the spacer along the longitudinal axis and relative to the first spinous process and the second spinous process when the implant is in the deployed configuration.

3. The spinal implant of claim 1 wherein the distal retention member moveably mates to the spacer at a first tongue-and-groove connection; wherein the proximal retention member moveably mates to the spacer at a second tongue-and-groove connection.

4. The spinal implant of claim 1 wherein, in the retracted configuration, the outer surface of the distal retention member and the outer surface of the proximal retention member are both generally aligned with an outer surface of the spacer such that the outer surfaces lie in a common plane parallel to the longitudinal axis.

5. The spinal implant of claim 1 wherein:
   the first surface of the distal retention member defines a groove;
   the actuation surface of the actuator segment includes a protrusion configured to be matingly received within the groove;
   the groove and the protrusion collectively configured to allow movement of the distal retention member relative to the actuator segment in a direction substantially parallel to the first surface of the distal retention member;
   the groove and the protrusion collectively configured to limit movement of the distal retention member relative to the actuator segment in a direction substantially normal to the first surface of the distal retention member.

6. The spinal implant of claim 5 wherein:
   the groove of the first surface has a trapezoidal cross-sectional shape;
   the protrusion of the actuation surface has a trapezoidal cross-sectional shape.

7. The spinal implant of claim 1, wherein:
   the second surface of the distal retention member is slidably coupled to the distal surface of the spacer; the second surface of the distal retention member defines a groove;
   the distal surface of the spacer includes a protrusion configured to be matingly received within the groove;
   the groove and the protrusion collectively configured to allow movement of the distal retention member relative to the spacer in a direction substantially parallel to the second surface of the distal retention member;

the groove and the protrusion collectively configured to limit movement of the distal retention member relative to the spacer in a direction substantially normal to the second surface of the distal retention member.

8. The spinal implant of claim 1 wherein:

the distal surface of the spacer is substantially normal to the longitudinal axis;

the second surface of the distal retention member is slidably coupled to and substantially parallel to the distal surface of the spacer.

9. The spinal implant of claim 1 wherein the actuator segment tapers inward toward the longitudinal axis in a direction away from the spacer.

* * * * *